(12) United States Patent
Hu et al.

(10) Patent No.: US 7,507,860 B2
(45) Date of Patent: Mar. 24, 2009

(54) ANDROGEN MODULATORS

(75) Inventors: Lain-Yen Hu, Ann Arbor, MI (US);
Huangshu Lei, Waltham, MA (US);
Daniel Y. Du, Milan, MI (US); Bruce A. Lefker, Gales Ferry, CT (US); Yvonne Dorothy Smith, Ypsilanti, MI (US);
Victor Fedij, Brighton, MI (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/599,143

(22) PCT Filed: Apr. 1, 2005

(86) PCT No.: PCT/IB2005/000872

§ 371 (c)(1),
(2), (4) Date: Sep. 21, 2006

(87) PCT Pub. No.: WO2005/100305

PCT Pub. Date: Oct. 27, 2005

(65) Prior Publication Data

US 2007/0197641 A1    Aug. 23, 2007

Related U.S. Application Data

(60) Provisional application No. 60/561,812, filed on Apr. 13, 2004.

(51) Int. Cl.
*C07C 211/08* (2006.01)
(52) U.S. Cl. ...................... 564/347; 564/348
(58) Field of Classification Search .............. 564/348, 564/347
See application file for complete search history.

(56) References Cited

U.S. PATENT DOCUMENTS

| | | | |
|---|---|---|---|
| 4,029,493 A | 6/1977 | Theissen | |
| 4,234,595 A | 11/1980 | Kreighbaum | |
| 4,263,223 A | 4/1981 | Pauly | |
| 4,536,321 A | 8/1985 | Sugimori et al. | |
| 4,783,397 A * | 11/1988 | Ogawa et al. | 430/389 |
| 4,992,433 A | 2/1991 | Stokbroekx | |
| 5,108,652 A | 4/1992 | Eidenshink | |
| 5,316,755 A | 5/1994 | Illig et al. | |
| 5,847,166 A | 12/1998 | Buchwald | |
| 5,910,493 A | 6/1999 | Golbs | |
| 5,990,142 A | 11/1999 | Carganico et al. | 514/382 |
| 6,011,606 A | 1/2000 | Ohe | |
| 2003/0175445 A1 | 9/2003 | Kirsch et al. | |
| 2003/0229129 A1 | 12/2003 | Kraemer et al. | |
| 2003/0232882 A1 | 12/2003 | Miller et al. | |
| 2004/0087557 A1* | 5/2004 | Steiner et al. | 514/114 |
| 2005/0182132 A1 | 8/2005 | Hu et al. | |
| 2006/0009427 A1 | 1/2006 | Hu et al. | |

FOREIGN PATENT DOCUMENTS

| | | |
|---|---|---|
| CN | 1214048 | 4/1999 |
| DE | 2301541 | 9/1973 |
| DE | 3825170 A1 | 1/1990 |
| DE | 10126434 A | 12/2002 |
| EP | 15505 4 | 9/1980 |
| EP | 0002309 | 12/1982 |
| EP | 0080371 A1 | 6/1983 |
| EP | 0119756 | 9/1984 |
| EP | 0193303 | 9/1986 |
| EP | 221844 A | 5/1987 |
| EP | 100172 B1 | 8/1987 |
| EP | 269383 A | 6/1988 |
| EP | 412814 A | 2/1991 |
| EP | 419286 A | 3/1991 |
| EP | 488474 A1 | 6/1992 |
| EP | 0601977 A1 | 6/1994 |
| EP | 0609587 A | 8/1994 |
| EP | 0673986 A2 | 3/1995 |
| EP | 654468 A1 | 5/1995 |
| EP | 0684235 A1 | 11/1995 |
| EP | 0579223 | 10/1996 |
| EP | 0790235 A1 | 8/1997 |
| EP | 1070753 A2 | 1/2001 |
| EP | 1123933 A1 | 8/2001 |
| EP | 0707007 B1 | 12/2001 |
| EP | 1325910 A1 | 7/2003 |
| EP | 1348433 A | 10/2003 |
| EP | 1348701 A | 10/2003 |
| GB | 1369696 A | 10/1974 |

(Continued)

OTHER PUBLICATIONS

Advanced Drug Delivery Reviews 48 (2001) 3-26.*

(Continued)

*Primary Examiner*—Kamal A Saeed
*Assistant Examiner*—Shawquia Young
(74) *Attorney, Agent, or Firm*—Gregg C. Benson; J. Michael Dixon

(57) ABSTRACT

The present invention is directed to a new class of 4-cyano-phenoxy-alkyl carboxyl derivatives and to their use as androgen receptor modulators. Other aspects of the invention are directed to the use of these compounds to decrease excess sebum secretions and to stimulate hair growth.

17 Claims, No Drawings

FOREIGN PATENT DOCUMENTS

| | | |
|---|---|---|
| GB | 2278054 A | 11/1994 |
| GB | 2347423 A | 9/2000 |
| JP | 59144747 | 8/1984 |
| JP | 61189243 | 8/1986 |
| JP | 04124183 | 4/1992 |
| JP | 04300877 | 10/1992 |
| JP | 5310616 | 11/1993 |
| JP | 07309850 | 11/1995 |
| JP | 8325154 | 12/1996 |
| JP | 10007647 A | 1/1998 |
| WO | WO9219210 A2 | 11/1992 |
| WO | WO94/05153 A | 3/1994 |
| WO | WO9510521 A1 | 4/1995 |
| WO | WO95/28969 | 11/1995 |
| WO | WO 9626921 | 9/1996 |
| WO | WO9735845 A1 | 10/1997 |
| WO | WO98/33779 | 8/1998 |
| WO | WO99/08673 A | 2/1999 |
| WO | WO99/17777 | 4/1999 |
| WO | WO0034247 A | 6/2000 |
| WO | WO0034269 A | 6/2000 |
| WO | WO0037430 | 6/2000 |
| WO | WO0059888 A | 10/2000 |
| WO | WO01/56989 A2 | 8/2001 |
| WO | WO02/06196 | 1/2002 |
| WO | WO0218333 A | 3/2002 |
| WO | WO0220484 A | 3/2002 |
| WO | WO0236734 A | 5/2002 |
| WO | WO0241889 A | 5/2002 |
| WO | WO02/057215 A2 | 7/2002 |
| WO | WO02060896 A | 8/2002 |
| WO | WO02070484 A | 9/2002 |
| WO | WO02/085860 A1 | 10/2002 |
| WO | WO02/090332 A2 | 11/2002 |
| WO | WO03/065992 A | 8/2003 |
| WO | WO03066632 A | 8/2003 |
| WO | WO03068217 A | 8/2003 |
| WO | WO03068754 | 8/2003 |
| WO | WO03/074473 A2 | 9/2003 |
| WO | WO 03082787 | 10/2003 |
| WO | WO03/093243 A1 | 11/2003 |
| WO | WO2004/018386 A2 | 3/2004 |
| WO | WO2004110994 A1 | 12/2004 |
| WO | WO2005000794 | 1/2005 |
| WO | WO2005013914 A | 2/2005 |
| WO | WO2005042464 A1 | 5/2005 |
| WO | WO2005/049574 A1 | 6/2005 |
| WO | WO2005080320 A1 | 9/2005 |
| WO | WO2005/100305 A1 | 10/2005 |
| WO | WO2005/102990 A1 | 11/2005 |
| WO | WO2005/108361 A1 | 11/2005 |
| WO | WO2006/006065 A1 | 1/2006 |
| WO | WO2006/018723 A2 | 2/2006 |
| WO | WO2006018732 A | 2/2006 |
| WO | WO2006/024942 A1 | 3/2006 |
| WO | WO2006/049952 A1 | 5/2006 |

OTHER PUBLICATIONS

Database Caplus Online Chemical Abstracts Service. Columbus, Ohio US Bero. S,S. et al, chemotherapeutic amidines X. Substituted 4,4'-diamidino-omega, omega.-diphenoxyalkanes and diphenyl ethers XP002333841 retreived from STN Database accession No. 1949:50548 abstract & Journal of the Chemical Society Abstracts. 1949. pp. 642-648.

Database Caplus Online Chemical Abstracts Service, Columbus, Ohio US Kratzl, K. et al: "Chemistry of vanillin and its derivatives X. Amidines imidazolines, and tetrahydropyrimidinediones with quai-acol substituents" XP002333842 Retrieved from STN Database accession No. 1958:65868 abstract & Monatshefte Fuer Chemie. 88, 1957, pp. 1056-1063.

Database Caplus Online Chemical Abstracts Service, Columbus, Ohio US Davis, M.: "Search for chemotherapeutic amidines. XV. 2-Methoxy and 2-hydroxy derivatives of 1,5-bis(p-amidinophenoxy) pentane" XP002333843 retrieved from STN Database accession No. 1958:82447 abstract & Journal of the Chemical Society, Abstracts, 1958. pp. 907-908.

Data Base CA Online Chemical Abstract Service, Columbus, Ohio, US; Ferroni, R. et al., "Aromatic tetra-amidines: synthesis of halo-derivatives and their antiproteolytic activity" XP002333844 retrieved from STN Database accession No. 1985:91904 abstract & Farmaco, Edizione Scientifica, vol. 39, No. 11, 1984, pp. 901-909.

Data Base Caplus Online Chemical Abstracts Service, Columbus, Ohio US Leznoff, Clifford C et al: "Metallophthalocyanine dimers incorporating five-atom covalent bridges" XP002333845 retrived from STN Database accession No. 1985:447150 abstract & Canadian Journal of Chemistry vol. 63, No. 3, 1985, pp. 623-631.

Data Base Caplus Online Chemical Abstracts Service, Columbus, Ohio US Woehrle, Dieter et al: "Polymeric phthalocyanines and their precursors. 15. Syntheses of alkylenedioxy-bridged polymeric phthalocyanines and their absorption capacities for organic solvents in comparison to other phthalocyanines" XP002333846 retrieved from STN Database accession No. 1988:493734 abstract & Makromolekulare Chemie, vol. 189, No. 6, 1988, pp. 1229-1238.

Geratz. J.D. et al: "Diamidino-alpha., omega-diphenoxyalkane s. Structure-activity relations for the inhibition of thrombin, pancreatic kallikrein, and trypsin" Journal of Medicinal Chemistry, vol. 16, No. 9, 1973, pp. 970-975, XP002333840 table VI, compounds 27-30, 32-34, 37.

Database Caplus Online Chemical Abstracts Service, Columbus. Ohio US, Csokai, Viktor et al: "Microwave-assisted synthesis of phtalonitriles and phthalocyanines"XP002333847 retrieved from STN Database accession No. 2003:416216 abstract & Synthetic Communications, vol. 33, No. 10, 2003, pp. 1615-1621.

Database Caplus, Online Chemical Abstracts Service, Columbus, Ohio, US; Eastmond, G.C. et al: "Polyimides with main-chain ethylene oxide units:synthesis and properties" retrieved from STN Database accession No. 2002:264464 abstract & Polymer, vol. 43, No. 12, 2002, pp. 3455-3468.

Database Caplus, Online Chemical Abstracts Service, Columbus, Ohio, US; Zhang, Yisheng et al: "Tetranuclear Hexanuclear and Octanuclear Copper (II) Complexes of a Series of Novel Dendritic Poly(phthalazine) Ligands" XP002333849 retrieved from STN Database accession No. 1995:875232 abstract & Inorganic Chemistry, vol. 34. No. 23, 1995. pp. 5870-5877.

Database Caplus. Online Chemical Abstracts Service. Columbus, Ohio, US; Kobayashi, Nagao et al: "Optically active phthalocyanines and their circular dichroism" XP002333850 retrieved from STN Database accession No. 1993:652129 abstract & Journal of the American Chemical Society, vol. 115, No. 23, 1993, pp. 10994-10995.

Database Caplus, Online Chemical Abstracts Service. Columbus, Ohio, US; Keller, Teddy M. et al: "Synthesis of phthalonitriles by nitro displacement" XP002333851 retrieved from STN Database accession No. 1981:442589 abstract & Synthesis, No. 8, 1980, p. 613.

Database Caplus, Online Chemical Abstracts Service, Columbus, Ohio, US; Dann, Otto et al: "Syntheses of biscationi, trypanocidal 1-benzofuran compounds" XP002333852 retrieved from STN Database accession No. 1983:53580 abstract & Liebigs Annalen Der Chemie. No. 10, 1982. p. 1836.

Co-pending commonly assigned, U.S. Appl. No. 11/415,935, filed May 2, 2006 now published as 2006-0252796A12 on Nov. 9, 2006.

Co-pending commonly assigned, U.S. Appl. No. 11/175,097, filed Jul. 5, 2006 now published as 2006-0009427A1 on Jan. 12, 2006.

Co-pending commonly assigned, U.S. Appl. No. 11/572,760, filed Aug. 8, 2005.

Co-pending commonly assigned. U.S. Appl. No. 11/572,743, filed Aug. 5, 2005.

Co-pending commonly assigned. U.S. Appl. No. 10/599,719, filed Apr. 14, 2005.

Co-pending commonly assigned, U.S. Appl. No. 60/706,413 5 filed Aug. 5, 2005.

Co-pending commonly assigned, U.S. Appl. No. 11/572,748, filed Aug. 22, 2005.

Abstract:: Arnold, Donald R. et al., Radical ions in photochemistry. Part 20. The photochemical nucleophile-olefin combination, aromatic substitution reaction. Canadian Journal of Chemistry (1988) 66 (12), 3012-26.

Gregorio Asensio et al., Synthesis of an enantiopure 2-arylcyclohexanols form prochiral enol acetates by an enantioselective protonation/diasteroselective reduction sequence, Tetrahedron: Asymmetry 14(2003) 3851-3855.

Alexandre Alexakis et al., Enantioselective Nucleophilic Opening fo meso Epoxides by Organolithium Reagents, Synlett Oct. 1998, pp. 1165-1167.

Shankar M. Shingh et al., Androgen Receptor Antagonists (Antiandrogens): Structure-Activity Relationships, Current Medicinal Chemistry, 2000, 7, 211-247.

Derwent English Abstract of German Patent Application (DE3939116AI).

Micropatent English Abstract of Japanese Patent (JP2001-247411).

Bohl, Casey E., et al, Structural basis for antagonism and resistance of bicalutamide in prostate cancer, PNAS, Apr. 26, 2005, vol. 102, No. 17 pp. 6201-6206.

Palucki. M. et al., "Palladium-catalyzed intermolecular carbon-oxygen bond formation; A new sysnthesis of aryl ethers".. J. Am. Chem. Soc., 1997. vol. 119, nr. 14. pp. 3395-3396.

Related Co Pending U.S. Appl. No. 11/053,010.

Database CA [Online] Chemical Abstracts Service, Columbus, Ohio, US; Yasuda, Kosuke et al: "Preparation of aliphatic nitrogenous five-membered ring compounds as dipeptidyl peptidase IV inhibitors" XP002350473 retrived from STN Database accession No. 136:325560.

Database CA [Online] Chemical Abstracts Service, Columbus, Ohio, US: Chaki, Hisaaki et al: "Preparation and formulation of alkylsulfonylbiphenyl and aminosulfonylbiphenyl derivatives as selective COX-2 inhibitors" XP002350472 retrieved from STN Database accession No. 125:300608.

Patent Abstracts of Japan vol. 013, No. 021 (C-560), Jan. 18, 1989 & JP 63227502A (SDS Biotech KK), Sep. 21, 1988.

Reiling B A et al: "Effect of prenatal androgenization on performance, lactation, carcass, and sensory traits of heifers in a single-calf heifer system" Journal of Animal Science, vol. 73, No. 4, 1995, pp. 986-992, XP0088065209 ISSN: 0021-8812.

Heitzman R J: "The effectiveness of anabolic agents in increasing rate of growth in farm animals; report on experiments in cattle." Environmental Quality and Safety. Supplement, 1976, No. 5, 1976, pp. 89-98, XP008065222 ISSN: 0340-4714.

Botzki, Salmen: "Structure based design . . . " Cominatorial Science, vol. 24, No. 4, 2005, pp. 458-469, XP008065218.

Loeffler L J et al: "Synthesis of Isosteres of P-Amidinophenylpyruvic Acid Inhibitors of Trypsin, Thrombin, and Pancreatic Kallikrein" Mar. 1, 1975 J. Of Med Chem, Amer. Chem. Soc. Wash. pp. 287-292 XP000574801 ISSN: 0022-2623.

Kuwabe, S., et al., "Palladium-Catalized Intramolecular C-O Bond Formation", *J. Am. Chem. Soc.*, vol. 123, pp. 12202-12206 (2001).

Co-pending commonly assigned. U.S. Appl. No. 11/572,760, filed Aug. 8, 2005.

Co-pending commonly assigned. U.S. Appl. No. 11/572,743, filed Aug. 5, 2005, now published as 2008-0064745A1, on Mar. 13, 2008.

Co-pending commonly assigned. U.S. Appl. No. 11/572,748, filed Aug. 22, 2005, now published as 2007-0207987A1, on Sep. 6, 2007.

Co-pending commonly assigned. U.S. Appl. No. 11/175,097, filed Jul. 5, 2005, now published as 2006-0009427A1 on Jan. 12, 2006.

Co-pending commonly assigned. U.S. Appl. No. 10/599,719, filed Apr. 14, 2005, now published as 2007-0197642A1, on Aug. 23, 2007.

Co-pending commonly assigned. U.S. Appl. No. 11/997,983, filed Jul. 27, 2006.

Co-pending commonly assigned. U.S. Appl. No. 11/415,935, filed May 2, 2006, now published as 2006-0252796A1, on Nov. 9, 2006.

Co-pending commonly assigned. U.S. Appl. No. 11/557,225, filed Nov. 7, 2006, now published as 2007-0072936A1, on Mar. 29, 2007.

Qian, et al., *J. Chem. Tech. Biotechnol.*, vol. 67, pp. 124-130 (1996).

Wagner, et al., *Tetrahedron Letters*, vol. 43, pp. 3569-3571 (2002).

* cited by examiner

ANDROGEN MODULATORS

CROSS REFERENCE TO RELATED APPLICATION

This application is a submission under 35 U.S.C. 371 of PCT/IB2005/000872 filed on Apr. 1, 2005, which claims priority to U. S. Provisional Application No. 60/561,812, filed on Apr. 13, 2004.

FIELD OF THE INVENTION

The present invention is directed to a new class of 4-cyano-phenoxy-alkyl carboxyl derivatives and to their use as androgen receptor modulators. Other aspects of the invention are directed to the use of these compounds to decrease sebum secretion and to stimulate hair growth.

BACKGROUND OF THE INVENTION

Alopecia, or balding, is a common problem which medical science has yet to cure. While androgens are associated with balding, the physiological mechanism by which this hair loss occurs is not known. However, it is known that hair growth is altered in individuals afflicted with alopecia.

Hair does not grow continuously but undergoes cycles of activity involving periods of growth, rest, and shedding. The human scalp typically contains from 100,000 to 350,000 hair fibers or shafts, which undergo metamorphosis in three distinct stages:

(a) during the growth phase (anagen) the follicle (i.e. the hair root) penetrates deep into the dermis with the cells of the follicle dividing rapidly and differentiating in the process of synthesizing keratin, the predominant component of hair. In non-balding humans, this growth phase lasts from one to five years;

(b) the transitional phase (catagen) is marked by the cessation of mitosis and lasts from two to three weeks; and (c) the resting phase (telogen) in which the hair is retained within the scalp for up to 12 weeks, until it is displaced by new follicular growth from the scalp below.

In humans, this growth cycle is not synchronized. An individual will have thousands of follicles in each of these three phases. However, most of the hair follicles will be in the anagen phase. In healthy young adults, the anagen to telogen ratio can be as high as 9 to 1. In individuals with alopecia, this ratio is reduced to as low as 2:1.

Androgenetic alopecia arises from activation of an inherited sensitivity to circulating androgenic hormones. It is the most common type of alopecia. It affects both men (50%) and women (30%), primarily of Caucasian origin. Gradual changes in the width and length of the hair shaft are experienced over time and with increasing age, prematurely in some. Terminal hair is gradually converted to short, wispy, colorless vellus hair. As a consequence, men in there 20's and women in their 30's and 40's begin to notice their hair becoming finer and shorter. In males, most of the hair loss occurs at the crown of the head. Females experience a thinning over their entire scalp. As discussed above, the anagen to telogen ratio is reduced significantly, resulting in less hair growth.

Minoxidil, a potassium channel opener, promotes hair growth. Minoxidil is available commercially in the United States under the trademark, Rogaine®. While the exact mechanism of action of minoxidil is unknown, its impact on the hair growth cycle is well documented. Minoxidil promotes the growth of the hair follicle and increase the period of time that the hair follicle is in the anagen phase (i.e. increases the anagen to telogn ratio).

While minoxidil promotes hair growth, the cosmetic efficacy of this growth can vary widely. For example, Roenigk reported the results of a clinical trial involving 83 males who used a topical solution of 3% minoxidil for a period of 19 months. Hair growth occurred in 55% of the subjects. However, only 20% of the subjects considered the growth to be cosmetically relevant. (*Clin. Res.,* 33, No. 4, 914A, 1985). Tosti reported cosmetically acceptable re-growth in 18.1% of his subjects. (*Dermatologica,* 173, No. 3, 136-138, 1986). Thus, the need exists in the art for compounds having the ability produce higher rates of cosmetically acceptable hair growth in patients with alopecia.

SUMMARY OF THE INVENTION

In accordance with the present invention, a new class of 4-cyano-phenoxy-alkyl carboxyl derivatives has been discovered. These compounds, their salts, solvates, and prodrugs thereof, may be represented by Formula I below:

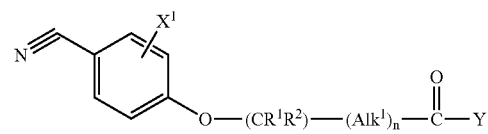

wherein;

a) $X^1$ is represented by cyano, halogen or haloalkyl, b) $R^1$ and $R^2$ are each independently represented by hydrogen or ($C_1$-$C_6$) alkyl, optionally substituted, c) $Alk^1$ is represented by a $C_1$-$C_2$ linear alkylene group, in which up to two hydrogen atoms are optionally replaced by a substitutent selected from the group consisting of $C_1$-$C_6$ alkyl optionally substituted, halogen, hydroxy, thiol, and cyano, d) n is represented by the integer 0 or 1, e) Y is represented by $NX^2X^3$ or O—$X^3$, f) $X^2$ is represented by hydrogen or ($C_1$-$C_6$) alkyl optionally substituted, g) $X^3$ is represented by, i) hydrogen, ii) ($C_1$-$C_{12}$)alkyl, optionally substituted, iii) ($C_2$-$C_{12}$)alkenyl, optionally substituted, iv) ($C_2$-$C_{12}$)alkynyl, optionally substituted, V) ($C_3$-$C_{10}$)cycloalkyl, optionally substituted, vi) ($C_3$-$C_{10}$) cycloalkyl($C_1$-$C_6$)alkyl, in which the alkyl and cycloalkyl moieties may each be optionally substituted, vii) ($C_6$-$C_{10}$)aryl, optionally substituted, viii) ($C_6$-$C_{10}$)aryl($C_1$-$C_6$)alkyl, in which the alkyl and aryl moieties may each be optionally substituted, ix) —$(CH_2)$-$(Alk^2)_q$-$C(O)R^3$, in which $Alk^2$ is represented by a ($C_1$-$C_8$) linear alkylene group, in which up to eight hydrogen atoms may optionally be replaced by a substitutent, selected from the group consisting of ($C_1$-$C_6$) alkyl optionally substituted, ($C_1$-$C_6$) alkoxy, halogen, hydroxy, thiol, cyano, and $NR^8R^9$ in which $R^8$ and $R^9$ are each independently represented by hydrogen or ($C_1$-$C_6$) alkyl, q is the integer 0 or 1, $R^3$ is represented by hydrogen, ($C_1$-$C_{12}$)alkyl, ($C_6$-

$C_{10}$)aryl, or ($C_6$-$C_{10}$)aryl($C_1$-$C_6$)alkyl, in which the alkyl and aryl moieties may each be optionally substituted, x) —($CH_2$)-($Alk^2$)$_q$-C(O)—O—$R^4$, in which $Alk^2$ and q, are as defined above, and $R^4$ is represented by hydrogen, ($C_1$-$C_{12}$)alkyl, ($C_6$-$C_{10}$)aryl, or ($C_6$-$C_{10}$)aryl($C_1$-$C_6$)alkyl, in which the alkyl and aryl moieties may be optionally substituted, xi) —($CH_2$)-($Alk^2$)$_q$-C(O)—$NR^5R^6$ in which $Alk^2$ and q are as described above, and $R^5$ and $R^6$ are each independently represented by hydrogen, ($C_1$-$C_{12}$)alkyl, ($C_6$-$C_{10}$)aryl, or ($C_6$-$C_{10}$)aryl($C_1$-$C_6$)alkyl, in which the alkyl and aryl moieties may be optionally substituted, xii) —($CH_2$)-($Alk^2$)$_q$-Y—$R^7$, in which $Alk^2$ and q are as defined above, Y is O or S, and $R^7$ is selected from the group consisting of hydrogen, ($C_1$-$C_{12}$)alkyl, ($C_6$-$C_{10}$)aryl, or ($C_6$-$C_{10}$)aryl($C_1$-$C_6$)alkyl, in which the alkyl and aryl moieties may be optionally substituted, xiii) heteroaryl, optionally substituted, xiv) heteroaryl($C_1$-$C_6$)alkyl, in which the heteroaryl and alkyl moieties may each be optionally substituted, xv) heterocyclic, optionally substituted, xvi) heterocyclic($C_1$-$C_6$)alkyl, in which the alkyl and heterocyclic moieties may each be substituted, or, h) for those compounds in which Y is N, $X^2$ and $X^3$, together with the adjacent nitrogen atom, may form a heterocyclic ring, which may optionally be substituted.

The compounds of Formula I are androgen receptor modulators. The compounds have affinity for the androgen receptor and will cause a biological effect by binding to the receptor. Typically, the compounds will act as antagonists. In selected embodiments they will act as partial agonists, full agonists, or tissue selective agonists. As androgen receptor modulators, the compounds can be used to treat, or alleviate, conditions associated with inappropriate activation of the androgen receptor. Examples of such conditions for antagonists include, but are not limited to, acne, excess sebum secretion, androgenic alopecia, hormone dependant cancers such as prostrate cancer, and hirsutism. Those compounds that are partial agonists, or full agonists, can be used to treat osteoporosis, hypogonadism, anemia, or to stimulate increases in muscle mass, especially in wasting diseases.

The invention is also directed to pharmaceutical compositions containing at least one of the compounds, in an amount effective to modulate activation of the androgen receptor. In a further embodiment, the invention is directed to an article of manufacture containing at least one of the compounds packaged for retail distribution, in association with instructions advising the consumer on how to use the compound to alleviate a condition associated with inappropriate activation of the androgen receptor. An additional embodiment is directed to the use of a compound as a diagnostic agent to detect inappropriate activation of the androgen receptor.

In a further embodiment, the compounds are used topically to induce and/or stimulate hair growth and/or to slow down hair loss. The compounds may also be used topically in the treatment of excess sebum and/or of acne.

DETAILED DESCRIPTION OF THE INVENTION

The headings within this document are only being utilized expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "halogen" refers to a chlorine, fluorine or bromine atom.

b. "$C_1$-$C_6$ alkyl" refers to a branched or straight chained alkyl group containing from 1 to 6 carbon atoms, such as methyl, ethyl, n-propyl, isopropyl, n-butyl, isobutyl, pentyl, etc.

c. "$C_1$-$C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 6hydrogen atoms are replaced by a substitutent selected from the group consisting of halogen, hydroxy, thiol, cyano, and $NR^8R^9$, in which $R^8$ and $R^9$ are each independently represented by hydrogen or ($C_1$-$C_6$) alkyl.

d. "haloalkyl" refers to a branched or straight chained alkyl group containing from 1 to 6 carbon atoms, in which at least one hydrogen atom is replaced with a halogen (i.e. $C_1$-$C_6$ haloalkyl). Examples of suitable haloalkyl's include chloromethyl, difluoromethyl, trifluoromethyl, 1-fluro-2-chloro-ethyl, 5-fluoro-hexyl, 3-difluro-isopropyl, 3-chloro-isobutyl, etc.

e. "linear alkylene group containing from 1 to 2 carbon atoms" (i.e. "$C_1$-$C_2$ linear alkylene group") refers to an alkyene group containing 1 or 2 carbon atoms and serving as a linking group within the molecule (i.e. no terminal —$CH_3$ function). Examples of such alkyl groups include —$CH_2$—, or —$CH_2$—$CH_2$—.

f. "linear alkylene group containing from 1 to 8 carbon atoms" (i.e. "$C_1$-$C_8$ linear alkylene group") refers to an alky group containing from 1to 8 carbon atoms serving as a linking group within the molecule (i.e. no terminal —$CH_3$ function). Examples of such alkyl groups include —$CH_2$—, —$CH_2$—($CH_2$)$_4$—$CH_2$—, —$CH_2$—($CH_2$)$_6$—$CH_2$, —$CH_2$—$CH_2$—$CH_2$—, —$CH_2$—($CH_2$)$_2$—$CH_2$—, etc.

g. "($C_1$-$C_2$)alkyl substituted with one or more halogen atoms" refers to a straight chained alkyl group containing 1 or 2 carbon atoms, i.e., methyl or ethyl in which at least one hydrogen atom is replaced with a halogen (i.e. for example trifluoromethyl, dichloromethyl, etc.).

h. "($C_1$-$C_2$)alkoxy substituted with one or more halogen atoms" refers to a straight chained alkoxy group containing 1 or 2 carbon atoms, i.e., methoxy or ethoxy in which at least one hydrogen atom is replaced with a halogen (i.e. for example trifluoromethoxy, difluoromethoxy, etc.)

i. "heteroatom" includes oxygen, nitrogen, and sulfur.

j. "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc.

k. "$C_1$-$C_{12}$ alkyl" refers to a branched or straight chained alkyl group containing from 1 to 12 carbon atoms, such as methyl, ethyl, n-propyl, isopropyl, n-butyl, isobutyl, hexyl, octyl, decyl, etc. Such an alkyl group may be optionally substituted, in which up to 8 hydrogen atoms are replaced by a substitutent selected from the group consisting of halogen, haloalkyl, hydroxy, thiol, cyano, and —$NR^8R^9$, in which $R^8$ and $R^9$ are as defined above.

l. "$C_2$-$C_{12}$ alkenyl" refers to a straight-chain or branched-chain hydrocarbon radical containing from 2 to 12 carbon atoms and 1, or more, carbon-carbon double bonds.

Examples of alkenyl radicals include ethenyl, propenyl, 1,4-butadienyl, 1-hexenyl, 1,3-octadienyl and the like. Such an alkenyl group may be optionally substituted, in which up to 8 hydrogen atoms are replaced by a substituent selected from the group consisting of halogen, haloalkyl, hydroxy, thiol, cyano, and —$NR^8R^9$, in which $R^8$ and $R^9$ are as defined above.

m. "$C_2$-$C_{12}$ alkynyl" refers to a straight-chain or branched-chain hydrocarbon radical containing from 2 to 12 carbon atoms and having 1, or more, carbon-carbon triple bonds. Examples of alkynyl radicals include ethynyl, propynyl, butynyl, octynyl, and the like. Such an alkynyl group may be optionally substituted, in which up to 8 hydrogen atoms are replaced by a substituent selected from the group consisting of halogen, hydroxy, haloalkyl, thiol, cyano, and —$NR^8R^9$, in which $R^8$ and $R^9$ are as defined above.

n. "($C_6$-$C_{10}$)aryl" means a cyclic, aromatic hydrocarbon containing from 6 to 10 carbon atoms. Examples of aryl groups include phenyl, naphthyl and biphenyl. Such an aryl moiety may be optionally substituted with up to 4 non-hydrogen substituents, each substituent is independently selected from the group consisting of halogen, cyano, hydroxy, ($C_1$-$C_6$)alkyl, ($C_1$-$C_6$)alkoxy, ($C_1$-$C_2$)alkyl substituted with one or more halogens, ($C_1$-$C_2$) alkoxy substituted with one or more halogens, $SR^8$ and $NR^8R^9$. $R^8$ and $R^9$ are each independently represented by $C_1$-$C_6$ alkyl or hydrogen. These substituents may be the same or different and may be located at any position of the ring, that is chemically permissible.

o. "heteroaryl" refers to an aromatic ring having one, or more, heteroatoms selected from oxygen, nitrogen and sulfur. More specifically, it refers to a 5- or 6-, membered ring containing 1, 2, or 3 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. The 5-membered ring has 2 double bonds and the 6-membered ring has 3 double bonds. The term heteroaryl also includes bicyclic groups in which the heteroaryl ring is fused to a benzene ring, heterocyclic ring, a cycloalkyl ring, or another heteroaryl ring. Examples of such heteroaryl ring systems include, but are not limited to, pyrrolyl, furanyl, thienyl, imidazolyl, oxazolyl, indolyl, thiazolyl, pyrazolyl, pyridinyl, pyrimidinyl, purinyl, quinolinyl, benzofuran and isoquinolinyl.

p. "heteroaryl, optionally substituted," refers to a heteroaryl moiety as defined immediately above, in which up to 4 carbon atoms of the heteroaryl moiety may be substituted with a substituent, each substituent is independently selected from the group consisting of halogen, cyano, hydroxy, ($C_1$-$C_6$)alkyl, ($C_1$-$C_6$)alkoxy, ($C_1$-$C_2$)alkyl substituted with one or more halogens, ($C_1$-$C_2$) alkoxy substituted with one or more halogens, $SR^8$, and $NR^8R^9$, in which $R^8$ and $R^9$ are as defined above.

q. "heterocycle" or "heterocyclic ring" refers to any 3- or 4-membered ring containing a heteroatom selected from oxygen, nitrogen and sulfur; or a 5-, 6-, 7-, 8-, 9-, or 10-membered ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, the 6- and 7-membered rings have 0 to 2 double bonds, and the 8, 9, or 10 membered rings may have 0, 1, 2, or 3 double bonds. The term "heterocyclic" also includes bicyclic groups in which any of the above heterocyclic rings is fused to a benzene ring, a cyclohexane or cyclopentane ring or another heterocyclic ring (for example, indolyl, quinolyl, isoquinolyl, tetrahydroquinolyl, benzofuryl, dihydrobenzofuryl or benzothienyl and the like). Heterocyclics include: pyrrolidinyl, tetrahydrofuranyl, tetrahydrothiophenyl, piperidinyl, piperazinyl, azepane, azocane, morpholinyl, isochroamyl and quinolinyl.

r. "heterocyclic, optionally substituted" refers to a heterocyclic moiety as defined immediately above, in which up to 4 carbon atoms of the heterocycle moiety may be substituted with a substituent, each substituent is independently selected from the group consisting of halogen, cyano, hydroxy, ($C_1$-$C_6$)alkyl, ($C_1$-$C_6$)alkoxy, ($C_1$-$C_2$)alkyl substituted with one or more halogens, ($C_1$-$C_2$) alkoxy substituted with one or more halogens, $SR^8$, and $NR^8R^9$, in which $R^8$ and $R^9$ are as defined above. Any nitrogen atom within such a heterocyclic ring may optionally be substituted with ($C_1$-$C_6$) alkyl, if such substitution is chemically permissible.

s. "$C_3$-$C_{10}$ cycloalkyl" refers to a saturated or partially saturated monocyclic, bicyclic or tricyclic alkyl radical wherein each cyclic moiety has 3 to 10 carbon atoms. Examples of cycloalkyl radicals include cyclopropyl, cyclobutyl, cyclopentyl, cyclohexyl, cyclooctyl, and the like. Such a cycloalkyl group may be optionally substituted, in which up to 4 hydrogen atoms are replaced by a substituent selected from the group consisting of halogen, cyano, hydroxy, ($C_1$-$C_6$)alkyl, ($C_1$-$C_6$)alkoxy, ($C_1$-$C_2$)alkyl substituted with one or more halogens, ($C_1$-$C_2$) alkoxy substituted with one or more halogens, $SR^8$, and $NR^8R^9$, in which $R^8$ and $R^9$ are as defined above.

t. "androgen" refers to testosterone and its precursors and metabolites, and 5-alpha reduced androgens, including but not limited to dihydrotestosterone. Androgen refers to androgens from the testis, adrenal gland, and ovaries, as well as all forms of natural, synthetic and substituted or modified androgens.

u. "pharmaceutically acceptable" means suitable for use in mammals.

v. "salts" is intended to refer pharmaceutically acceptable salts and to salts suitable for use industrial processes, such as the preparation of the compound.

w. "pharmaceutically acceptable salts" is intended to refer to either pharmaceutically acceptable acid addition salts" or "pharmaceutically acceptable basic addition salts" depending upon actual structure of the compound.

x. "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

y. "pharmaceutically acceptable basic addition salts" is intended to apply to any non-toxic organic or inorganic basic addition salts of the compounds represented by Formula I, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

z. "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

aa. "compound of Formula I", "compounds of the invention", and "compounds" are used interchangeably throughout the application and should be treated as synonyms.

bb. "patient" refers to warm blooded animals such as, for example, guinea pigs, mice, rats, gerbils, cats, rabbits, dogs, monkeys, chimpanzees, and humans.

cc. "treat" refers to the ability of the compounds to either relieve, alleviate, or slow the progression of the patient's disease (or condition) or any tissue damage associated with the disease.

Some of the compounds of Formula I will exist as optical isomers. Any reference in this application to one of the compounds represented by Formula I is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively utilization of a specific optical isomer as the starting material will produce the corresponding isomer as the final product.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

All of the compounds of Formula I contain a phenyl ring. To further exemplify the invention, the numbering system for this ring and its substitution pattern is shown below:

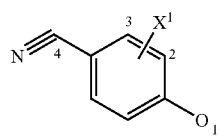

Position 4 of this phenyl ring is substituted with a cyano moiety as depicted above. Position 1 is substituted with an oxygen atom forming an ether moiety. The phenyl ring will be further substituted, as depicted by $X^1$, at position 2 or 3, with a halogen atom a haloalkyl moiety, or a cyano function. Typically, this halogen, cyano or haloalkyl moiety will be at the 3-position. More typically it will be trifluoromethyl located at the 3-position of the phenyl ring.

As noted above, position 1 of the phenyl ring is substituted with the ether moiety, $-CR^1R^2-(Alk^1)_n-C(O)-Y$. Typically, one of $R^1$ or $R^2$ will be represented by $C_1-C_6$ alkyl, which may be optionally substituted. The other of $R^1$ or $R^2$ may be represented by hydrogen or $C_1-C_6$ alkyl, optionally substituted. More typically, one of $R^1$ or $R^2$ is unsubstituted $C_1-C_6$ alkyl, and the other is a hydrogen atom. More typically one of $R^1$ or $R^2$ is isobutyl, or n-propyl, and the other is a hydrogen atom.

$Alk^1$, when present, will be represented by a methylene or ethylene-bridging group. Up to two hydrogen atoms of this alkylene bridging group may be replaced with one of the substitutents defined above. Any single carbon atom of $Alk^1$ may be unsubstituted, monosubstituted, or disubstituted. These carbon atoms may be substituted with the same substitutent or differing substitutents. Typically, $Alk^1$ will be absent.

Y, along with the adjacent carbonyl group, may form an amide, an ester, a carboxylic acid, or a carboxylate anion. Typically, Y is a nitrogen atom. $X^2$ and $X^3$ may each be represented by one of the substitutents listed above. Alternatively, $X^2$ and $X^3$ along with the nitrogen atom may form a heterocyclic ring, which may be further substituted as described above.

More specific embodiments of the invention include those compound in which:

$X^1$ is represented by $CF_3$ and is located at the 3-position of the phenyl ring, $R^1$ is isobutyl or propyl, $R^2$ is hydrogen, n is 0, Y is represented by $-NX^2X^3$;

$X^1$ is represented by $CF_3$ and is located at the 3-position of the phenyl ring, $R^1$ is isobutyl or propyl, $R^2$ is hydrogen, n is 0, Y is represented by O, $X^1$ is represented by $CF_3$ and is located at the 3-position of the phenyl ring, $R^1$ is isobutyl, $R^2$ is hydrogen, n is 0, Y is represented by $-NX^2X^3$ in which $X^2$ is represented by hydrogen and $X^3$ is as defined above, $X^1$ is represented by $CF_3$ and is located at the 3-position of the phenyl ring, $R^1$ is isobutyl, $R^2$ is hydrogen, n is 0, Y is represented by $-NX^2X^3$ in which $X^2$ is represented by hydrogen and $X^3$ is $(C_6-C_{10})aryl(C_1-C_6alky)$, in which the aryl moiety is phenyl, and the alkyl moiety is methyl, or ethyl;

$X^1$ is represented by $CF_3$ and is located at the 3-position of the phenyl ring, $R^1$ is isobutyl or propyl, $R^2$ is hydrogen, n is 0, Y is represented by $-NX^2X^3$ in which $X^2$ is represented by hydrogen and $X^3$ is $(C_6-C_{10})aryl(C_1-C_6alky)$, in which the aryl moiety is phenyl, optionally substituted with at least one substitutent selected from the group consisting of methoxy, ethoxy, hydroxy, methyl, and the alkyl moiety is methyl or ethyl;

$X^1$ is represented by $CF_3$ and is located at the 3-position of the phenyl ring, $R^1$ is isobutyl or propyl, $R^2$ is hydrogen, n is 0, Y is represented by $-NX^2X^3$ in which $X^2$ is represented by hydrogen and $X^3$ is $C_1-C_{12}$ alkyl, more specifically isopropyl, isobutyl;

$X^1$ is represented by $CF_3$ and is located at the 3-position of the phenyl ring, $R^1$ is isobutyl or propyl, $R^2$ is hydrogen, n is 0, Y is represented by $-NX^2X^3$ in which $X^2$ is represented by hydrogen and $X^3$ is heteroaryl($C_1$-$C_6$alky), in which the heteroaryl moiety is optionally substituted, and the alkyl moiety is methyl or ethyl;

$X^1$ is represented by $CF_3$ and is located at the 3-position of the phenyl ring, $R^1$ is isobutyl or propyl, $R^2$ is hydrogen, n is 0, Y is represented by —$NX^2X^3$ in which $X^2$ is represented by hydrogen and $X^3$ is heteroaryl($C_1$-$C_6$alky), in which the heteroaryl moiety is pyridine, furan, thiophene, indolyl, and the alkyl moiety is methyl or ethyl;

$X^1$ is represented by $CF_3$ and is located at the 3-position of the phenyl ring, $R^1$ is isobutyl or propyl, $R^2$ is hydrogen, n is 0, Y is represented by —$NX^2X^3$ in which $X^2$ is represented by hydrogen and $X^3$ is ($C_3$-$C_{10}$)cycloalkyl($C_1$-$C_6$alky).

More specific examples of compounds encompassed by Formula I include:
a) 2-(4-cyano-3-trifluoromethyl-phenoxy)-4-methyl-pentanoic acid,
b) 2-(4-cyano-3-trifluoromethyl-phenoxy)-4-methyl-pentanoic acid benzylamide,
c) 2-(4-cyano-3-trifluoromethyl-phenoxy)-pentanoic acid,
d) 2-(4-cyano-3-chloro-phenoxy)-pentanoic acid,
e) 2-(4-cyano-3-trifluoromethyl-phenoxy)-4-methyl-pentanoic acid isopropylamide,
f) 2-(4-cyano-3-trifluoromethyl-phenoxy)-4-methyl-pentanoic acid ethylamide,
g) 2-(4-cyano-3-trifluoromethyl-phenoxy)-pentanoic acid benzylamide,
h) 2-(4-cyano-3-fluoro-phenoxy)-hexanoic acid benzylamide,
i) 2-(4-cyano-3-trifluoromethyl-phenoxy)-pentanoic acid ethylamide,
j) 2-(4-cyano-3-trifluoromethyl-phenoxy)-pentanoic acid [1-(4-hydroxyphenyl)-ethyl]-amide,
k) 2-(4-cyano-3-trifluoromethyl-phenoxy)-4-methyl-pentanoic acid cyclopropylmethyl-amide,
l) 2-(4-cyano-3-trifluoromethyl-phenoxy)-4-methyl-pentanoic acid cyclohexylmethyl-amide,
m) 2-(4-cyano-3-trifluoromethyl-phenoxy)-4-methyl-pentanoic acid cyclopropylethyl-amide,
n) 2-(4-cyano-3-trifluoromethyl-phenoxy)-4-methyl-pentanoic acid cyclohexylethyl-amide,
o) 2-(4-cyano-3-trifluoromethyl-phenoxy)-4-methyl-pentanoic acid isobutyl-amide,
p) 2-(4-cyano-3-trifluoromethyl-phenoxy)-4-methyl-pentanoic acid hexylamide,
q) 2-(4-cyano-3-trifluoromethyl-phenoxy)-4-methyl-pentanoic acid [2-(4-methoxy-phenyl)-ethyl]-amide,
r) 2-(4-cyano-3-trifluoromethyl-phenoxy)-4-methyl-pentanoic acid [2-(4-fluoro-phenyl)-ethyl]-amide,
s) 2-(4-cyano-3-trifluoromethyl-phenoxy)-4-methyl-pentanoic acid (2-phenoxy-ethyl)-amide,
t) 2-(4-cyano-3-trifluoromethyl-phenoxy)-4-methyl-pentanoic acid (furan-2-yl-methyl)-amide,
u) 2-(4-cyano-3-trifluoromethyl-phenoxy)-4-methyl-pentanoic acid (2-piperidino-methyl)-amide,
v) 2-(4-cyano-3-trifluoromethyl-phenoxy)-4-methyl-pentanoic acid (thiophen-2-yl-methyl)-amide,
w) 2-(4-cyano-3-trifluoromethyl-phenoxy)-4-methyl-pentanoic acid (pyrrol-2-yl-methyl)-amide,
x) 2-(4-cyano-3-trifluoromethyl-phenoxy)-4-methyl-pentanoic acid (1-thiophen-2-yl-ethyl)-amide,
y) 2-(4-cyano-3-trifluoromethyl-phenoxy)-4-methyl-pentanoic acid (1-methyl-2-thiophen-3-yl-ethyl)-amide,
z) 2-(4-cyano-3-trifluoromethyl-phenoxy)-4-methyl-pentanoic acid (1-pyridin-3-yl-ethyl)-amide,
aa) 2-(4-cyano-3-trifluoromethyl-phenoxy)-4-methyl-pentanoic acid (pyridin-4-yl-methyl)-amide,
bb) 2-(4-cyano-3-trifluoromethyl-phenoxy)-pentanoic acid (1-thiophen-2-yl-ethyl)-amide,
cc) 2-(4-cyano-3-trifluoromethyl-phenoxy)-pentanoic acid (1-methyl-2-thiophen-3-yl-ethyl)-amide,
dd) 2-(4-cyano-3-trifluoromethyl-phenoxy)-4-methyl-pentanoic acid (pyridin-3-yl-methyl)-amide,
ee) 2-(4-cyano-3-trifluoromethyl-phenoxy)-4-methyl-pentanoic acid (indol-3-yl-methyl)-amide,
ff) 2-(4-cyano-3-trifluoromethyl-phenoxy)-4-methyl-pentanoic acid (3-methyl-pyridin-2-yl-methyl)-amide,
gg) 2-(4-cyano-3-trifluoromethyl-phenoxy)-4-methyl-pentanoic acid (3-methylsulfanyl-propyl)-amide,
hh) 2-(4-cyano-3-trifluoromethyl-phenoxy)-4-methyl-pentanoic acid (3-benzyl-sulfanyl-propyl)-amide,
ii) 2-(4-cyano-3-trifluoromethyl-phenoxy)-4-methyl-pentanoic acid (3-methyl-butyl)-amide,
jj) 2-(4-cyano-3-trifluoromethyl-phenoxy)-4-methyl-pentanoic acid (3,3-diethoxy-propyl)-amide,
kk) 2-(4-cyano-3-trifluoromethyl-phenoxy)-4-methyl-pentanoic acid (benzo[1,3]dioxol-5-yl-methyl)-amide,
ll) 2-(4-cyano-3-trifluoromethyl-phenoxy)-4-methyl-pentanoic acid (2,3-dihydro-benzofuran-5-yl-methyl)-amide,
mm) 2-(4-cyano-3-trifluoromethyl-phenoxy)-4-methyl-pentanoic acid (benzo[1,2,5]thiadiazol-5-yl-methyl)-amide,
nn) 2-(4-cyano-3-trifluoromethyl-phenoxy)-4-methyl-pentanoic acid (isochroman-3-yl-methyl)-amide,
oo) 2-(4-cyano-3-trifluoromethyl-phenoxy)-4-methyl-pentanoic acid (3-methylsulfanyl-propyl)-amide,
pp) 2-(4-cyano-3-trifluoromethyl-phenoxy)-pentanoic acid (benzo[1,3]dioxol-5-yl-methyl)-amide,
qq) 2-(4-cyano-3-trifluoromethyl-phenoxy)-pentanoic acid (2,3-dihydro-benzofuran-5-yl-methyl)-amide,
rr) 2-(4-cyano-3-trifluoromethyl-phenoxy)-pentanoic acid (2,3-dihydro-benzofuran-2-yl-methyl)-amide,
ss) 2-(4-cyano-3-trifluoromethyl-phenoxy)-pentanoic acid (benzo[1,2,5]thiadiazo-5-yl-methyl)-amide,
tt) 2-(4-cyano-3-trifluoromethyl-phenoxy)-pentanoic acid (isochroman-3-yl-methyl)-amide,
uu) 2-(4-cyano-3-trifluoromethyl-phenoxy)-4-methyl-pentanoic acid-3-methoxy-benzylamide,
vv) 2-(4-cyano-3-trifluoromethyl-phenoxy)-4-methyl-pentanoic acid-3-methoxy-4-trufluoromethyl-benzylamide,
ww) 2-(4-cyano-3-trifluoromethyl-phenoxy)-4-methyl-pentanoic acid [2-(4-methoxy-phenyl)-ethyl]amide,
xx) 2-(4-cyano-3-trifluoromethyl-phenoxy)-4-methyl-pentanoic acid-2-methoxy-benzylamide,
yy) 2-(4-cyano-3-trifluoromethyl-phenoxy)-4-methyl-hexanoic acid-2-methoxy-benzylamide,
zz) 2-(4-cyano-3-trifluoromethyl-phenoxy)-4-methyl-pentanoic acid-2-ethoxy-benzylamide,
aaa) 2-(4-cyano-3-trifluoromethyl-phenoxy)-4-methyl-pentanoic acid-3-methyl-benzylamide,
bbb) 2-(4-cyano-3-trifluoromethyl-phenoxy)-4-methyl-pentanoic acid-2-methyl-benzylamide,
ccc) 2-(4-cyano-3-trifluoromethyl-phenoxy)-4-methyl-pentanoic acid-4-methoxy-benzylamide,
ddd) 2-(4-cyano-3-trifluoromethyl-phenoxy)-pentanoic acid-3-methoxy-benzylamide,
eee) 2-(4-cyano-3-trifluoromethyl-phenoxy)-pentanoic acid-2-methoxy-benzylamide,
fff) 2-(4-cyano-3-trifluoromethyl-phenoxy)-pentanoic acid-2-ethoxy-benzylamide,
ggg) 2-(4-cyano-3-trifluoromethyl-phenoxy)-pentanoic acid-3-methyl-benzylamide,
hhh) 2-(4-cyano-3-trifluoromethyl-phenoxy)-hexanoic acid-phenylhexyl amide, iii) 2-(4-cyano-3-trifluoromethyl-phenoxy)-pentanoic acid-2-methyl-benzylamide,
jjj) 2-(4-cyano-3-trifluoromethyl-phenoxy)-pentanoic acid-2,4-dimethyl-benzylamide,
kkk) 2-(4-cyano-3-trifluoromethyl-phenoxy)-pentanoic acid-4-methoxy-benzylamide,
lll) 2-(4-cyano-3-trifluoromethyl-phenoxy)-4-methyl-pentanoic acid-(2-p-tolyl-ethyl)-amide,
mmm) 2-(4-cyano-3-trifluoromethyl-phenoxy)-4-methyl-pentanoic acid-[2-(2-methoxy-phenyl)-ethyl]-amide,
nnn) 2-(4-cyano-3-trifluoromethyl-phenoxy)-4-methyl-pentanoic acid-(2-m-tolyl-ethyl)-amide,
ooo) 2-(4-cyano-3-trifluoromethyl-phenoxy)-pentanoic acid-(2-p-tolyl-ethyl)amide,
ppp) 2-(4-cyano-3-trifluoromethyl-phenoxy)-pentanoic acid-[2-(2-methoxyphenyl)-ethyl]-amide,
qqq) 2-(4-cyano-3-trifluoromethyl-phenoxy)-pentanoic acid-(2-m-tolyl-ethyl)amide,
rrr) 2-(4-cyano-3-trifluoromethyl-phenoxy)-4-methyl-pentanoic acid-(2-phenoxy-propyl)-amide,
sss) 2-(4-cyano-3-trifluoromethyl-phenoxy)-4-methyl-pentanoic acid-(phenoxy-hexyl)-amide,
ttt) 2-(4-cyano-3-trifluoromethyl-phenoxy)-4-methyl-pentanoic acid indan-1-yl-amide,
uuu) 2-(4-cyano-3-trifluoromethyl-phenoxy)-pentanoic acid-(2-phenoxypropyl)-amide,
vvv) 2-(4-cyano-3-trifluoromethyl-phenoxy)-pentanoic acid-(2-phenoxyethyl)-amide,
www) 2-(4-cyano-3-trifluoromethyl-phenoxy)-pentanoic acid indan-1-yl-amide,
xxx) 2-(4-cyano-3-trifluoromethyl-phenoxy)-4-methyl-pentanoic acid-[2-(3-methoxy-phenyl)-ethyl]-amide,
yyy) 2-(4-cyano-3-trifluoromethyl-phenoxy)-4-methyl-pentanoic acid [2-(1H-indol-3-yl)-ethyl]amide,
zzz) 2-(4-cyano-3-trifluoromethyl-phenoxy)-4-methyl-pentanoic acid (2H-imidazo[1,2-a]pyridin-3-yl)-methyl) amide,
aaaa) 2-(4-cyano-3-trifluoromethyl-phenoxy)-4-methyl-pentanoic acid-[2-(4-hydroxy-phenyl)-ethyl]-amide,
bbbb) 2-(4-cyano-3-trifluoromethyl-phenoxy)-4-methyl-pentanoic acid-(3-pyridin-3-yl-propyl)-amide,
cccc) 2-(4-cyano-3-trifluoromethyl-phenoxy)-4-methyl-pentanoic acid benzyl-isopropyl-amide,
dddd) 2-(4-cyano-3-trifluoromethyl-phenoxy)-4-methyl-pentanoic acid benzyl-methyl-amide,
eeee) 2-(4-cyano-3-trifluoromethyl-phenoxy)-4-methyl-pentanoic acid benzyl-1-hydroxy-pentyl-amide,
ffff) 2-(4-cyano-3-trifluoromethyl-phenoxy)-pentanoic acid-[2-(3-methoxyphenyl)-ethyl]-amide,
gggg) 2-(4-cyano-3-trifluoromethyl-phenoxy)-pentanoic acid [2-(1H-indol-3-yl)-ethyl]amide,
hhhh) 2-(4-cyano-3-trifluoromethyl-phenoxy)-pentanoic acid-[2-(4-hydroxyphenyl)-ethyl]-amide,
iiii) 2-(4-cyano-3-trifluoromethyl-phenoxy)-pentanoic acid benzyl-isopropyl-amide,
jjjj) 2-(4-cyano-3-trifluoromethyl-phenoxy)-4-methyl-pentanoic acid (2-dimethylamino-2-phenyl-ethyl)-amide,
kkkk) 2-(4-cyano-3-trifluoromethyl-phenoxy)-4-methyl-pentanoic acid [1-(4-hydroxy-phenyl)-ethyl]-amide,
llll) 2-(4-cyano-3-trifluoromethyl-phenoxy)-4-methyl-pentanoic acid 4-isopropyl-benzylamide,
mmmm) 2-(4-cyano-3-trifluoromethyl-phenoxy)-4-methyl-pentanoic acid-3-methoxy-benzylamide,
nnnn) 2-(4-cyano-3-trifluoromethyl-phenoxy)-4-methyl-pentanoic acid-(6-methoxy-pyridin-3-yl-methyl)-amide,
oooo) 2-(4-cyano-3-trifluoromethyl-phenoxy)-4-methyl-pentanoic acid-4-methoxy-benzylamide,
pppp) 2-(4-cyano-3-trifluoromethyl-phenoxy)-4-methyl-pentanoic acid-3,4-dihydroxy-benzylamide,
qqqq) 2-(4-cyano-3-trifluoromethyl-phenoxy)-4-methyl-pentanoic acid-(2-methyl-butyl)-amide,
rrrr) 2-(4-cyano-3-trifluoromethyl-phenoxy)-4-methyl-pentanoic acid-piperidine-amide,
ssss) 2-(4-cyano-3-trifluoromethyl-phenoxy)-4-methyl-pentanoic acid-pyrrolidine-amide
tttt) 2-(4-cyano-3-trifluoromethyl-phenoxy)-4-methyl-pentanoic acid-pyrrolidine-amide
uuuu) 2-(4-cyano-3-trifluoromethyl-phenoxy)-4-methyl-pentanoic acid-piperazine-amide
vvvv) 2-(4-cyano-3-trifluoromethyl-phenoxy)-4-methyl-pentanoic acid (2-methyl-pyridin-3-yl-methyl)-amide,
wwww) 2-(4-cyano-3-trifluoromethyl-phenoxy)-pentanoic acid (naphthalene-1-yl-methyl)-amide,
xxxx) 2-(4-cyano-3-trifluoromethyl-phenoxy)-4-methyl-pentanoic acid (3-hydroxy-4-methyl-phenyl)-amide,
yyyy) 2-(4-cyano-3-trifluoromethyl-phenoxy)-4-methyl-pentanoic acid (2-hydroxy-ethyl)-isopropyl-amide,
zzzz) 2-(4-cano-3-trifluoromethyl-phenoxy)-4-methyl-pentanoic acid (3-methylsulfanyl-propyl)-amide,
aaaaa) 2-(4-Cyano-3-trifluoromethyl-phenoxy)-4-methyl-pentanoic acid (2-propoxy-ethyl)-amide,
bbbbb) 2-(4-cano-3-trifluoromethyl-phenoxy)-4-methyl-pentanoic acid (1-methoxymethyl-propyl)-amide,
ccccc) 2-(4-cyano-3-trifluoromethyl-phenoxy)-4-methyl-pentanoic acid (2-methylsulfanyl-ethyl)-amide,
ddddd) 2-(4-cyano-3-trifluoromethyl-phenoxy)-4-methyl-pentanoic acid (3-hydroxy-2-methyl-phenyl)-amide,
eeeee) 2-(4-cyano-3-trifluoromethyl-phenoxy)-4-methyl-pentanoic acid (3-propoxy-propyl)-amide,
fffff) 2-(4-cyano-3-trifluoromethyl-phenoxy)-4-methyl-pentanoic acid ethyl(2-methoxy-ethyl)-amide,
ggggg) 2-(4-cyano-3-trifluoromethyl-phenoxy)-4-methyl-pentanoic acid (2-methoxy-phenyl)-amide,
hhhhh) 2-(4-cyano-3-trifluoromethyl-phenoxy)-4-methyl-pentanoic acid (3-hydroxy-4-methyl-phenyl)-amide,
iiiii) 2-(4-cyano-3-trifluoromethyl-phenoxy)-pentanoic acid (3-methylsulfanyl-propyl)-amide,
jjjjj) 2-(4-cyano-3-trifluoromethyl-phenoxy)-pentanoic acid (2-methylsulfanyl-ethyl)-amide,
kkkkk) 2-(4-cyano-3-trifluoromethyl-phenoxy)-hexanoic acid benzylamide,
lllll) N-benzyl-2-(4-cyano-3-trifluoromethyl-phenoxy)-3-methyl-butyramide,
mmmmm) N-benzyl-2-(4-cyano-3-trifluoromethyl-phenoxy)-butyramide,
nnnnn) N-benzyl-2-(4-cyano-3-trifluoromethyl-phenoxy)-propylamide,
ooooo) (R)-2-(4-cyano-3-trifluoromethyl-phenoxy)-4-methyl-pentanoic acid benzylamide, and
ppppp) (R)-2-(4-cyano-3-trifluoromethyl-phenoxy)-pentanoic acid benzylamide.

Synthesis

The compounds of Formula I can be prepared by methods known in the art. One method for preparing these compounds is described below in Reaction Schemes I, II, and III. Reaction Scheme I describes the synthesis of a compound of Formula I in which Y is OH, i.e. a carboxylic acid. If desired, this acid may then be converted into an amide as described in Reaction Scheme II. Reaction Scheme III describes one method for converting the acid into an ester.

13

Reaction Scheme I—Free Acid

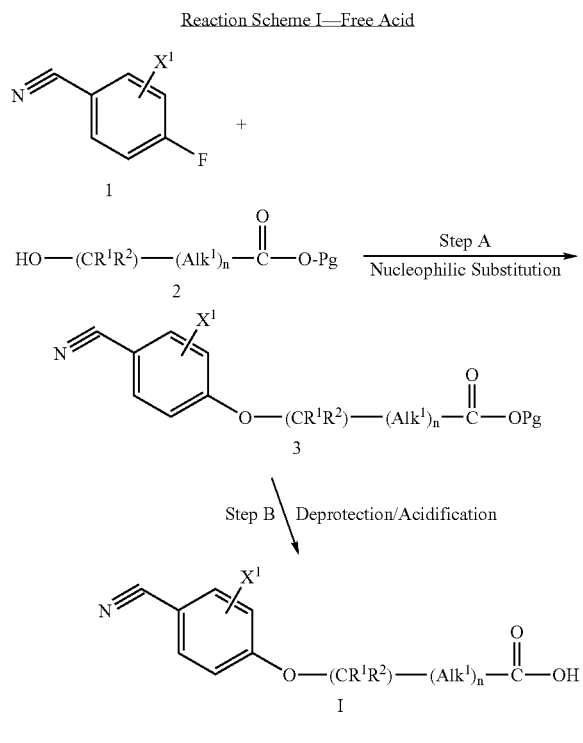

The initial step is to carry out a nucleophilic substitution reaction with a benzonitrile as described by structure 1 and an alcohol as described by structure 2. In the alcohol of structure of 2, $R^1$, $R^2$, and $Alk^1$ should be represented by the same substitutent as is desired in the final product. Pg represents a suitable protecting group. Examples of such protecting groups include isopropyl, benzyl, etc. The reader's attention is directed to T. W. Greene, *Protective Groups in Organic Synthesis*, John Wiley & Sons, New York, 1991, for further suggestions regarding suitable protecting groups. The alcohols of structure 2 are known in the art can be prepared as described in *Tetrahedron Letters*, 1998, 29(20), 2453-2454.

The other starting material is a 4-fluoro-benzonitrile as depicted by structure 1. $X^1$ should be represented by the same substitutent as is desired in the final product. These benzonitriles are known in the art and may be synthesized as described by Japanese Patent Application Number 01097937.

The nucleophilic substitution depicted above may be carried out as is known in the art. The alcohol of structure 2 is contacted with a slight excess of a base, such as sodium hydride, to produce an alkoxide ion. The reaction is carried out in an aprotic solvent, such as tetrahydrofuran, under an inert atmosphere (typically nitrogen) at a temperature of about 0° C. The alcohol is stirred with the base for a period of time ranging from 5 to 60 minutes.

One equivalent of the 4-fluoro-benzonitrile of structure 1 is then added to the reaction and the reactants are stirred for a sufficient period of time to allow the alkoxide ion to displace the fluorine from the benzonitrile. This typically takes from 30 minutes to 24 hours. The reaction is typically allowed to warm to room temperature.

The resulting product, a compound of structure 3, can be recovered by extraction, evaporation, or other techniques known in the art. It may then optionally be purified by chromatography, recrystallization, distillation, or other techniques known in the art. Alternatively, the compound of structure 3 may be utilized directly in the deprotection reaction described above, without subsequent recovery or purification.

The deprotection reaction is carried out as is known in the art. The compound of structure 3 is contacted with an excess of a weak base, such as lithium hydroxide, in a solvent such as an admixture of tetrahydrofuran and water. The reactants are heated to reflux for a sufficient period of time to remove the protecting group, which is typically accomplished in a period of time ranging from 5 minutes to 24 hours. The reaction is then cooled and the free acid is generated introducing a strong acid into the reaction, such as hydrochloric acid, sulfuric acid, etc. The desired compound of Formula I, in which Y is OH, can be recovered by extraction, evaporation, or other techniques known in the art. It may then optionally be purified by chromatography, recrystallization, distillation, or other techniques known in the art.

If the desired compound of Formula I is an amide (i.e. Y is $NX^2X^3$), then it may be generated as depicted in Reaction Scheme II:

Reaction Scheme II—Amidation

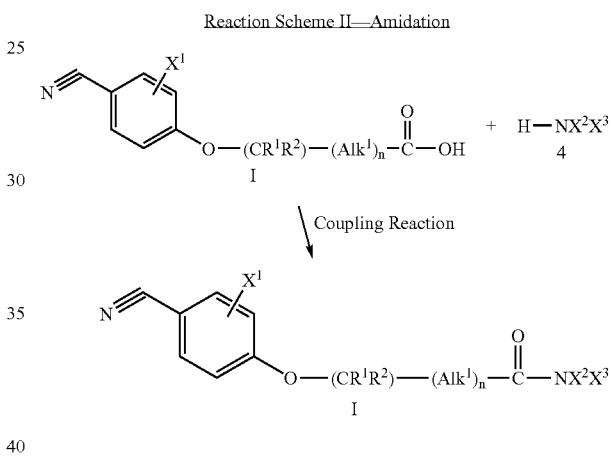

The free acid of Formula I may be converted to an amide using a coupling reaction as is known in the art. One of the reactants is the amine as described by structure 4. $X^2$ and $X^3$ will be represented by the same substitutent as desired in the final product of Formula I. These amines are known in the art and can be prepared as described in *Journal of the American Chemical Society* (1927), 49, 2908-2914.

The coupling reaction may be carried out as is known in the art. Such reactions are described in *Journal of the American Chemical Society*, 109(10), 3087-3091, 1987. Typically, the free acid of Formula I is contacted with an excess of the amine of structure 4 in the presence of an weak organic base such as diisopropyl ethyl amine, in a solvent such as DMF (N,N-dimethylformamide). Other potential bases include N-methylmorpholine, carbodiimide, etc. A coupling agent is typically added to the reaction. Examples of such coupling agents include 1-hydroxybenztriazole "HOBT", 1-H-Benzotriazolium "HBTU", and (1-[3-(dimethylamino)propyl]-3-ethyl-carbodiimide hydrochloride. The reaction is typically carried out at room temperature for a period of time ranging from 5 minutes to 24 hours. The desired product of Formula I may be recovered by extraction, evaporation, or other techniques known in the art. It may then optionally be purified by chromatography, recrystallization, distillation, or other techniques known in the art.

If the desired product of Formula I is an ester, it may be synthesized as described in Reaction Scheme III below:

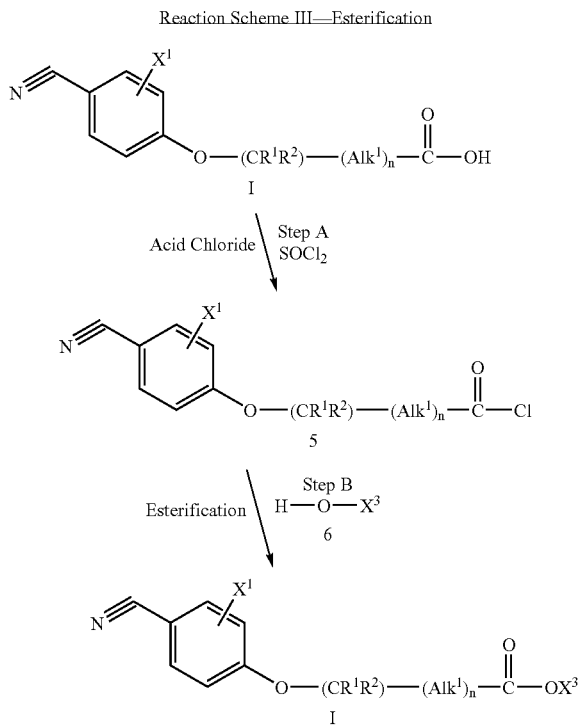

The free acid of Formula I is transformed into the acid chloride of structure 5, as known in the art. Please refer to *Tetrahedron Letters* (1986), 27(49), 5997-6000 for further details regarding the preparation of acid chlorides Typically the free acid is contacted with an excess of thionyl chloride in an organic solvent such as THF. The acid chloride of structure 5 may be recovered by distillation as is known in the art.

The acid chloride of structure 5 is converted into an ester as is known in the art. The acid chloride is contacted with an alcohol as described by structure 6, in which $X^3$ is represented by the same substitutent as is desired in the final product. These alcohols are known in the art The esterification is carried out by contacting the acid chloride with the alcohol of structure 6 in the presence of a mineral acid such as hydrochloric acid, sulfuric acid, etc., in an organic solvent such as acetonitrile under elevated temperatures. Such reactions are described in *Tetrahedron Letters*, 43(47), 8603-8606; 2002

As is readily apparent to one skilled in the art, carboxylic acids can be converted into amides and esters by a number of techniques. The reader's attention is directed to *Journal of the American Chemical Society*, 109(10), 3087-3091, 1987, for a brief description of such reactions. These alternative reactions may also be used to produce the amides and ester of Formula I.

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. See, e.g., T. W. Greene, *Protective Groups in Organic Synthesis*, John Wiley & Sons, New York, 1991.

Some of the compounds of this invention are acidic and they form a salt with a pharmaceutically acceptable cation. Some of the compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds are obtained in crystalline form according to procedures known in the art, such as by dissolution in an appropriate solvent(s) such as ethanol, hexanes or water/ethanol mixtures.

Medical and Cosmetic Uses

The compounds of Formula I are androgen receptor modulators. They can be used to alleviate conditions associated with inappropriate activation of the androgen receptor. Compounds acting as androgen antagonists may be used to treat, or alleviate, hormone dependent cancers such as prostate carcinomas, benign hyperplasia of the prostate, acne, hirsutism, excess sebum, alopecia, hypertrichosis, precocious puberty, prostamegaly, virilization, and polycystic ovary syndrome. Compounds acting as partial agonists, or full agonists, may be used to treat, or alleviate, male hypogonadism, male sexual dysfunction (impotence, male dysspemtatogenic sterility), abnormal sex differentiation (male hermaphroditism), male delayed puberty, male infertility, aplastic anemia, hemolytic anemia, sickle cell anemia, idiopathic thrombocytopenic purpura, myelofibrosis, renal anemia, wasting diseases (post operative, malignant tumor, trauma, chronic renal disease, burn or AIDS induced), abatement of pain in terminal carcinoma of female genitalia, inoperable breast cancer, mastopathy, endometriosis, female sexual dysfunction, osteoporosis, wound healing and muscle tissue repair.

In order to exhibit the therapeutic properties described above, the compounds need to be administered in a quantity sufficient to modulate activation of the androgen receptor. This amount can vary depending upon the particular disease/condition being treated, the severity of the patient's disease/condition, the patient, the particular compound being administered, the route of administration, and the presence of other underlying disease states within the patient, etc. When administered systemically, the compounds typically exhibit their effect at a dosage range of from about 0.1 mg/kg/day to about 100 mg/kg/day for any of the diseases or conditions listed above. Repetitive daily administration may be desirable and will vary according to the conditions outlined above.

The compounds of the present invention may be administered by a variety of routes. They may be administered orally. The compounds may also be administered parenterally (i.e. subcutaneously, intravenously, intramuscularly, intraperitoneally, or intrathecally), rectally, or topically.

In a typical embodiment, the compounds are administered topically. Topical administration is especially appropriate for hirsutism, alopecia, acne and excess sebum. The dose will vary, but as a general guideline, the compound will be present in a dermatologically acceptable carrier in an amount of from about 0.01 to 50 w/w %, and more typically from about 0.1 to 10 w/w %. The dermatological preparation will be applied to the affected area from 1 to 4 times daily. "Dermatologically acceptable" refers to a carrier which may be applied to the skin or hair, and which will allow the drug to diffuse to the site of action. More specifically, it refers the site where inhibition of activation of an androgen receptor is desired.

In a further embodiment, the compounds are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. Androgenic alopecia is also common in women where it usually present as a diffuse hair loss rather than showing the patterning seen in men.

While the compounds will most typically be used to alleviate androgenic alopecia, the invention is not limited to this specific condition. The compounds may be used to alleviate any type of alopecia. Examples of non-androgenic alopecia include alopecia areata, alopecia due to radiotherapy or chemotherapy, scarring alopecia, stress related alopecia, etc. As used in this application, "alopecia" refers to partial or complete hair loss on the scalp.

Thus, the compounds can be applied topically to the scalp and hair to prevent, or alleviate balding. Further, the compound can be applied topically in order to induce or promote the growth of hair on the scalp.

In a further embodiment of the invention, a compound of Formula I is applied topically in order to prevent the growth of hair in areas where such hair growth is not desired. One such use will be to alleviate hirsutism. Hirsutism is excessive hair growth in areas that typically do not have hair (i.e. a female face). Such inappropriate hair growth occurs most commonly in women and is frequently seen at menopause. The topical administration of the compounds will alleviate this condition leading to a reduction, or elimination of this inappropriate, or undesired, hair growth.

The compounds may also be used topically to decrease sebum production and more specifically to alleviate oily skin. Likewise the compounds can be used topically to alleviate acne.

In a further embodiment, those compounds acting as partial agonists, or full agonists, may be used to treat, or alleviate, osteoporosis. Osteoporosis is characterized by bone loss, resulting from an imbalance between bone resorption (destruction) and bone formation, which starts in the fourth decade and continues throughout life at the rate of about 1-4% per year (Eastell, Treatment of postmenopausal osteoporosis, New Eng. J. Med. 338: 736, 1998). In the United States, there are currently about 20 million people with detectable fractures of the vertebrae due to osteoporosis. In addition, there are about 250,000 hip fractures per year due to osteoporosis, associated with a 12%-20% mortality rate within the first two years, while 30% of patients require nursing home care after the fracture and many never become fully ambulatory again. In postmenopausal women, estrogen deficiency leads to increased bone resorption resulting in bone loss in the vertebrae of around 5% per year, immediately following menopause. Thus, first line treatment/prevention of this condition is inhibition of bone resorption by bisphosphonates, estrogens, selective estrogen receptor modulators (SERMs) and calcitonin. However, inhibitors of bone resorption are not sufficient to restore bone mass for patients who have already lost a significant amount of bone. The increase in spinal BMD attained by bisphosphonate treatment can reach 11% after 7 years of treatment with alendronate. In addition, as the rate of bone turnover differs from site to site; higher in the trabecular bone of the vertebrae than in the cortex of the long bones, the bone resorption inhibitors are less effective in increasing hip BMD and preventing hip fracture. Therefore, osteoanabolic agents, which increase cortical/periosteal bone formation and bone mass of long bones, would address an unmet need in the treatment of osteoporosis especially for patients with high risk of hip fractures.

A number of studies demonstrate that androgens are osteoanabolic in women and men. Anabolic steroids, such as nandrolone decanoate or stanozolol, have been shown to increase bone mass in postmenopausal women. Beneficial effects of androgens on bone in post-menopausal osteoporosis are well documented in recent studies using combined testosterone and estrogen administration (Hofbauer, et al., Androgen effects on bone metabolism: recent progress and controversies, Eur. J. Endocrinol. 140, 271-286, 1999). Thus those compounds of Formula I exhibiting agonist or partial agonist activity may be used to treat, or alleviate, osteoporosis, including primary osteoporosis such as senile, postmenopausal and juvenile osteoporosis, as well as secondary osteoporosis, such as osteoporosis due to hyperthyroidism or Cushing syndrome (due to corticosteroid treatment), acromegaly, hypogonadism, dysosteogenesis and hypophosphatasemia. Other bone related indications amendable to treat from androgen agonists include osteoporotic fracture, childhood idiopathic bone loss, alveolar bone loss, mandibular bone loss, bone fracture, osteotomy, periodontitis, or prosthetic ingrowth.

Those compounds acting as agonists, or partial agonists, can also be used to stimulate muscle mass in patients afflicted with wasting diseases, such as AIDS, cancer cachexia, burns, renal disease, etc. Patients suffering from trauma, bedsores, age, etc. can also benefits from the anabolic effects of androgens.

Co-Administration

In a further embodiment of the invention, the compounds of Formula I can be co-administered with other compounds to further enhance their activity, or to minimize potential side effects. For example, potassium channel openers, such as minoxidil, are known to stimulate hair growth and to induce anagen. Examples of other potassium channel openers include (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran, diaxozide, and PO 1075 which is under development by Leo Pharmaceuticals. Such compounds can be co-administered with the compounds of Formula I to alleviate alopecia Thyroid hormone is also known to stimulate hair growth. Synthetic thyroid hormone replacements (i.e. thyromimetics) have also been shown to stimulate hair growth. Such thyromimetics have been described in the literature previously. The reader's attention is directed to European Patent Application No. 1262177, the contents of which are hereby incorporated by reference, for a discussion of such compounds and their use to alleviate alopecia. One particular compound of interest is 2-{4-[3-(4-Fluoro-benzyl)-4-hydroxy-phenoxy]-3,5-dimethyl-phenyl}-2H-[1,2,4]triazine-3,5-dione. Such compounds can be co-administered with the compounds of Formula I to alleviate alopecia.

Anti-androgens can work by a number of different mechanisms. For example, some compounds block the conversion of testosterone to 5-α-dihydrotestosterone, which is responsible for the biological effect in many tissues. 5-Alpha-reductase inhibitors, such as finasteride, have been shown to stimulate hair growth. Finasteride is commercially available from Merck under the trade name Propecia®. Examples of other 5-α-reductase inhibitors include dutasteride (Glaxo SmithKline). Such compounds can be co-administered with the compounds of Formula I to alleviate alopecia.

Protein kinase C inhibitors have also been shown to stimulate hair growth and induce anagen. Calphostin C, which is a selective inhibitor of protein kinase C, has been shown to induce anagen. Other selective protein kinase C inhibitors, such as hexadecylphosphocholine, palmitoyl-DL-carnitine chloride, and polymyxin B sulfate have also been shown to induce anagen. Skin Pharmacol Appl Skin Physiol 2000 May-August; 13(3-4):133-42 Any such protein kinase C inhibitor can be co-administered with a compound of Formula I to alleviate alopecia.

Immunophilins are a family of cytoplasmic proteins. Their ligands include cyclosporin, FK506, and rapamycin. They are derived from fungi and were developed primarily for their potent immunosuppressive properties. Cyclosporin binds to the protein, cyclophilin, while FK506 and rapamycin bind to FK binding protein (FKBP). All of these compounds have been shown to stimulate hair growth and induce anagen. Any such immunophilin ligands can be co-administered with a compound of Formula I to alleviate alopecia.

As used in this application, co-administered refers to administering a compound of Formula I with a second anti-alopecia agent, typically having a differing mechanism of action, using a dosing regimen that promotes hair growth in the patient. This can refer to simultaneous dosing, dosing at different times during a single day, or even dosing on different days. The compounds can be administered separately or can be combined into a single formulation. Techniques for preparing such formulations are described below.

Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly to the skin or hair.

Pharmaceutical and cosmetic compositions can be manufactured utilizing techniques known in the art. Typically an effective amount of the compound will be admixed with a pharmaceutically/cosmetically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention will typically be administered topically. As used herein, topical refers to application of the compounds (and optional carrier) directly to the skin and/or hair. The topical composition according to the present invention can be in the form of solutions, lotions, salves, creams, ointments, liposomes, sprays, gels, foams, roller sticks, or any other formulation routinely used in dermatology.

Thus, a further embodiment relates to cosmetic or pharmaceutical compositions, in particular dermatological compositions, which comprise at least one of the compounds corresponding to Formula I above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily. The reader's attention is directed to *Remington's Pharmaceutical Science*, Edition 17, Mack Publishing Co., Easton, Pa. for a discussion of how to prepare such formulations.

The compositions according to the invention can also consist of solid preparations constituting cleansing soaps or bars. These compositions are prepared according to the usual methods.

The compounds can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the various constituents in the dermatological compositions according to the invention are those conventionally used in the fields considered.

The medicinal and cosmetics containing the compounds of the invention will typically be packaged for retail distribution (i.e. an article of manufacture). Such articles will be labeled and packaged in a manner to instruct the patient how to use the product. Such instructions will include the condition to be treated, duration of treatment, dosing schedule, etc.

The compounds of Formula I may also be admixed with any inert carrier and utilized in laboratory assays in order to determine the concentration of the compounds within the serum, urine, etc., of the patient as is known in the art. The compounds may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data is being presented in order to further illustrate the invention. This disclosure should not be construed as limiting the invention in any manner.

EXAMPLES

Example 1

2-(4-Cyano-3-trifluoromethyl-phenoxy)-4-methyl-pentanoic acid benzylamide

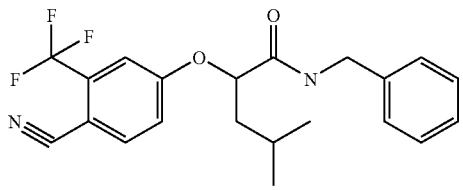

Step 1:

2-(4-cyano-3-trifluoromethyl-phenoxy)-4-methyl-pentanoic acid isopropyl ester (1A) is prepared by the following method:

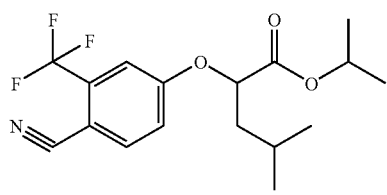

1A

The starting materials, DL-leucic acid isopropyl ester (5.22 g in 100 ml of dry THF, 30 mmol) and NaH (1.4 g, 36 mmol) are stirred at 0° C. under $N_2$ for 15 min., then 4-fluoro-2-trifluoromethyl-benzonitrile (5.67 g, 30 mmol), is added, the reaction mixture is stirred at 0° C. for 1 hour, then room temperature for 3 hours It is quenched with saturated $NaHCO_3$, extracted with ethyl acetate. The crude product is purified by column to yield an oily liquid as the pure product. (7 g).

Step 2:

2-(4-Cyano-3-trifluoromethyl-phenoxy)-4-methyl-pentanoic acid (1B)

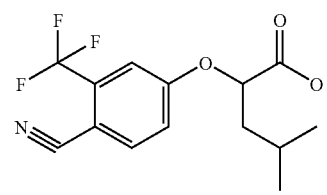

1B

An admixture of 2-(4-cyano-3-trifluoromethyl-phenoxy)-4-methyl-pentanoic acid isopropyl ester (1A) (0.22 g, 0.67 mmol in 20 ml of dry tetrahydrofuran "THF"), LiOH (0.28 g, 6.7 mmol) and water (20 ml) is refluxed at 100° C. for 3 hours, then it is cooled to room temperature, the THF is removed, the crude product is diluted with 100 ml of ethyl acetate, and HCl(1N) to adjusted PH=1. The organic layer is separated and dried on vacuum to get the desired product.

Step 3:

2-(4-Cyano-3-trifluoromethyl-phenoxy)-4-methyl-pentanoic acid benzylamide (Example 1)

An admixture of 2-(4-cyano-3-trifluoromethyl-phenoxy)-4-methyl-pentanoic acid (1B) (0.20 g, 0.67 mmol in 20 ml of dimethylformamide "DMF" benzylamine (0.16 g, 1.59 mmol), diisopropyl ethylamine (0.26 g, 2 mmol) and 1-H-Benzotriazolium ("HBTU") (0.25 g, 0.67 mmol) is stirred at room temperature ("RT") for 4 hours, then the reaction is diluted with ethyl acetate, it is then washed with saturated $NaHCO_3$ (three times), the organic layer is separated and the solvent is removed to yield the crude product, it is purified by liquid chromatography mass spectroscopy ("LCMS") using the eluent described below.

MS: 391.1 (M+1 for $C_{21}H_{21}N_2F_3O_2$) LCMS: C-18 Column (25% $H_2O$/75% $CH_3CN$), Ret. Time: 1.46 min Purity: 100%.

Example 2

2-(4-Cyano-3-trifluoromethyl-phenoxy)-4-methyl-pentanoic acid isopropylamide

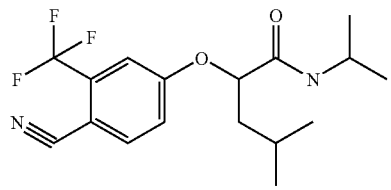

The product of Example 2 is prepared analogously to Example 1, except isopropyl amine is used instead of benzyl amine in Step 3. The desired product is purified by silica gel column:

MS: 343.2 (M+1 for $C_{17}H_{21}N_2F_3O_2$) LCMS: C-18 Column (25% $H_2O$/75% $CH_3CN$), Ret. Time: 1.21 min Purity: 100%.

Example 3

2-(4-Cyano-3-trifluoromethyl-phenoxy)-4-methyl-pentanoic acid ethylamide

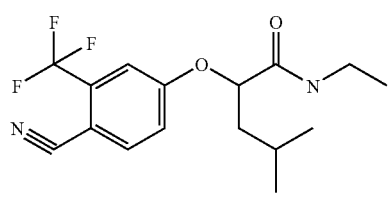

The product of Example 3 is prepared analogously to Example 1, except ethylamine is used instead of benzyl amine in Step 3. The desired product is purified by silica gel column.

MS: 329.2 (M+1 for $C_{16}H_{19}N_2F_3O_2$) LCMS: C-18 Column (50% $H_2O$/50% $CH_3CN$), Ret. Time: 2.65 min Purity: 100%.

Example 4

2-(4-Cyano-3-trifluoromethyl-phenoxy)-pentanoic acid benzylamide

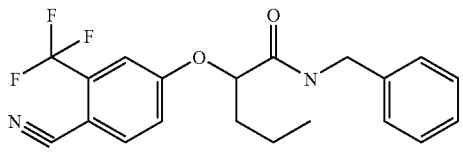

The product of Example 4 is prepared analogously to example 1, except in step 1, DL-2-hydroxy-pentanoic acid ethyl ester is used instead of DL-leucic acid isopropyl ester as one of the starting materials. The desired product is purified by silica gel column.

MS: 377.1 (M+1 for $C_{20}H_{19}N_2F_3O_2$) LCMS: C-18 Column (25% $H_2O$/75% $CH_3CN$), Ret. Time: 1.31 min Purity: 100%.

Example 5

2-(4-Cyano-3-trifluoromethyl-phenoxy)-pentanoic acid ethylamide

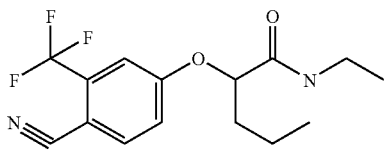

The product of Example 5 is prepared analogously to example 1, except ethylamine is used instead of benzyl amine in Step 3. The desired product is purified by silica gel column.

MS: 315.1 (M+1 for $C_{15}H_{17}N_2F_3O_2$) LCMS: C-18 Column (50% $H_2O$/50% $CH_3CN$), Ret. Time: 2.31 min Purity: 100%.

Example 6

2-(4-Cyano-3-trifluoromethyl-phenoxy)-pentanoic acid [1-(4-hydroxy-phenyl)ethyl]-amide

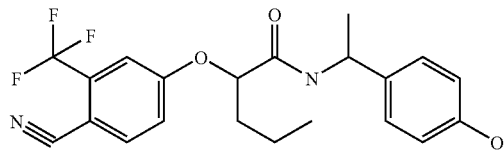

The product of Example 6 is prepared analogously to Example 1, except that 4-(1-amino-ethyl)-phenol is used instead of benzyl amine in Step 3. The desired product is purified by silica gel column.

MS: 407.35(M+1 for $C_{21}H_{21}F_3N_2O_3$. LCMS: Polar RP-Phenyl column 100 mm×4.6 mm, 4 mm (Solvent: A=Water w/0.1M Formic Acid; B=Acetonitrile w/0.1 M Formic Acid, Method: 0-2.5 min: 95% A, 10% B; 2.5-5.1 min: 2% A, 98% B; 5.1-7 min: 95% A, 5% B), Ret. Time: 3.81 min. Purity: 100%.

Example 7

2-(4-Cyano-3-trifluoromethyl-phenoxy)-4-methyl-pentanoic acid cyclopropylmethyl-amide

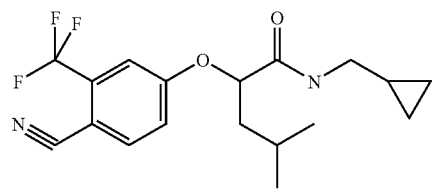

The product of Example 7 is prepared analogously to Example 1, except cyclopropylmethyl amine is used instead of benzyl amine in Step 3. The desired product is purified by silica gel column.

MS: 355.1 (M+1 for $C_{18}H_{21}N_2F_3O_2$) LCMS: C-18 Column (50% $H_2O$/50% $CH_3CN$), Ret. Time: 3.09 min Purity: 100%.

Example 8

2-(4-Cyano-3-trifluoromethyl-phenoxy)-4-methyl-pentanoic acid isobutyl-amide

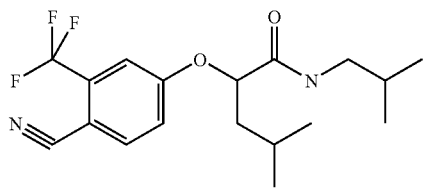

The product of Example 8 is prepared analogously to example 1, except isobutyl amine is used instead of benzyl amine in Step 3. The desired product is purified by silica gel column.

MS: 357.1 (M+1 for $C_{18}H_{23}N_2F_3O_2$) LCMS: C-18 Column (50% $H_2O$/50% $CH_3CN$), Ret. Time: 2.53 min Purity: 100%.

Example 9

2-(4-Cyano-3-trifluoromethyl-phenoxy)-4-methyl-pentanoic acid [2-(4-methoxyphenyl)-ethyl]-amide

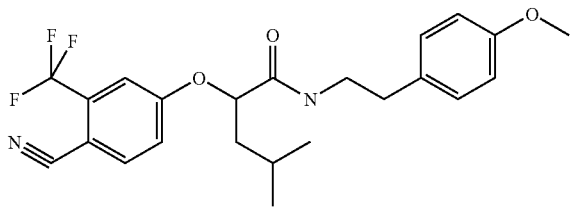

The product of Example 9 is prepared analogously to example 1, except 2-(4-methoxy-phenyl)-ethyl amine is used instead of the benzyl amine in Step 3. The desired product is purified by silica gel column.

MS: 435.33 (M+1 for $C_{23}H_{25}N_2F_3O_3$) LCMS: C-18 Column (25% $H_2O$/75% $CH_3CN$), Ret. Time: 4.54 min Purity: 89%.

Example 10

2-(4-Cyano-3-trifluoromethyl-phenoxy)-4-methyl-pentanoic acid (2-phenoxyethyl)-amide

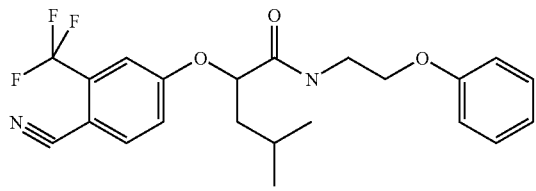

The product of Example 10 is prepared analogously to example 1, except 2-phenoxy-ethyl amine is used instead of the benzyl amine in Step 3. The desired product is purified by LCMS as described below.

MS: 421.22(M+1 for $C_{23}H_{23}F_3N_2O_3$). LCMS: Phen Aqua C18 4.6 um×100 um, 3 mm column (Solvent: A=Water w/0.1M Formic Acid; B=Acetonitrile w/0.1M Formic Acid, Method: 0-3 min: 90% A, 10% B; 3-5.1 min: 2% A, 98% B; 5.1-7 min: 90% A, 10% B), Ret. Time: 4.47 min. Purity: 100%.

Examples 11-90

The products of Examples 11-90, 115, and 116 were prepared by combinatorial chemistry, as described below, using the synthesis described in Reaction Scheme II above (i.e. amidation). One of the reactants was a compound of Formula I in which Y is OH, either 2-(4-cyano-3-trifluoromethyl-phenoxy)-4-methyl-pentanoic acid or 2-(4-cyano-3-trifluoromethyl-phenoxy)-pentanoic. These compounds were prepared as described in Examples 1 and 4, above. The other reactant was the appropriate amine, as described by structure 4 above in which $X^2$ and $X^3$ correspond to the final product.

The compounds depicted below in Examples 11, 12, 13, 15, 16, 17, 19, 20, 21, 22 were prepared in the following manner. To 1 mL of 0.1M (molar) solutions of either 2-(4-cyano-3-trifluoromethyl-phenoxy)-4-methyl-pentanoic acid or 2-(4-cyano-3-trifluoromethyl-phenoxy)-pentanoic acid in dimethylformamide "DMF" (0.1 mmol) was added 1.0 mL of a 0.12M solution of 1-hydroxybenztriazole "HOBT" (0.12 mmol) in DMF, 0.3 mL of a 1.0M solution of the appropriate amine of structure 4 (0.3 mmol) in DMF, and approximately 64 mg of polystyrene bound carbodiimide (loading: 1.9 mmol/g, 0.12 mmol). The resultant mixture was shaken and heated at 70° C. for approximately 18 hours. The reaction was cooled to RT and approximately 40 mg of macroporous polystyrene bound carbonate (loading: 3.21 mmol/g, 0.128 mmol) was added. The resultant mixture was shaken at room temperature for approximately 18 hours. To the reaction was added 1.0 mL of a 0.12M solution of HOBT (0.12 mmol) in DMF, 0.3 mL of a 1.0M solution of the appropriate amine of structure 4 (0.3 mmol) in DMF, and approximately 64 mg of polystyrene bound carbodiimide (loading: 1.9 mmol/g, 0.12 mmol). The resultant mixture was shaken and heated at 70° C. for approximately 18 hours. The reaction was cooled to room temperature and approximately 288 mg of polystyrene bound isocyanate (loading: 2.08 mmol/g, 0.6 mmol) and approximately 40 mg of macroporous polystyrene bound carbonate was added. The resultant mixture was shaken at room temperature for approximately 30 min., filtered and the resin was thoroughly rinsed with tetrahydrofuran. The solvent was removed in vacuo using an evaporator, Genevac HT-12, to obtain a sample that was purified by HPLC ("high performance liquid chromatography".

The compounds depicted below in Examples 9, 10, 14, 18, 23-27, 29-68 were prepared in the following manner. To 1 mL of 0.1M solutions of either 2-(4-cyano-3-trifluoromethyl-phenoxy)-4-methyl-pentanoic acid or 2-(4-cyano-3-trifluoromethyl-phenoxy)-pentanoic acid in DMF (0.1 mmol) was added 1.0 mL of a 0.24M solution of HOBT (0.24 mmol) in DMF, 0.6 mL of a 1.0M solution of the appropriate amine of structure 4 (0.6 mmol) in DMF, and approximately 126 mg of polystyrene bound carbodiimide (loading: 1.9 mmol/g, 0.24 mmol). The resultant mixture was shaken and heated at 70° C. for approximately 22 hours. The reaction was cooled to RT and approximately 100 mg of macroporous polystyrene bound carbonate (loading: 2.64 mmol/g, 0.264 mmol) and approximately 150 mg of macroporous polystyrene bound tosic acid resin (loading: 4.07 mmol/g, 0.610 mol) was added. The resultant mixture was shaken at room temperature for approximately 18 hours. To the reaction was added 1.0 mL of a 0.24M solution of HOBT (0.24 mmol) in DMF, 0.6 mL of a 1.0M solution of the appropriate amine of structure 4 (0.6 mmol) in DMF, and approximately 100 mg of polystyrene bound carbodiimide (loading: 1.9 mmol/g, 0.19 mmol). The resultant mixture was shaken and heated at 70° C. for approximately 10 hours. The reaction was cooled to room temperature, filtered and the resin was thoroughly rinsed with methanol. The solvent was removed in vacuo using a high thru put evaporator, Genevac HT-12, to obtain a sample that was then purified by HPLC.

The compounds depicted below in Examples 6, 69-77 were prepared in the following manner. To 1 mL of 0.1M solutions of either 2-(4-cyano-3-trifluoromethyl-phenoxy)-4-methyl-pentanoic acid or 2-(4-cyano-3-trifluoromethylphenoxy)-pentanoic acid in DMF (0.1 mmol) was added 1.0 mL of a 0.48M solution of HOBT (0.48 mmol) in DMF, and approximately 226 mg of polystyrene bound carbodiimide (loading: 1.9 mmol/g, 0.43 mmol). The resultant mixture was shaken at room temperature for 1 hour. To the reaction was added 0.6 mL of a 1.0M solution of the appropriate amine of structure 4 (0.6 mmol) in DMF. The resultant mixture was shaken and heated at 70° C. for approximately 22 hours. The reaction was cooled to RT. Added 200 mg of polystyrene bound carbodimide (loading: 1.9 mmol/g, mmol) and 65 mg of HOBT to the reaction. The resultant mixture was shaken at 70° C. for approximately 15 hours. The reaction was cooled to RT and approximately 379 mg of macroporous polystyrene bound carbonate (loading: 2.64 mmol/g, 1 mmol) was added to each vial. The resultant mixture was shaken at room temperature for approximately 18 hours. Filtered and the resin was thoroughly rinsed with methanol. The solvent was removed in vacuo using a Genevac HT-12 to obtain a sample that was then purified by HPLC.

The compounds depicted below in Examples 78-90 were prepared in the following manner. To 0.5 mL of 0.2M solutions of either 2-(4-cyano-3-trifluoromethyl-phenoxy)-4-methyl-pentanoic acid or 2-(4-cyano-3-trifluoromethylphenoxy)-pentanoic acid in DMF (0.1 mmol) was added 1.0 mL of a 0.4M solution of HOBT (0.2 mmol) in DMF, and approximately 183 mg of polystyrene bound carbodiimide (loading: 1.9 mmol/g, 0.2 mmol), and 0.1 mL of a 1.0M solution of the appropriate amine of structure 4 (0.1 mmol) in DMF. The resultant mixture was shaken and heated at 70° C. for approximately 22 hours. The reaction was cooled to RT. Filtered and the resin was thoroughly rinsed with methanol. The solvent was removed in vacuo using a Genevac HT-12 to obtain a sample that was then purified by HPLC.

The compounds depicted below in Examples 115 and 116 were prepared in the following manner. To 0.5 mL of 0.2M solutions of either 2-(4-cyano-3-trifluoromethyl-phenoxy)-4-methyl-pentanoic acid or 2-(4-cyano-3-trifluoromethylphenoxy)-pentanoic acid in dimethylformamide "DMF" (0.1 mmol) were added 1.0 mL of a 0.4M solution of 1-hydroxybenztriazole "HOBT" (0.2 mmol) in DMF, and approximately 183 mg of polystyrene bound carbodiimide (loading: 1.9 mmol/g, 0.2 mmol), and 0.1 mL of a 1.0M solution of the appropriate amine of structure 4 (0.1 mmol) in DMF. The resultant mixtures were shaken and heated at 70° C. for approximately 22 hours. The reactions were cooled to RT. Filtered and the resin was thoroughly rinsed with methanol. The solvent was removed in vacuo using a Genevac HT-12 to obtain samples that were then purified by HPLC.

Three different HPLC (high performance liquid chromatography) methods were utilized to purify the compounds. These methods are summarized below:

1) Method A

HPLC Conditions:
Column: BHK 30×100 mm ODS-A 5 μm C-18.
Flow rate: 30 mL/min
Solvent: A=Acetonitrile w/3% 1-Propanol; B=Water w/3% 1-Propanol
Method: 0-6.5 min: 15% A, 85% B; 6.5-10.5 min: 100% A 2) Method B HPLC Conditions:
Column: YMC 30×100 mm ODS-A 5 μm C-18.
Flow rate: 30 mL/min
Solvent: A=Acetonitrile w/3% 1-Propanol; B=Water w/3% 1-Propanol
Method: 0-6.5 min: 15% A, 85% B; 6.5-10.5 min: 100% A 3) Method C HPLC Conditions:
Column: Xterra 30×100 mm 5 μm C-18.
Flow rate: 30 mL/min
Solvent: A=Acetonitrile w/3% 1-Propanol; B=Water w/3% 1-Propanol
Method: 0-6.5 min: 25% A, 75% B; 6.5-10.5 min: 100% A The compounds were also subjected to liquid chromatographic mass spectrometry (LCMS) using one of three methods as described below:

Method A

LCMS: Atlantis C18 5 cm×4.6 mm, 3 mm column (Solvent: A=Water w/0.1M Formic Acid; B=Acetonitrile w/0.1M Formic Acid, Method: 0-3 min: 90% A, 10% B; 3-5.1 min: 2% A, 98% B; 5.1-7 min: 90% A, 10% B Method B LCMS: Phen Aqua C18 4.6 um×100 um, 3 mm column (Solvent: A=Water w/0.1M Formic Acid; B=Acetonitrile w/0.1M Formic Acid, Method: 0-3 min: 90% A, 10% B; 3-5.1 min: 2% A, 98% B; 5.1-7 min: 90% A, 10% B), Method C LCMS: Polar RP-Phenyl column 100 mm×4.6 mm, 4 mm (Solvent: A=Water w/0.1M Formic Acid; B=Acetonitrile w/0.1M Formic Acid, Method: 0-2.5 min: 95% A, 10% B; 2.5-5.1 min: 2% A, 98% B; 5.1-7 min: 95% A, 5% B), Example 11

2-(4-Cyano-3-trifluoromethyl-phenoxy)-4-methyl-pentanoic acid (furan-2-yl-methyl)-amide

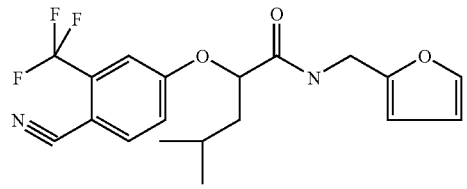

HPLC—Method A
LCMS—Method A
MS: 381.2(M+1 for $C_{19}H_{19}F_3N_2O_3$). Ret. Time: 3.64 min. Purity: 85.56%.

Example 12

2-(4-Cyano-3-trifluoromethyl-phenoxy)-4-methyl-pentanoic acid (thiophen-2-yl-methyl)-amide

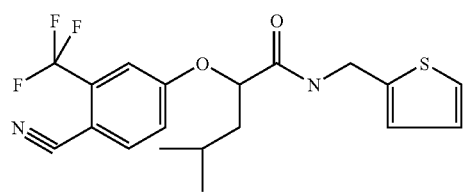

HPLC—Method A
LCMS—Method A
MS: 397.24(M+1 for $C_{19}H_{19}F_3N_2O_2S$). Ret. Time: 3.77 min. Purity: 94.55%.

Example 13

2-(4-Cyano-3-trifluoromethyl-phenoxy)-4-methyl-pentanoic acid (1-thiophen-2-ylethyl)-amide

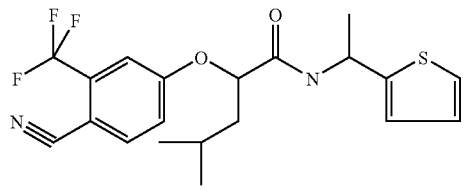

HPLC—Method A
LCMS—Method A
 MS: 411.23(M+1 for $C_{20}H_{21}F_3N_2O_2S$). Ret. Time: 3.82 min. Purity: 98.38%.

Example 14

2-(4-Cyano-3-trifluoromethyl-phenoxy)-4-methyl-pentanoic acid (1-methyl-2-thiophen-3-yl-ethyl)-amide

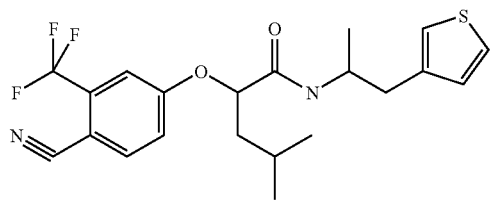

HPLC—Method B
LCMS—Method B
 MS: 425.22(M+1 for $C_{21}H_{23}F_3N_2O_2S$). Ret. Time: 4.64 min. Purity: 100%.

Example 15

2-(4-Cyano-3-trifluoromethyl-phenoxy)-4-methyl-pentanoic acid (1-pyridin-3-ylethyl)-amide

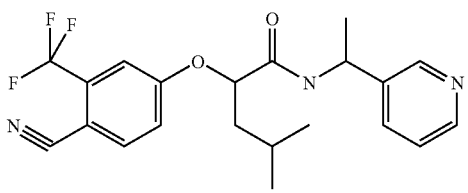

HPLC—Method B
LCMS—Method A
 MS: 406.29(M+1 for $C_{21}H_{22}F_3N_3O_2$). Ret. Time: 3.19 min. Purity: 97.78%.

Example 16

2-(4-Cyano-3-trifluoromethyl-phenoxy)-4-methyl-pentanoic acid (pyridin-4-yl-methyl)-amide

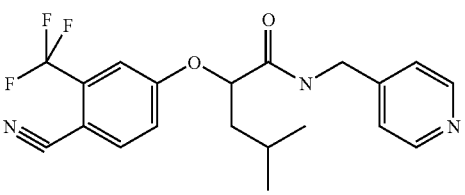

HPLC—Method A
LCMS—Method A
 MS: 392.29(M+1 for $C_{20}H_{20}F_3N_3O_2$). Ret. Time: 2.87 min. Purity: 86.11%.

Example 17

2-(4-Cyano-3-trifluoromethyl-phenoxy)-pentanoic acid (1-thiophen-2-yl-ethyl)amide

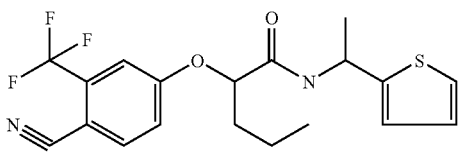

HPLC Method A
LCMS—Method B
 MS: 397.19(M+1 for $C_{19}H_{19}F_3N_2O_2S$). Ret. Time: 3.71 min. Purity: 100%.

Example 18

2-(4-Cyano-3-trifluoromethyl-phenoxy)-pentanoic acid (1-methyl-2-thiophen-3-ylethyl)-amide

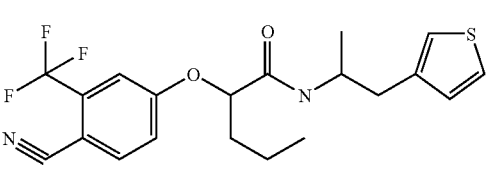

HPLC Method B
LCMS—Method B
 MS: 411.19(M+1 for $C_{20}H_{21}F_3N_2O_2S$). Ret. Time: 4.52 min. Purity: 100%

Example 19

2-(4-Cyano-3-trifluoromethyl-phenoxy)-4-methyl-pentanoic acid (pyridin-3-yl-methyl)-amide

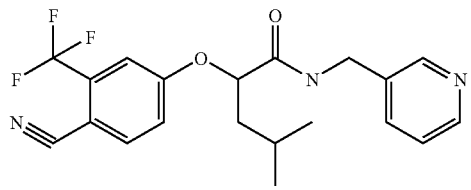

HPLC Method A
LCMS—Method A
MS: 392.25(M+1 for $C_{20}H_{20}F_3N_3O_2$). Ret. Time: 3.06 min. Purity: 97.63%.

Example 20

2-(4-Cyano-3-trifluoromethyl-phenoxy)-4-methyl-pentanoic acid (3-methyl-pyridin-2-yl-methyl)-amide

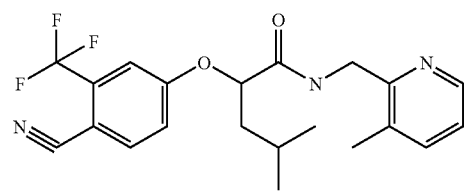

HPLC Method A
LCMS—Method A
MS: 406.29(M+1 for $C_{21}H_{22}F_3N_3O_2$). Ret. Time: 3.54 min. Purity: 87.09%.

Example 21

2-(4-Cyano-3-trifluoromethyl-phenoxy)-4-methyl-pentanoic acid (3-methylsulfanyl-propyl)-amide

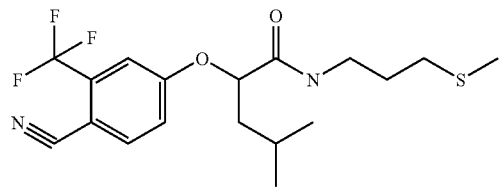

HPLC Method C:
LCMS—Method A
MS: 389.21(M+1 for $C_{18}H_{23}F_3N_2O_2S$). Ret. Time: 3.85 min. Purity: 95.92%.

Example 22

2-(4-Cyano-3-trifluoromethyl-phenoxy)-4-methyl-pentanoic acid (3-methyl-butyl)amide

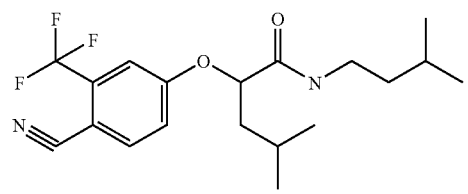

HPLC—Method A
LCMS—Method A
MS: 371.31(M+1 for $C_{19}H_{25}F_3N_2O_2$). Ret. Time: 3.91 min. Purity: 98.91%.

Example 23

2-(4-Cyano-3-trifluoromethyl-phenoxy)-4-methyl-pentanoic acid (3,3-diethoxy-propyl)-amide

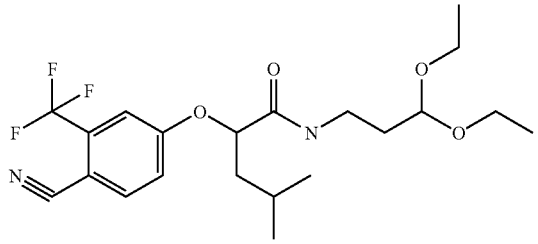

HPLC—Method B
LCMS—Method B
MS: 385.31(M+1 for $C_{21}H_{29}F_3N_2O_4$). Ret. Time: 4.61 min. Purity: 100%.

Example 24

2-(4-Cyano-3-trifluoromethyl-phenoxy)-4-methyl-pentanoic acid (benzo[1,3]dioxol-5-yl-methyl)-amide

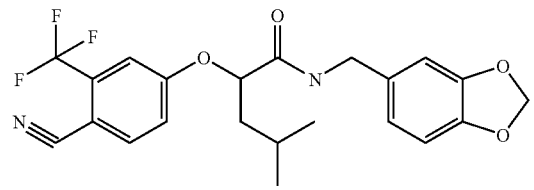

HPLC—Method B
LCMS—Method B
MS: 435.28(M+1 for $C_{22}H_{21}F_3N_2O_4$). Ret. Time: 4.46 min. Purity: 100%.

Example 25

2-(4-Cyano-3-trifluoromethyl-phenoxy)-4-methyl-pentanoic acid (2,3-dihydro-benzofuran-5-yl-methyl)-amide

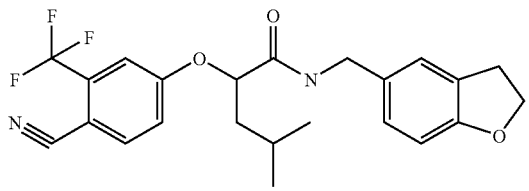

HPLC—Method B
LCMS—Method B

MS: 433.25(M+1 for $C_{23}H_{23}F_3N_2O_3$). Ret. Time: 4.51 min. Purity: 100%.

Example 26

2-(4-Cyano-3-trifluoromethyl-phenoxy)-4-methyl-pentanoic acid (benzo[1,2,5]thiadiazol-5-yl-methyl)-amide

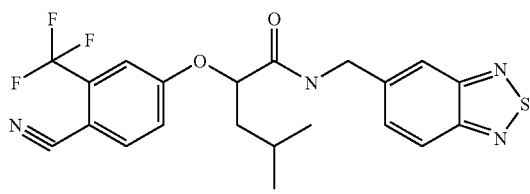

HPLC—Method B
LCMS—Method B

MS: 449.15(M+1 for $C_{21}H_{19}F_3N_4O_2S$). Ret. Time: 4.54 min. Purity: 100%.

Example 27

2-(4-Cyano-3-trifluoromethyl-phenoxy)-4-methyl-pentanoic acid (isochroman-3-yl-methyl)-amide

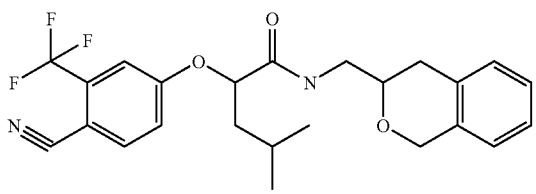

HPLC—Method B
LCMS—Method B

MS: 447.25(M+1 for $C_{24}H_{25}F_3N_2O_3$). Ret. Time: 4.66 min. Purity: 100%.

Example 28

2-(4-Cyano-3-trifluoromethyl-phenoxy)-4-methyl-pentanoic acid (3-methylsulfanyl-propyl)-amide

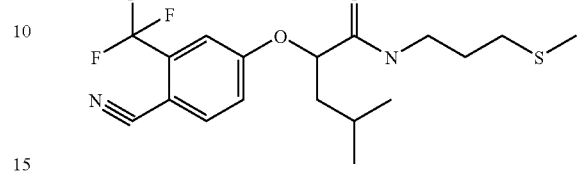

HPLC Method C
LCMS—Method A

MS: 389.21(M+1 for $C_{18}H_{23}F_3N_2O_2S$). Ret. Time: 3.85 min. Purity: 95.92%.

Example 29

2-(4-Cyano-3-trifluoromethyl-phenoxy)-pentanoic acid (benzo[1,3]dioxol-5-yl-methyl)-amide

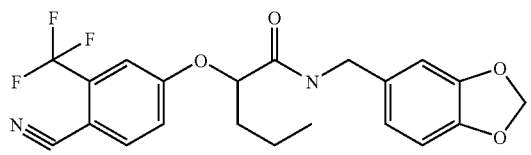

HPLC—Method B
LCMS—Method B

MS: 421.18(M+1 for $C_{21}H_{19}F_3N_2O_4$). Ret. Time: 4.34 min. Purity: 100%.

Example 30

2-(4-Cyano-3-trifluoromethyl-phenoxy)-pentanoic acid (2,3-dihydro-benzofuran-5-yl-methyl)-amide

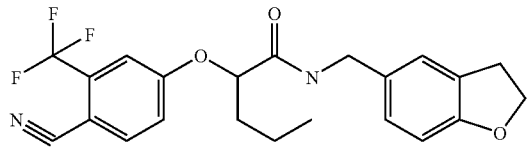

HPLC—Method
LCMS—Method B

MS: 419.19(M+1 for $C_{22}H_{21}F_3N_2O_3$). Ret. Time: 4.37 min. Purity: 100%.

Example 31

2-(4-Cyano-3-trifluoromethyl-phenoxy)-pentanoic acid (benzo[1,2,5]thiadiazo-5-yl-methyl)-amide

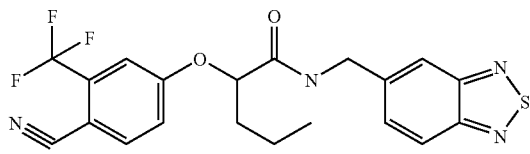

HPLC—Method B
LCMS—Method B
MS: 435.18(M+1 for $C_{20}H_{17}F_3N_4O_2S$). Ret. Time: 4.42 min. Purity: 100%.

Example 32

2-(4-Cyano-3-trifluoromethyl-phenoxy)-pentanoic acid (isochroman-3-yl-methyl)amide

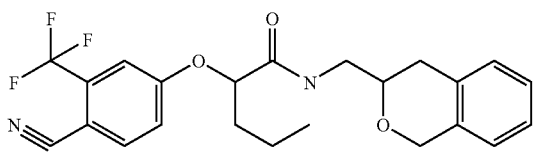

HPLC Method B
LCMS—Method B
MS: 433.24(M+1 for $C_{23}H_{23}F_3N_2O_3$). Ret. Time: 4.56 min. Purity: 100%.

Example 33

2-(4-Cyano-3-trifluoromethyl-phenoxy)-4-methyl-pentanoic acid-3-methoxy-benzylamide

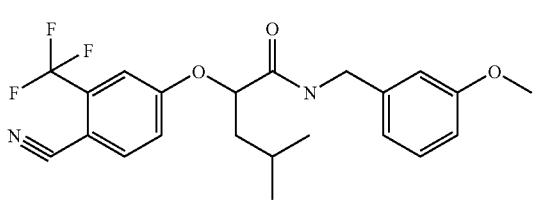

HPLC Method B
LCMS—Method B
MS: 421.3(M+1 for $C_{22}H_{23}F_3N_2O_3$). Ret. Time: 4.51 min. Purity: 100%

Example 34

2-(4-Cyano-3-trifluoromethyl-phenoxy)-4-methyl-pentanoic acid [2-(4-methoxyphenyl)-ethyl]amide

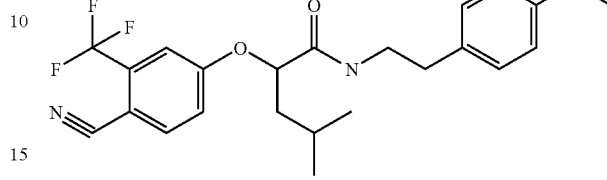

HPLC Method B
LCMS—Method B
MS: 435.33(M+1 for $C_{23}H_{25}F_3N_2O_3$). Ret. Time: 4.54 min. Purity: 89.19%.

Example 35

2-(4-Cyano-3-trifluoromethyl-phenoxy)-4-methyl-pentanoic acid-2-methoxy-benzylamide

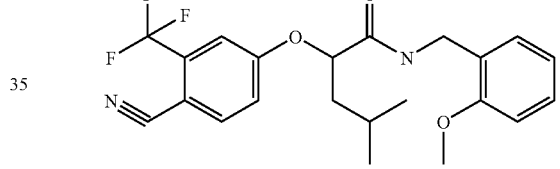

HPLC—Method B
LCMS—Method B
MS: 421.28(M+1 for $C_{22}H_{23}F_3N_2O_3$) Ret. Time: 4.59 min. Purity: 100%.

Example 36

2-(4-Cyano-3-trifluoromethyl-phenoxy)-4-methyl-pentanoic acid-2-ethoxy-benzylamide

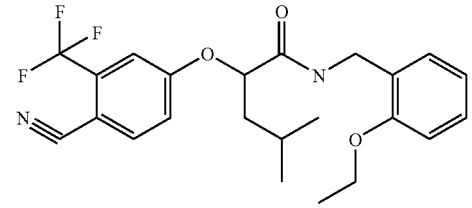

HPLC—Method B
LCMS—Method B
MS: 435.33(M+1 for $C_{23}H_{25}F_3N_2O_3$) Ret. Time: 4.69 min. Purity: 100%

Example 37

2-(4-Cyano-3-trifluoromethyl-phenoxy)-4-methyl-pentanoic acid-3-methyl-benzylamide

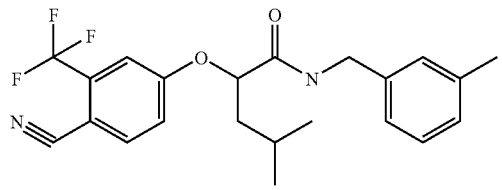

HPLC—Method B
LCMS—Method B
MS: 405.3(M+1 for $C_{22}H_{23}F_3N_2O_2$). Ret. Time: 4.64 min. Purity: 100%.

Example 38

2-(4-Cyano-3-trifluoromethyl-phenoxy)-4-methyl-pentanoic acid-2-methyl-benzylamide

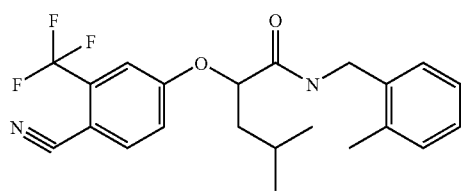

HPLC—Method B
LCMS—Method B
MS: 405.3(M+1 for $C_{22}H_{23}F_3N_2O_2$). Ret. Time: 4.64 min. Purity: 100%.

Example 39

2-(4-Cyano-3-trifluoromethyl-phenoxy)-4-methyl-pentanoic acid-4-methoxy-benzylamide

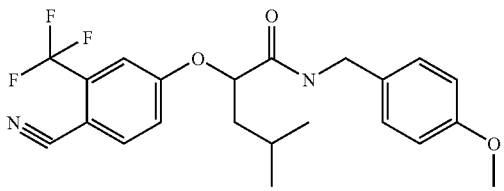

HPLC—Method B
LCMS—Method B
MS: 421.31(M+1 for $C_{22}H_{23}F_3N_2O_3$). Ret. Time: 4.46 min. Purity: 100%.

Example 40

2-(4-Cyano-3-trifluoromethyl-phenoxy)-pentanoic acid-3-methoxy-benzylamide

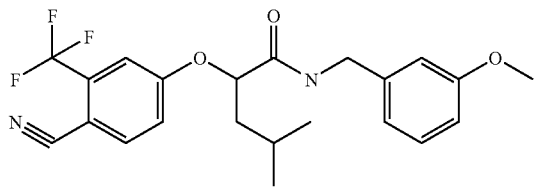

HPLC—Method B
LCMS—Method B
MS: 407.22(M+1 for $C_{21}H_{21}F_3N_2O_3$). Ret. Time: 4.41 min. Purity: 100%.

Example 41

2-(4-Cyano-3-trifluoromethyl-phenoxy)-pentanoic acid-2-methoxy-benzylamide

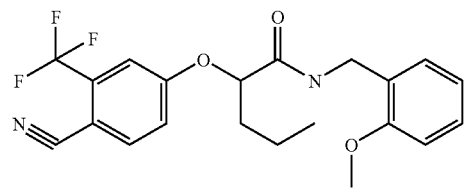

HPLC—Method B
LCMS—Method B
MS: 407.22(M+1 for $C_{21}H_{21}F_3N_2O_3$). Ret. Time: 4.49 min. Purity: 100%.

Example 42

2-(4-Cyano-3-trifluoromethyl-phenoxy)-pentanoic acid-2-ethoxy-benzylamide

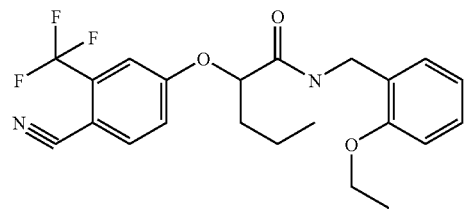

HPLC—Method B
LCMS—Method B
MS: 421.22(M+1 for $C_{22}H_{23}F_3N_2O_3$). Ret. Time: 4.64 min. Purity: 100%.

Example 43

2-(4-Cyano-3-trifluoromethyl-phenoxy)-pentanoic acid-3-methyl-benzylamide

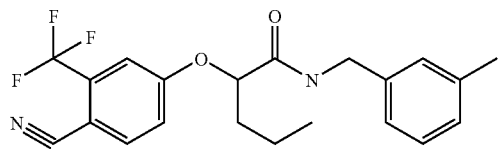

HPLC—Method B
LCMS—Method B

MS: 391.22(M+1 for $C_{21}H_{21}F_3N_2O_2$). Ret. Time: 4.54 min. Purity: 100%.

Example 44

2-(4-Cyano-3-trifluoromethyl-phenoxy)-pentanoic acid-2-methyl-benzylamide

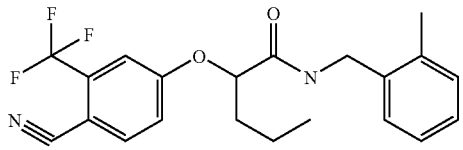

HPLC—Method B
LCMS—Method B

MS: 391.22(M+1 for $C_{21}H_{21}F_3N_2O_2$). Ret. Time: 4.54 min. Purity: 100%.

Example 45

2-(4-Cyano-3-trifluoromethyl-phenoxy)-pentanoic acid-2,4-dimethyl-benzylamide

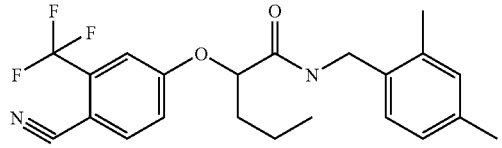

HPLC—Method B
LCMS—Method B

MS: 405.22(M+1 for $C_{22}H_{23}F_3N_2O_2$). Ret. Time: 4.62 min. Purity: 100%.

Example 46

2-(4-Cyano-3-trifluoromethyl-phenoxy)-pentanoic acid-4-methoxy-benzylamide

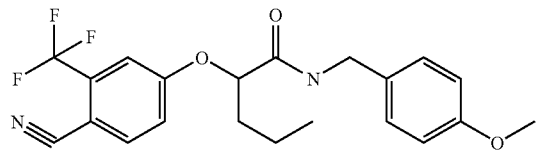

HPLC—Method B
LCMS—Method B

MS: 407.22(M+1 for $C_{21}H_{21}F_3N_2O_3$). Ret. Time: 4.39 min. Purity: 100%.

Example 47

2-(4-Cyano-3-trifluoromethyl-phenoxy)-4-methyl-pentanoic acid-(2-p-tolyl-ethyl)amide

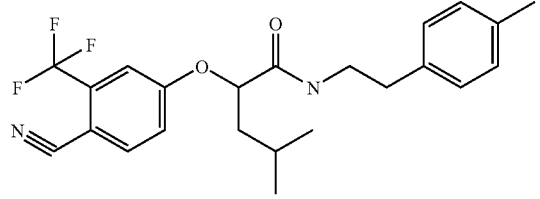

HPLC—Method B
LCMS—Method B

MS: 419.32(M+1 for $C_{23}H_{25}F_3N_2O_2$). Ret. Time: 4.72 min. Purity: 100%.

Example 48

2-(4-Cyano-3-trifluoromethyl-phenoxy)-4-methyl-pentanoic acid-[2-(2-methoxyphenyl)-ethyl]-amide

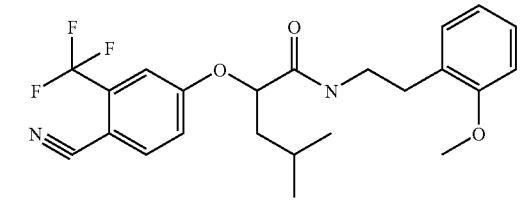

HPLC—Method B
LCMS—Method B

MS: 435.3(M+1 for $C_{23}H_{25}F_3N_2O_3$). Ret. Time: 4.67 min. Purity: 100%.

Example 49

2-(4-Cyano-3-trifluoromethyl-phenoxy)-4-methyl-pentanoic acid-(2-m-tolyl-ethyl)amide

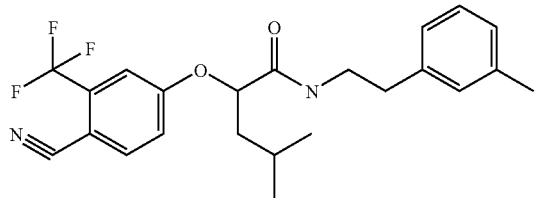

HPLC—Method B
LCMS—Method B

MS: 419.25(M+1 for $C_{23}H_{25}F_3N_2O_2$). Ret. Time: 4.71 min. Purity: 100%.

Example 50

2-(4-Cyano-3-trifluoromethyl-phenoxy)-pentanoic acid-(2-p-tolyl-ethyl)-amide

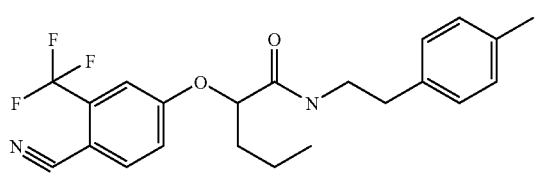

HPLC—Method B
LCMS—Method B

MS: 405.23(M+1 for $C_{22}H_{23}F_3N_2O_2$). Ret. Time: 4.64 min. Purity: 100%.

Example 51

2-(4-Cyano-3-trifluoromethyl-phenoxy)-pentanoic acid-[2-(2-methoxy-phenyl)ethyl]-amide

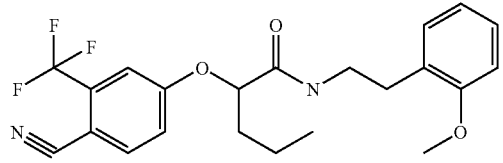

HPLC—Method B
LCMS—Method B

MS: 421.23(M+1 for $C_{22}H_{23}F_3N_2O_3$). Ret. Time: 4.57 min. Purity: 100%.

Example 52

2-(4-Cyano-3-trifluoromethyl-phenoxy)-pentanoic acid-(2-m-tolyl-ethyl)-amide

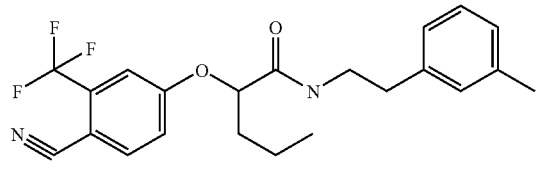

HPLC—Method B
LCMS—Method B

MS: 405.22(M+1 for $C_{22}H_{23}F_3N_2O_2$). Ret. Time: 4.62 min. Purity: 100%.

Example 53

2-(4-Cyano-3-trifluoromethyl-phenoxy)-4-methyl-pentanoic acid-(2-phenoxypropyl)-amide

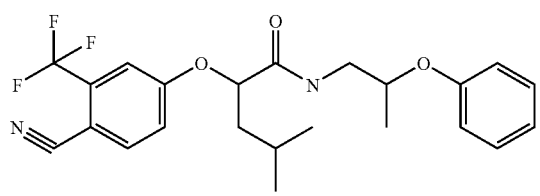

HPLC—Method B
LCMS—Method B

MS: 435.24(M+1 for $C_{23}H_{25}F_3N_2O_3$). Ret. Time: 4.69 min. Purity: 100%.

Example 54

2-(4-Cyano-3-trifluoromethyl-phenoxy)-4-methyl-pentanoic acid indan-1-yl-amide

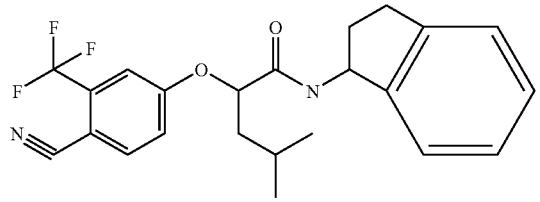

HPLC—Method B
LCMS—Method B

MS: 417.25(M+1 for $C_{23}H_{23}F_3N_2O_2$). Ret. Time: 4.71 min. Purity: 100%.

Example 55

2-(4-Cyano-3-trifluoromethyl-phenoxy)-pentanoic acid-(2-phenoxy-propyl)-amide

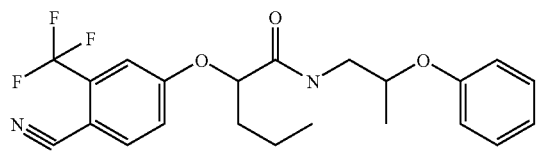

HPLC—Method B
LCMS—Method B
MS: 421.2(M+1 for $C_{22}H_{23}F_3N_2O_3$). Ret. Time: 4.59 min. Purity: 100%.

Example 56

2-(4-Cyano-3-trifluoromethyl-phenoxy)-pentanoic acid-(2-phenoxy-ethyl)-amide

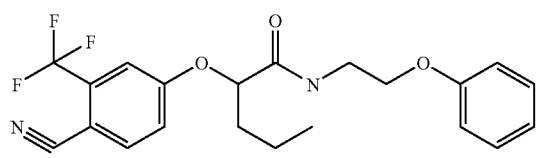

HPLC—Method B
LCMS—Method B
MS: 407.21(M+1 for $C_{21}H_{21}F_3N_2O_3$). Ret. Time: 4.47 min. Purity: 94.67%

Example 57

2-(4-Cyano-3-trifluoromethyl-phenoxy)-pentanoic acid indan-1-yl-amide

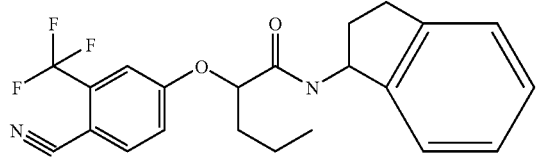

HPLC—Method B
LCMS—Method B
MS: 403.24(M+1 for $C_{22}H_{21}F_3N_2O_2$). Ret. Time: 4.61 min. Purity: 100%.

Example 58

2-(4-Cyano-3-trifluoromethyl-phenoxy)-4-methyl-pentanoic acid-[2-(3-methoxyphenyl)-ethyl]-amide

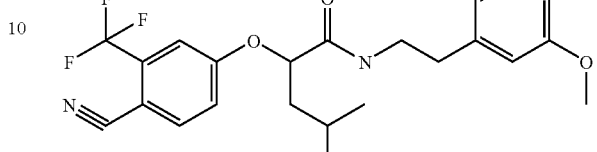

HPLC—Method B
LCMS—Method B
MS: 435.33(M+1 for $C_{23}H_{25}F_3N_2O_3$). Ret. Time: 4.56 min. Purity: 79.59%.

Example 59

2-(4-Cyano-3-trifluoromethyl-phenoxy)-4-methyl-pentanoic acid [2-(1H-indol-3-yl)ethyl]amide

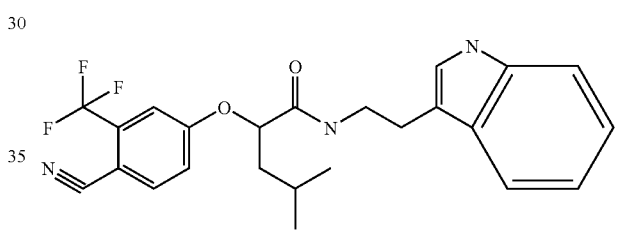

HPLC—Method B
LCMS—Method B
MS: 444.3(M+1 for $C_{24}H_{24}F_3N_3O_2$). Ret. Time: 4.52 min. Purity: 100%.

Example 60

2-(4-Cyano-3-trifluoromethyl-phenoxy)-4-methyl-pentanoic acid (2H-imidazo[1,2-a]pyridin-3-yl)-methyl)amide

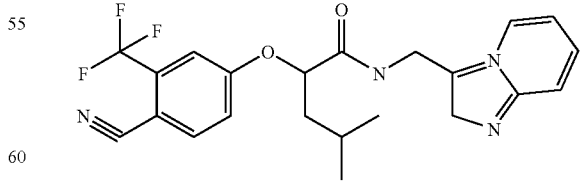

HPLC—Method B
LCMS—Method B
MS: 445.24(M+1 for $C_{23}H_{23}F_3N_4O_2$). Ret. Time: 2.96 min. Purity: 100%.

Example 61

2-(4-Cyano-3-trifluoromethyl-phenoxy)-4-methyl-pentanoic acid-[2-(4-hydroxyphenyl)-ethyl]-amide

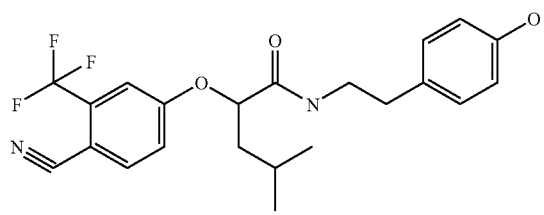

HPLC—Method B
LCMS—Method B

MS: 421.29(M+1 for $C_{22}H_{23}F_3N_2O_3$). Ret. Time: 4.21 min. Purity: 100%

Example 62

2-(4-Cyano-3-trifluoromethyl-phenoxy)-4-methyl-pentanoic acid-(3-pyridin-3-ylpropyl)-amide

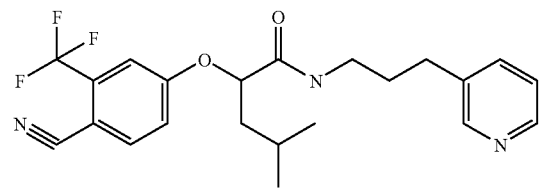

HPLC—Method B
LCMS—Method B

MS: 420.24(M+1 for $C_{22}H_{24}F_3N_3O_2$). Ret. Time: 3.66 min. Purity: 94.76%.

Example 63

2-(4-Cyano-3-trifluoromethyl-phenoxy)-4-methyl-pentanoic acid benzyl-isopropyl-amide

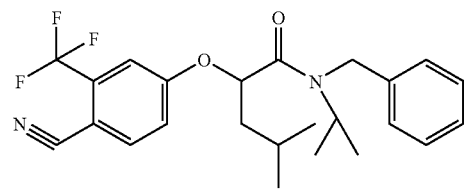

HPLC—Method B
LCMS—Method B

MS: 433.28(M+1 for $C_{24}H_{27}F_3N_2O_2$). Ret. Time: 4.87 min. Purity: 100%.

Example 64

2-(4-Cyano-3-trifluoromethyl-phenoxy)-pentanoic acid-[2-(3-methoxy-phenyl)ethyl]-amide

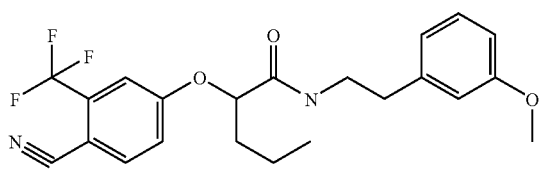

HPLC—Method B
LCMS—Method B

MS: 421.24(M+1 for $C_{22}H_{23}F_3N_2O_3$). Ret. Time: 4.46 min. Purity: 82.38%.

Example 65

2-(4-Cyano-3-trifluoromethyl-phenoxy)-pentanoic acid [2-(1H-indol-3-yl)ethyl]amide

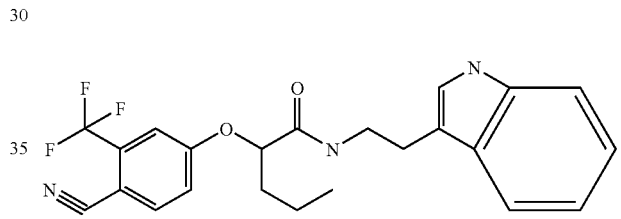

HPLC—Method B
LCMS—Method B

MS: 430.22(M+1 for $C_{23}H_{22}F_3N_3O_2$). Ret. Time: 4.41 min. Purity: 100%.

Example 66

2-(4-Cyano-3-trifluoromethyl-phenoxy)-pentanoic acid-[2-(4-hydroxy-phenyl)ethyl]-amide

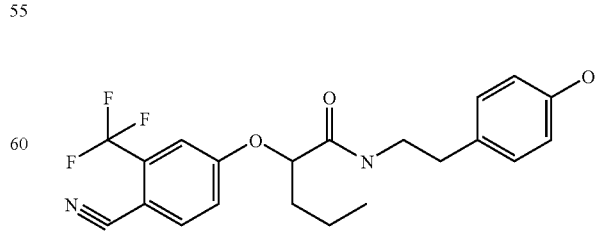

HPLC—Method B
LCMS—Method B

MS: 407.21(M+1 for $C_{21}H_{21}F_3N_2O_3$). Ret. Time: 4.07 min. Purity: 100%.

Example 67

2-(4-Cyano-3-trifluoromethyl-phenoxy)-pentanoic acid benzyl-isopropyl-amide

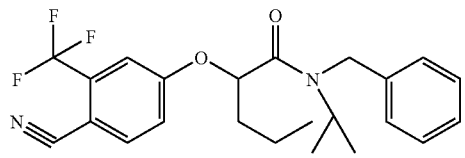

HPLC—Method B
LCMS—Method B

MS: 419.24(M+1 for $C_{23}H_{25}F_3N_2O_2$). Ret. Time: 4.74 min. Purity: 100%.

Example 68

2-(4-Cyano-3-trifluoromethyl-phenoxy)-4-methyl-pentanoic acid (2-dimethylamino-2-phenyl-ethyl)-amide

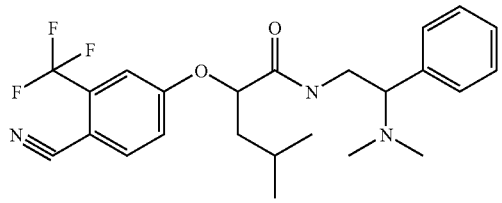

HPLC—Method B
LCMS—Method B

MS: 448.29(M+1 for $C_{24}H_{28}F_3N_3O_2$). Ret. Time: 3.01 min. Purity: 90.27%.

Example 69

2-(4-Cyano-3-trifluoromethyl-phenoxy)-4-methyl-pentanoic acid [1-(4-hydroxyphenyl)-ethyl]-amide

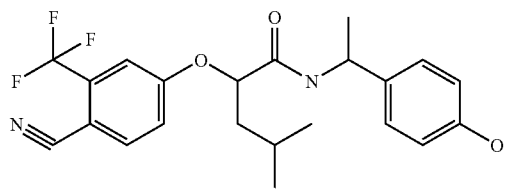

HPLC—Method A
LCMS—Method C

MS: 421.33 (M+1 for $C_{22}H_{23}F_3N_2O_3$). Ret. Time: 3.92 min. Purity: 100%.

Example 70

2-(4-Cyano-3-trifluoromethyl-phenoxy)-4-methyl-pentanoic acid 4-isopropyl-benzylamide

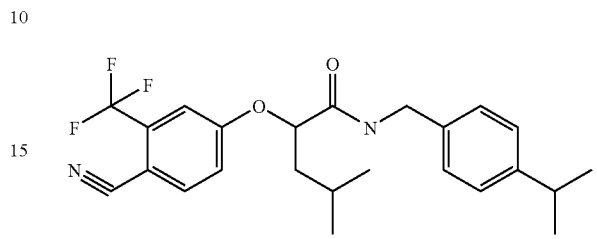

HPLC—Method A
LCMS—Method C

MS: 433.43(M+1 for $C_{24}H_{27}F_3N_2O_2$). Ret. Time: 4.57 min. Purity: 100%.

Example 71

2-(4-Cyano-3-trifluoromethyl-phenoxy)-4-methyl-pentanoic acid-3-methoxy-benzylamide

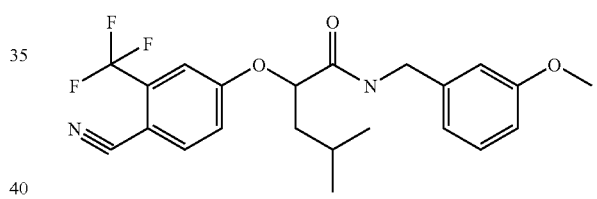

HPLC—Method A
LCMS—Method C

MS: 421.4(M+1 for $C_{22}H_{23}F_3N_2O_3$). Ret. Time: 4.51 min. Purity: 100%.

Example 72

2-(4-Cyano-3-trifluoromethyl-phenoxy)-4-methyl-pentanoic acid-(6-methoxy-pyridin-3-yl-methyl)-amide

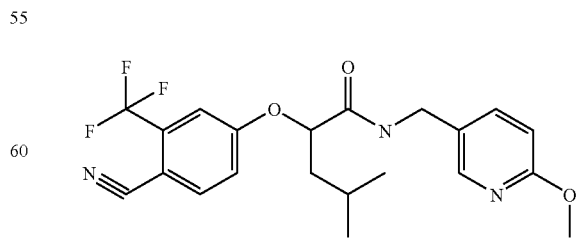

HPLC—Method A
LCMS—Method C

MS: 422.39(M+1 for $C_{21}H_{22}F_3N_3O_3$). Ret. Time: 4.07 min. Purity: 100%.

Example 73

2-(4-Cyano-3-trifluoromethyl-phenoxy)-4-methyl-pentanoic acid-4-methoxy-benzylamide

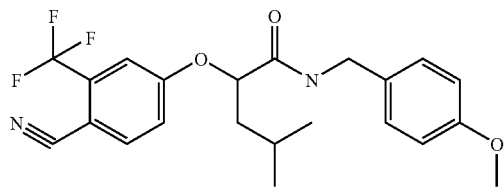

HPLC—Method A
LCMS—Method C

MS: 421.36(M+1 for $C_{22}H_{23}F_3N_2O_3$). Ret. Time: 4.46 min. Purity: 100%.

Example 74

2-(4-Cyano-3-trifluoromethyl-phenoxy)-4-methyl-pentanoic acid-3,4-dihydroxy-benzylamide

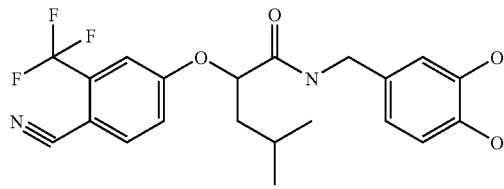

HPLC—Method A
LCMS—Method C

MS: 423.32(M+1 for $C_{21}H_{21}F_3N_2O_4$). Ret. Time: 3.67 min. Purity: 100%.

Example 75

2-(4-Cyano-3-trifluoromethyl-phenoxy)-4-methyl-pentanoic acid-(2-methyl-butyl)amide

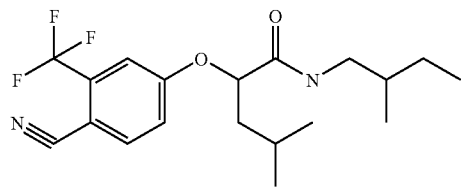

HPLC—Method A
LCMS—Method C

MS: 406.36(M+1 for $C_{21}H_{22}F_3N_3O_2$). Ret. Time: 3.09 min. Purity: 86.9%.

Example 76

2-(4-Cyano-3-trifluoromethyl-phenoxy)-4-methyl-pentanoic acid (2-methyl-pyridin-3-yl-methyl)-amide

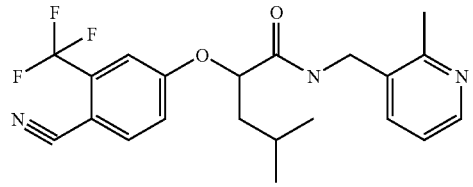

HPLC—Method A
LCMS—Method C

MS: 406.36(M+1 for $C_{21}H_{22}F_3N_3O_2$). Ret. Time: 3.09 min. Purity: 86.9%.

Example 77

2-(4-Cyano-3-trifluoromethyl-phenoxy)-pentanoic acid (naphthalene-1-yl-methyl)amide

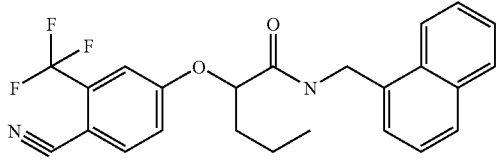

HPLC—Method A
LCMS—Method C

MS: 427.36(M+1 for $C_{24}H_{21}F_3N_2O_2$). Ret. Time: 4.31 min. Purity: 94.82%.

Example 78

2-(4-Cyano-3-trifluoromethyl-phenoxy)-4-methyl-pentanoic acid (3-hydroxy-4-methyl-phenyl)-amide

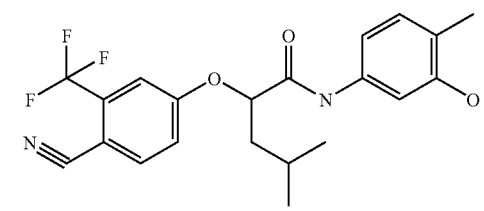

HPLC—Method C
LCMS—Method A

MS: 407.23(M+1 for $C_{21}H_{21}F_3N_2O_3$). Ret. Time: 3.78 min. Purity: 100%.

Example 79

2-(4-Cyano-3-trifluoromethyl-phenoxy)-4-methyl-pentanoic acid (2-hydroxy-ethyl)isopropyl-amide

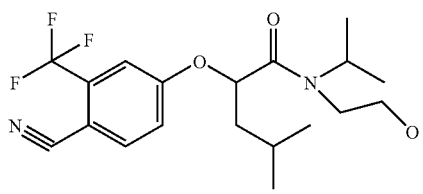

HPLC—Method C
LCMS—Method A
MS: 387.24(M+1 for $C_{19}H_{25}F_3N_2O_3$). Ret. Time: 3.71 min. Purity: 90.41%.

Example 80

2-(4-Cyano-3-trifluoromethyl-phenoxy)-4-methyl-pentanoic acid (3-methylsulfanyl-propyl)-amide

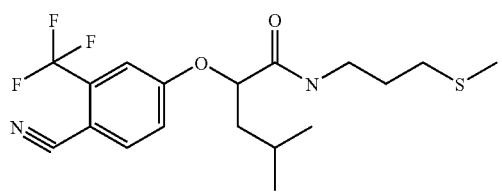

HPLC—Method C
LCMS—Method A
MS: 389.21(M+1 for $C_{18}H_{23}F_3N_2O_2S$). Ret. Time: 3.67 min. Purity: 88.25%.

Example 81

2-(4-Cyano-3-trifluoromethyl-phenoxy)-4-methyl-pentanoic acid (2-propoxy-ethyl)amide

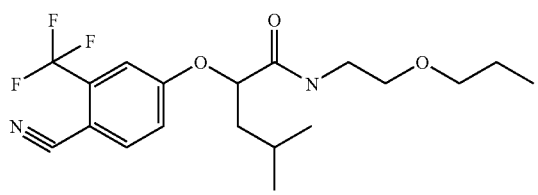

HPLC—Method C
LCMS—Method A
MS: 387.24(M+1 for $C_{19}H_{25}F_3N_2O_3$). Ret. Time: 3.93 min. Purity: 100%.

Example 82

2-(4-Cyano-3-trifluoromethyl-phenoxy)-4-methyl-pentanoic acid (1-methoxymethyl-propyl)-amide

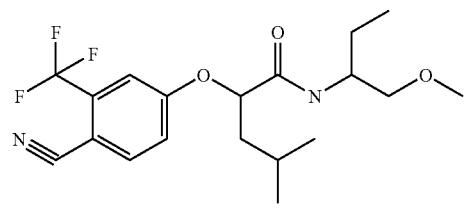

HPLC—Method C
LCMS—Method A
MS: 387.24(M+1 for $C_{19}H_{25}F_3N_2O_3$). Ret. Time: 3.86 min. Purity: 93.3%.

Example 83

2-(4-Cyano-3-trifluoromethyl-phenoxy)-4-methyl-pentanoic acid (2-methylsulfanyl-ethyl)-amide

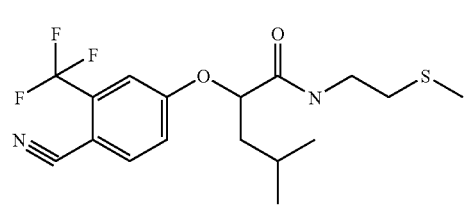

HPLC—Method C
LCMS—Method A
MS: 375.21(M+1 for $C_{17}H_{21}F_3N_2O_2S$). Ret. Time: 3.83 min. Purity: 89.41%.

Example 84

2-(4-Cyano-3-trifluoromethyl-phenoxy)-4-methyl-pentanoic acid (3-hydroxy-2-methyl-phenyl)-amide

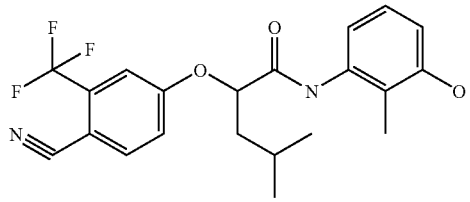

HPLC—Method C
LCMS—Method A
MS: 407.19(M+1 for $C_{21}H_{21}F_3N_2O_3$). Ret. Time: 3.69 min. Purity: 95.35%.

Example 85

2-(4-Cyano-3-trifluoromethyl-phenoxy)-4-methyl-pentanoic acid (3-propoxy-propyl)-amide

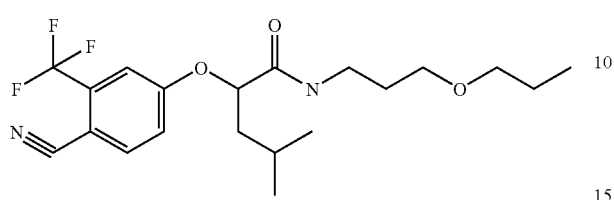

HPLC—Method C
LCMS—Method A
  MS: 401.28(M+1 for $C_{20}H_{27}F_3N_2O_3$). Ret. Time: 4 min. Purity: 100%.

Example 86

2-(4-Cyano-3-trifluoromethyl-phenoxy)-4-methyl-pentanoic acid ethyl(2-methoxyethyl)-amide

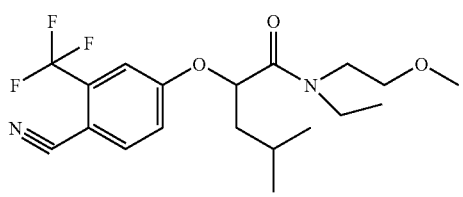

HPLC—Method C
LCMS—Method A
  MS: 387.24(M+1 for C19H25F3N2O$_3$). Ret. Time: 3.97 min. Purity: 92.25%.

Example 87

2-(4-Cyano-3-trifluoromethyl-phenoxy)-4-methyl-pentanoic acid (2-methoxy-phenyl)-amide

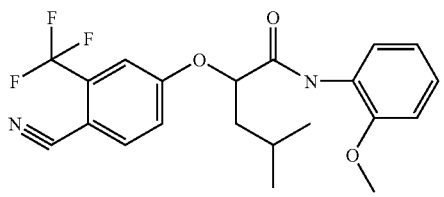

HPLC—Method C
LCMS—Method A
  MS: 407.2(M+1 for $C_{21}H_{21}F_3N_2O_3$). Ret. Time: 4.15 min. Purity: 100%.

Example 88

2-(4-Cyano-3-trifluoromethyl-phenoxy)-4-methyl-pentanoic acid (3-hydroxy-4-methyl-phenyl)-amide

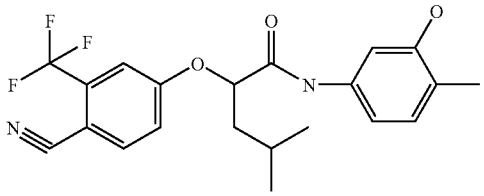

HPLC—Method C
LCMS—Method C
  MS: 393.21(M+1 for $C_{20}H_{19}F_3N_2O_3$). Ret. Time: 3.69 min. Purity: 100%.

Example 89

2-(4-Cyano-3-trifluoromethyl-phenoxy)-pentanoic acid (3-methylsulfanyl-propyl)amide

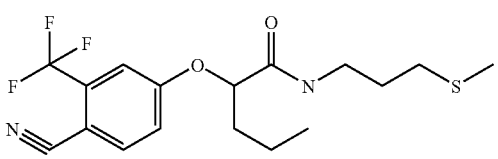

HPLC—Method C
LCMS—Method A
  MS: 375.2(M+1 for $C_{17}H_{21}F_3N_2O_2S$). Ret. Time: 3.75 min. Purity: 96.91%.

Example 90

2-(4-Cyano-3-trifluoromethyl-phenoxy)-pentanoic acid (2-methylsulfanyl-ethyl)amide

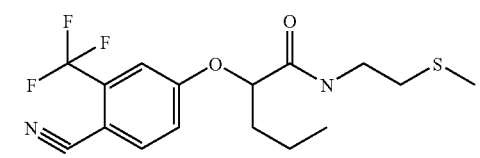

HPLC—Method C
LCMS—Method A
  MS: 361.21(M+1 for $C_{16}H_{19}F_3N_2O_2S$). Ret. Time: 3.72 min. Purity: 94.75%.

Example 91

2-(4-Cyano-3-trifluoromethyl-phenoxy)-hexanoic acid benzylamide

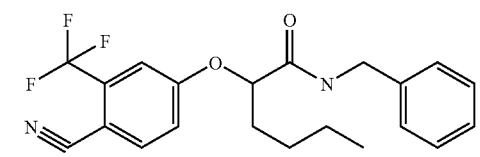

The product of Example 91 is prepared analogously to example 1, except in step 1, ethyl-DL-2-hydroxy-cuproate is used instead of DL-leucic acid isopropyl ester as one of the starting materials. The desired product is purified by silica gel column.

MS: 391 (M+1 for $C_{21}H_{21}N_2F_3O_2$) LCMS: C-18 Column (25% $H_2O$/75% $CH_3CN$), Ret. Time: 1.51 min Purity: 100%.

Example 92

N-Benzyl-2-(4-Cyano-3-trifluoromethyl-phenoxy)-3-methyl-butyramide

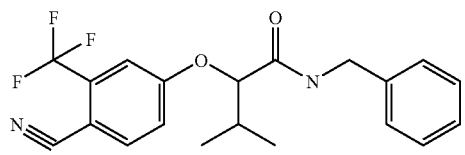

The product of Example 92 is prepared analogously to example 1, except in step 1, DL-2-hydroxy-3-methylbutyric acid is used instead of DL-leucic acid isopropyl ester as one of the starting materials. The desired product is purified by silica gel column.

MS: 377 (M+1 for $C_{20}H_{19}N_2F_3O_2$) LCMS: C-18 Column (25% $H_2O$/75% $CH_3CN$), Ret. Time: 2.9 min Purity: 100%.

Example 93

N-Benzyl-2-(4-Cyano-3-trifluoromethyl-phenoxy)-butyramide

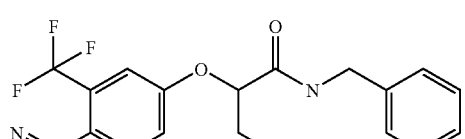

The product of Example 93 is prepared analogously to example 1, except in step 1, DL-2-hydroxy-n-butyric acid ethyl ester is used instead of DL-leucic acid isopropyl ester as one of the starting materials. The desired product is purified by silica gel column.

MS: 363 (M+1 for $C_{19}H_{17}N_2F_3O_2$) LCMS: C-18 Column (25% $H_2O$/75% $CH_3CN$), Ret. Time: 1.07 min Purity: 100%.

Example 94

(R)-2-(4-Cyano-3-trifluoromethyl-phenoxy)-4-methyl-pentanoic acid benzylamide

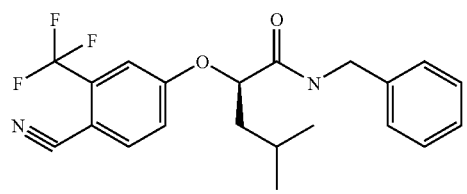

The product of Example 94 was prepared by chiral HPLC separation of the product of Example 1. The desired product was purified by LCMS as described below.

MS: 391.1 (M+1 for $C_{21}H_{21}N_2F_3O_2$) LCMS: C-18 Column (25% $H_2O$/75% $CH_3CN$), Ret. Time: 1.46 min Purity: 100%. $[\alpha]_{589(MeOH)}=+37°$.

Example 95

(R)-2-(4-Cyano-3-trifluoromethyl-phenoxy)-pentanoic acid benzylamide

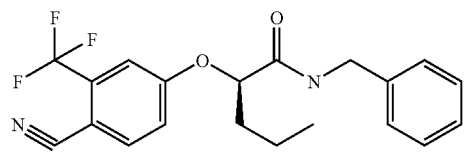

The product of Example 95 was prepared by chiral HPLC separation of the product of Example 4.

MS: 377.1 (M+1 for $C_{20}H_{19}N_2F_3O_2$) LCMS: C-18 Column (25% $H_2O$/75% $CH_3CN$), Ret. Time: 1.31 min Purity: 100%. $[\alpha]_{589(MeOH)}=+32°$.

Example 96

(R)-2-(Cyano-3-trifluoromethyl-phenoxy)-pentanoic acid 2-methyl-benzylamide

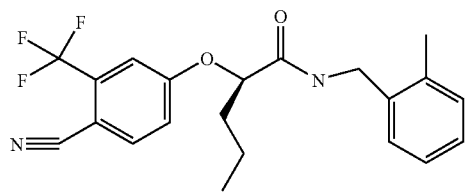

The product of Example 96 was prepared by chiral HPLC separation of the product of Example 44.
Column: ChiralPak AD.
Hexane 80%/IPA 20%
Flow rate: 0.5 mL/min.
Retention time: 10.63 min.
$[\alpha]589(MeOH)=+21.73°$

Example 97

2-(4-Cyano-3-trifluoromethyl-phenoxy)-pentanoic acid [2-(5-methoxy-1H-indol-3-yl)-ethyl]-amide

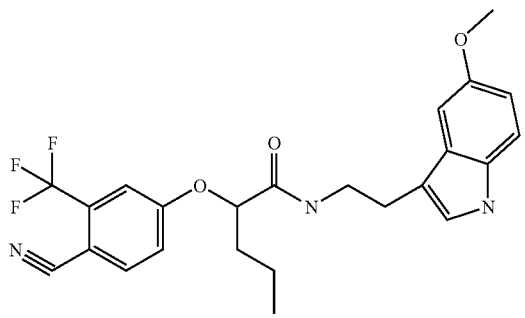

The compound was prepared in the following manner. To 0.25 gm (0.87 mmol) of 2-(4-cyano-3-trifluoromethyl-phenoxy)-pentanoic acid in dimethylformamdie "DMF" (15 mL) were added 0.14 gm (1.09 mmol) of 1-Hydroxy-benzotriazole HOBT, 0.2 gm (1.09 mmol) of (3-(dimethylamino)propyl)ethylcarbodiimide EDCl, 0.23 gm (2.39 mmol) N-methyl morpholine, and approximately 246 mg of 5-methoxytryptamine hydrochloride (1.09 mmol). The resultant mixtures were stirred at room temperature for approximately 18 hours. The reactions were quenched with sodium bicarbonate (20 mL) and extracted with ethyl acetate (3 times 20 mL). The solvent was removed in vacuo to obtain oils that were then purified by HPLC.

Prep HPLC Conditions
A: Water w/0.1% $NH_4OH$
B: Acetonitrile w/0.1% $NH_4OH$
5% to 95% B over 15 min.
1 min. ramp to 5% B, hold for 5 min.
Xterra $C_{18}$ 5 υμ, 4.6×150 mm
Retention time: 12.3 min.

Example 98

2-(4-Cyano-3-trifluoromethyl-phenoxy)-4-methyl-pentanoic acid [2-(5-methoxy-1H-indol-3-yl)-ethyl]-amide

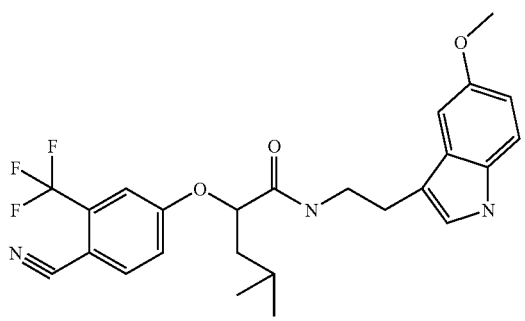

The compound was prepared in the following manner. To 0.25 gm (0.83 mmol) of 2-(4-cyano-3-trifluoromethyl-phenoxy)-4-methyl-pentanoic acid in dimethylformamdie "DMF" (15 mL) were added 0.14 gm (1.04 mmol) of 1-Hydroxy-benzotriazole HOBT, 0.2 gm (1.04 mmol) of (3-(dimethylamino)propyl)ethylcarbodiimide EDCl, 0.23 gm (2.28 mmol) N-methyl morpholine, and approximately 234 mg of 5-methoxytryptamine hydrochloride (1.04 mmol). The resultant mixtures were stirred at room temperature for approximately 18 hours. The reactions were quenched with sodium bicarbonate (20 mL) and extracted with ethyl acetate (3 times 20 mL). The solvent was removed in vacuo to obtain oils that were then purified by HPLC.

Prep HPLC Conditions
A: Water w/0.1% $NH_4OH$
B: Acetonitrile w/0.1% $NH_4OH$
5% to 95% B over 15 min.
1 min. ramp to 5% B, hold for 5 min.
Xterra $C_{18}$ 5 υμ, 4.6×150 mm
Retention time: 12.8 min.

Example 99

2-(3-Chloro-4-cyano-phenoxy)-pentanoic acid ethyl ester

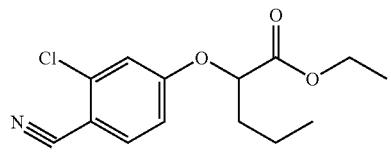

The product of Example 99 is prepared analogously to example 1 step 1, except 2-hydroxy-pentanoid acid ethyl ester is used instead of DL-leucic acid isopropyl ester as one of the starting materials and 2-chloro-4-fluoro-benzonitrile is used instead of 4-fluoro-2-trifluoromethyl-benzonitrile. The desired product is purified by column to yield an oily liquid as the pure product.

MS: 282.1 M+1 for ($C_{14}H_{11}ClNO_3$) LCMS: C-18 column (25% $H_2O$/75% $CH_3CN$. RT=1.28 min. Purity 100%

Example 100

2-(2-Chloro-4-cyano-phenoxy)-pentanoic acid ethyl ester

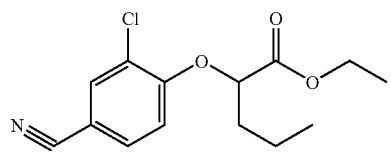

The product of Example 100 is prepared analogously to example 1 step 1, except 2-hydroxy-pentanoid acid ethyl ester is used instead of DL-leucic acid isopropyl ester as one of the starting materials and 3-chloro-4-fluoro-benzonitrile is used instead of 4-fluoro-2-trifluoromethyl-benzonitrile. The desired product is purified by column to yield a white solid as the pure product.

MS: 282.1 M+1 for (C$_{14}$H$_{16}$ClNO$_3$) LCMS: C-18 column (25% H$_2$O/75% CH$_3$CN. RT=1.25 min. Purity 100%

Example 101

2-(3-Chloro-4-cyano-phenoxy)-pentanoic acid [2-(1H-indol-3-yl)-ethyl]-amide

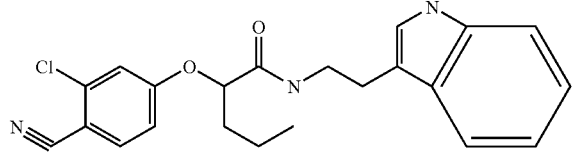

The product of Example 101 is prepared analogously to example 1, except: 1) in step 1, DL-2-hydroxy-pentanoic acid ethyl ester is used instead of DL-leucic acid isopropyl ester as one of the starting materials, 2) in step 1, 4-fluoro-2-chloro-benzonitrile is used in place of 4-fluoro-2-trifluoromethyl-benzonitrile and 3) in step 3, 1-[3-(dimethylamino)propyl]-3-ethylcarbodiimide hydrochloride, 1-hydroxy-benzotriazole, N-methylmorpholine and aminobenzylamine are used as the base/coupling agent. The desired product was purified by silica gel column.

MS: 396.2 (M+1 for C$_{22}$H$_{22}$ClN$_3$O$_2$) LCMS: C-18 column (25% H$_2$O/75% CH$_3$CN RT=1.13 min. Purity 95.5%

Example 102

2-(3-Chloro-4-cyano-phenoxy)-pentanoic acid benzylamide

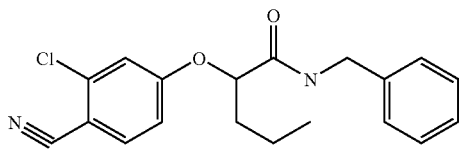

The product of Example 102 is prepared analogously to example 1, except: 1) in step 1, DL-2-hydroxy-pentanoic acid ethyl ester is used instead of DL-leucic acid isopropyl ester as one of the starting materials, 2) in step 1, 4-fluoro-2-chloro-benzonitrile is used in place of 4-fluoro-2-trifluoromethyl-benzonitrile and 3) in step 3, 1-[3-(dimethylamino)propyl]-3-ethylcarbodiimide hydrochloride, 1-hydroxy-benzotriazole, N-methylmorpholine and aminobenzylamine are used as the base/coupling agent. The desired product was purified by silica gel column.

MS: 343.1 (M+1 for C$_{19}$H$_{19}$ClN$_2$O$_2$) LCMS: C-18 column (25% H$_2$O/75% CH$_3$CN. RT=1.20 min Purity 99.5%

Example 103

2-(3-Chloro-4-cyano-phenoxy)-pentanoic acid [2-(4-hydroxy-phenyl)-ethyl]-amide

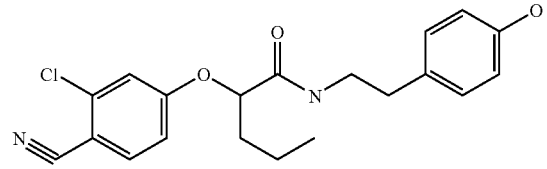

The product of Example 103 is prepared analogously to example 1, except: 1) in step 1, DL-2-hydroxy-pentanoic acid ethyl ester is used instead of DL-leucic acid isopropyl ester as one of the starting materials, 2) in step 1, 4-fluoro-2-chloro-benzonitrile is used in place of 4-fluoro-2-trifluoromethyl-benzonitrile and 3) in step 3, 1-[3-(dimethylamino)propyl]-3-ethylcarbodiimide hydrochloride, 1-hydroxy-benzotriazole, N-methylmorpholine and aminobenzylamine are used as the base/coupling agent. The desired product was purified by silica gel column.

MS: 373.2 (M+1 for C$_{20}$H$_{21}$ClN$_2$O$_3$) LCMS: C-18 column (25% H$_2$O/75% CH$_3$CN. RT=0.97 min. Purity 99.9%

Example 104

(S)-2-(3-Chloro-4-cyano-phenoxy)-pentanoic acid benzylamide

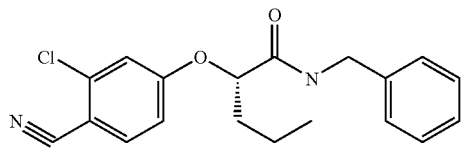

The product of Example 104 was prepared by chiral HPLC separation of the product of Example 102.

MS: 343.1 (M+1 for C$_{19}$H$_{19}$ClN$_2$O$_2$) LCMS: C-18 column (25% H$_2$O/75% CH$_3$CN. RT=1.23 min Purity 100%

Example 105

(S)-2-(3-Chloro-4-cyano-phenoxy)-pentanoic acid [2-(4-hydroxy-phenyl)ethyl]amide

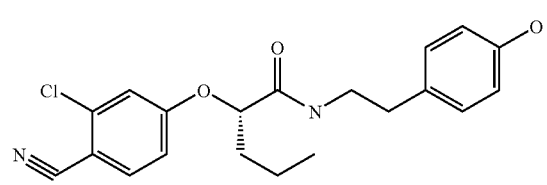

The product of Example 105 was prepared by chiral HPLC separation of the product of Example 103. MS: 373.1(M+1 for C$_{20}$H$_{21}$ClN$_2$O$_3$) LCMS: C-18 column (25% H$_2$O/75% CH$_3$CN. RT=0.91 min. Purity 99.9%

Example 106

(S)-2-(3-Chloro-4-cyano-phenoxy)-pentanoic acid [2-(1H-indol-3-yl)-ethyl]-amide

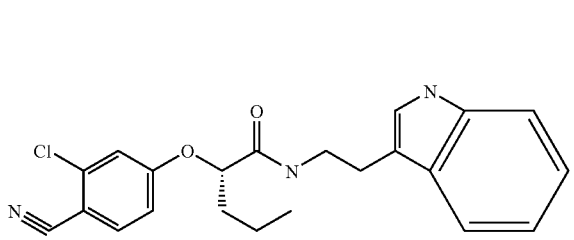

The product of Example 106 was prepared by chiral HPLC separation of the product of Example 101.

MS: 396.1 (M+1 for C$_{22}$H$_{22}$ClN$_3$O$_2$) LCMS: C-18 column (25% H$_2$O/75% CH$_3$CN RT=1.11 min. Purity 100%

Example 107

(S)-2-(4-Cyano-3-trifluoromethyl-phenoxy)-pentanoic acid-3-methyl-benzylamide

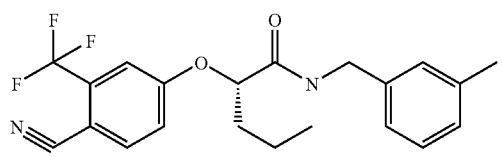

The product of Example 107 was prepared by chiral HPLC separation of the product of Example 43.

MS: 391.2 (M+1 for C$_{21}$H$_{21}$F$_3$N$_2$O$_2$) LCMS: C-18 column (25% H$_2$O/75% CH$_3$CN. RT=1.43 min. Purity 100%

Example 108

(S)-2-(4-Cyano-3-trifluoromethyl-phenoxy)-pentanoic acid [2-(1H-indol-3-yl)ethyl]-amide

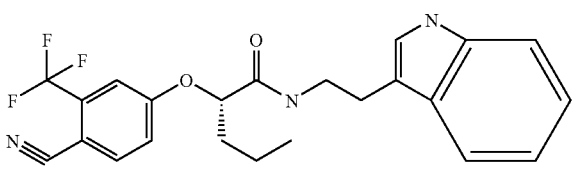

The product of Example 108 was prepared by chiral HPLC separation of the product of Example 65.

MS: 430.1 (M+1 for C$_{23}$H$_{22}$F$_3$N$_3$O$_2$) LCMS: C-18 column (25% H$_2$O/75% CH$_3$CN. RT=1.24 min. Purity 100%

Example 109

(S)-2-(4-cyano-3-trifluoromethyl-phenoxy)-4-methyl-pentanoic acid-[2-(4-hydroxy-phenyl)-ethyl]-amide

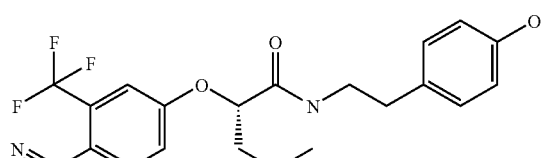

The product of Example 109 was prepared by chiral HPLC separation of the product of Example 61.

MS: 407.2 (M+1 for C$_{21}$H$_{21}$F$_3$N$_2$O$_3$) LCMS: C-18 column (50% H$_2$O/50% CH$_3$CN. RT=0.94 min Purity 99.9%

Example 110

2-(4-Cyano-3-trifluoromethyl-phenoxy)-4-methyl-pentanoic acid [1-(4-methoxy-phenyl)-ethyl]-amide

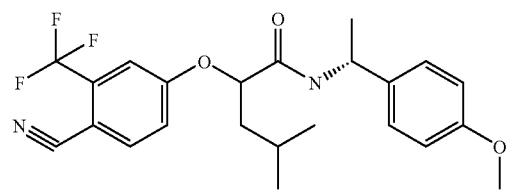

The product of Example 110 is prepared analogously to example 1, except: 1) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 2) 1-4-methoxyphenyl)-ethylamine is used instead of benzylamine. The desired product is purified by silica gel column.

MS: 435.1 (C$_{23}$H$_{25}$F$_3$N$_2$O$_3$) LCMS: C-18 column (25% H$_2$O/75% CH$_3$CN. RT=1.48 min. Purity 99.9%

Example 111

(R—)2(4-Cyano-3-trifluoromethyl-phenoxy)-4-methyl-pentanoic acid [2-4-hydroxyphenyl)-ethyl]-amide

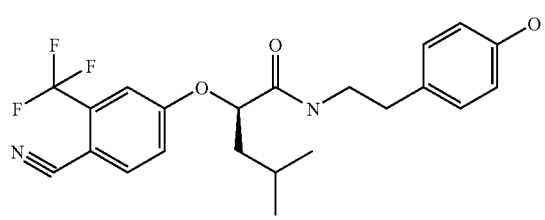

The product of Example 111 was prepared by chiral HPLC separation of the product of Example 61.

MS: 421.2 (M+1C$_{22}$H$_{23}$F$_3$N$_2$O$_3$) LCMS: C-18 column (50% H$_2$O/750 CH$_3$CN. RT=2.55 min. Purity 100%

Example 112

2-(4-Cyano-3-trifluoromethyl-phenoxy)-4-methyl-pentanoic acid (1-phenyl-ethyl)-amide

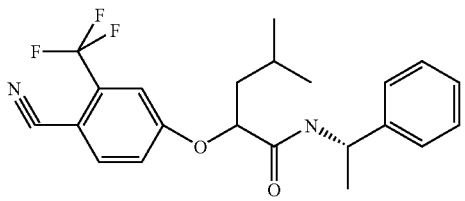

The product of Example 112 is prepared analogously to example 1, except: 1) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 2) 1-phenyethylamine is used instead of benzylamine. The desired product is purified by silica gel column.

MS: 405.1 (M+1 for $C_{22}H_{23}F_3N_2O_2$) LCMS: C-18 column (25% $H_2O$/75% $CH_3CN$. RT=1.51 min Purity 100%

Example 113

2-(4-Cyano-3-trifluoromethyl-phenoxy)-pentanoic acid [1-(4-methoxy-phenyl)-ethyl]-amide

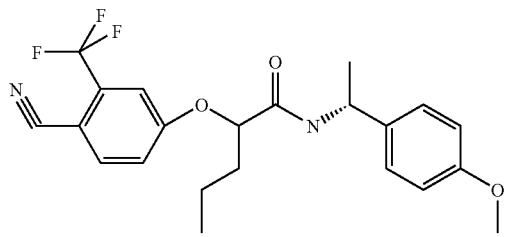

The product of Example 113 is prepared analogously to example 1, except: 1) in step 1, DL-2-hydroxy-pentanoic acid ethyl ester is used instead of DL-leucic acid isopropyl ester as one of the starting materials, 2) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 3) 1-(4-methoxy-phenyl)-ethylamine is used instead of benzylamine. The desired product is purified by silica gel column:

MS: 421.1 (M+1 for $C_{22}H_{23}F_3N_2O_3$) LCMS: C-18 column (25% $H_2O$/75% $CH_3CN$. RT=1.26 min. Purity 100%

Example 114

2-(4-Cyano-3-trifluoromethyl-phenoxy)-4-methyl-pentanoic acid (2-ethyl sulfanyl-ethyl)-amide

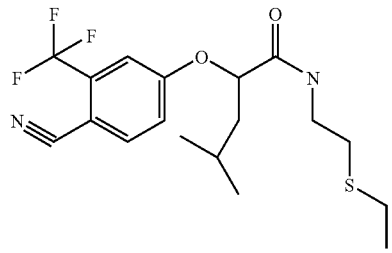

The product of Example 114 is prepared analogously to example 1, except: 1) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 2) 2-ethylsulfanyl-ethylamine is used instead of benzylamine. The desired product is purified by silica gel column
MS: 389.1M+1 for ($C_{18}H_{23}F_3N_2O_2S$)

Example 115

2-(4-Cyano-3-trifluoromethyl-phenoxy)-pentanoic acid (3-propoxy-propyl)-amide

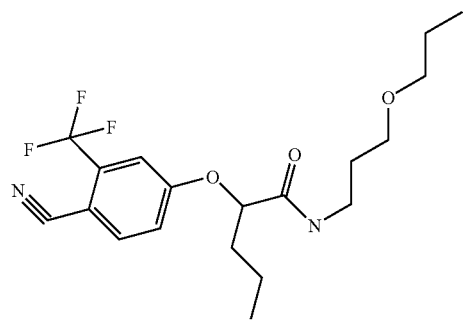

HPLC—Method C
LCMS—Method A
MS 387.24 (M+1 for $C_{19}H_{25}F_3N_2O_3$ Ret Time 3.9 min. Purity: 100%

Example 116

2-(4-Cyano-3-trifluoromethyl-phenoxy)-pentanoic acid (3-hydroxy-4-methyl-phenyl)-amide

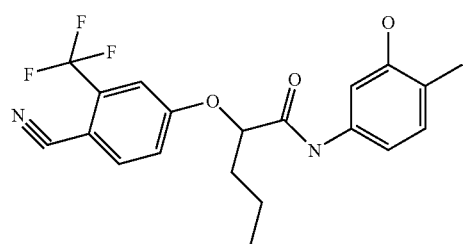

HPLC—Method C
LCMS—Method A

MS 393.21 (M+1) for $C_{20}H_{19}F_3NO_3$ Ret. Time 3.63 min. Purity 100%

Example 117

2-(4-Cyano-3-trifluoromethyl-phenoxy)-4-methyl-pentanoic acid [1-(4-hydroxy-phenyl)-ethyl]-amide

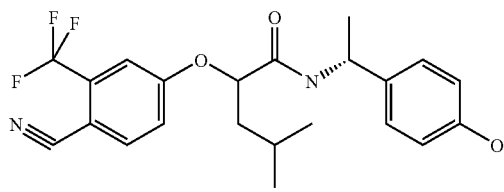

The product of Example 117 is prepared analogously to example 1, except: 1) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 2) 4-(1-aminoethyl)phenol is used instead of benzylamine. The desired product is purified by silica gel column.

MS: 421.1 (M+1 for $C_{22}H_{23}F_3N_2O_3$) LCMS: C-18 column (25% $H_2O$/75% $CH_3CN$. RT=1.03 min. Purity 100%

Example 118

2-(4-Cyano-3-trifluoromethyl-phenoxy)-pentanoic acid [1-(4-hydroxy-phenyl)-ethyl]-amide

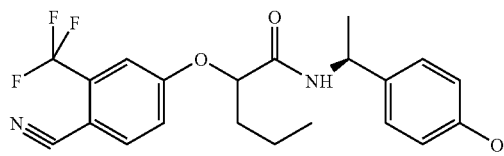

The product of Example 118 is prepared analogously to example 1, except: 1) in step 1, DL-2-hydroxy-pentanoic acid ethyl ester is used instead of DL-leucic acid isopropyl ester as one of the starting materials, 2) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 3) 4-(1-amino-ethyl)-phenol is used instead of benzylamine. The desired product is purified by silica gel column:

MS: 407.1 (M+1 for $C_{21}H_{21}F_3N_2O_3$) LCMS: C-18 column (25% $H_2O$/75% $CH_3CN$. RT=0.94 min. Purity 99.9%

Example 119

2-(4-Cyano-3-trifluoromethyl-phenoxy)-pentanoic acid [1-(4-hydroxy-phenyl)-ethyl]-amide

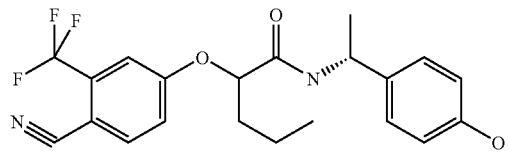

The product of Example 119 is prepared analogously to example 1, except: 1) in step 1, DL-2-hydroxy-pentanoic acid ethyl ester is used instead of DL-leucic acid isopropyl ester as one of the starting materials, 2) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 3) 4-(1-amino-ethyl)-phenol is used instead of benzylamine. The desired product is purified by silica gel column:

MS: 407.1 (M+1 for $C_{21}H_{21}F_3N_2O_3$) LCMS: C-18 column (25% $H_2O$/75% $CH_3CN$. RT=0.98 min. Purity 99.9%

Example 120

2-(4-Cyano-3-trifluoromethyl-phenoxy)-4-methyl-pentanoic acid [1-(4-hydroxy-phenyl)-ethyl]-amide

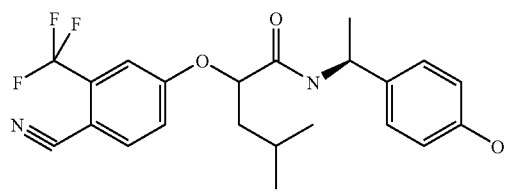

The product of Example 117 is prepared analogously to example 1, except: 1) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 2) 4-(1-aminoethyl)phenol is used instead of benzylamine. The desired product is purified by silica gel column.

MS: 421.1 (M+1 for $C_{22}H_{23}F_3N_2O_3$) LCMS: C-18 column (25% $H_2O$/75% $CH_3CN$. RT=1.10 min. Purity 100%

Example 121

2-(4-Cyano-3-trifluoromethyl-phenoxy)-4-methyl-pentanoic acid [1-(4-methoxy-phenyl)-ethyl]-amide

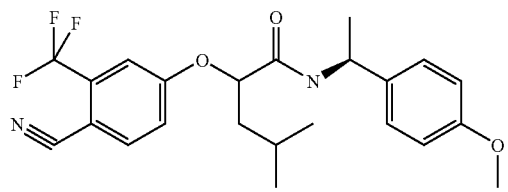

The product of Example 121 is prepared analogously to example 1, except: 1) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 2) 1-(4-methoxyphenyl)-ethylamine is used instead of benzylamine. The desired product is purified by silica gel column:

MS: 435.2 (M+1 for $C_{23}H_{25}F_3N_2O_3$ LCMS—C-18 column (25% $H_2O$/75% $CH_3CN$. RT=1.49 min. Purity 98.5%

Example 122

2-(4-Cyano-3-trifluoromethyl-phenoxy)-4-methyl-pentanoic acid (1-phenyl-ethyl)-amide

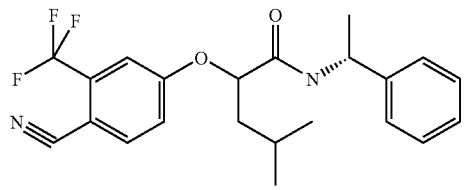

The product of Example 122 is prepared analogously to example 1, except: 1) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 2) 1-phenyl ethylamine is used instead of benzylamine. The desired product is purified by silica gel column.

MS: 405.1 (M+1 for $C_{23}H_{23}F_3N_2O_2$ LCMS—C-18 column (25% $H_2O$/75% $CH_3CN$. RT=1.60 min. Purity 99.5%

Example 123

2-(4-Cyano-3-trifluoromethyl-phenoxy)-pentanoic acid [1-(4-methoxy-phenyl)-ethyl]-amide

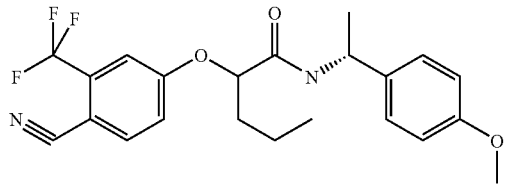

The product of Example 123 is prepared analogously to example 1, except: 1) in step 1, DL-2-hydroxy-pentanoic acid ethyl ester is used instead of DL-leucic acid isopropyl ester as one of the starting materials, 2) in step 3, 1-[3-(dimethylamino)propyl]-3-ethylcarbodiimide hydrochloride, 1-hydroxy-benzotriazole, N-methylmorpholine and aminobenzylamine are used as the base/coupling agent and 3) 1-(4-methoxy-phenyl)-ethylamine is used instead of benzylamine. The desired product is purified by silica gel column.

MS: 421.1 ($C_{22}H_{23}F_3N_2O_3$) LCMS: C-18 column (25% $H_2O$/75% $CH_3CN$. RT=1.26 min Purity 100%

Example 124

The compounds of Formula I have affinity for the androgen receptor. This affinity has been demonstrated for selected compounds using the human receptor. The description below describes how the assay was carried out.

Competitive binding analysis was performed on baculovirus/Sf9 generated hAR extracts in the presence or absence of different concentrations of test agent and a fixed concentration of $^3H$-dihydrotestosterone ($^3H$-DHT) as tracer. This binding assay method is a modification of a protocol previously described (Liao S., et. al. *J. Steroid Biochem.* 20:11-17 1984). Briefly, progressively decreasing concentrations of compounds are incubated in the presence of hAR extract (Chang et al. *P.N.A.S.* Vol. 89, pp. 5546-5950, 1992), hydroxylapatite, and 1 nM$^3H$-DHT for one hour at 4° C. Subsequently, the binding reactions are washed three times to completely remove excess unbound $^3H$-DHT. hAR bound $^3H$-DHT levels are determined in the presence of compounds (=i.e competitive binding) and compared to levels bound when no competitor is present (=i.e. maximum binding). Compound binding affinity to the hAR is expressed as the concentration of compound at which one half of the maximum binding is inhibited. Table II below provides the results that were obtained for selected compounds (reported data is the mean of multiple tests as shown below)

TABLE II

| Example # | Structure | AR Binding $IC_{50\,(nM)}$ |
| --- | --- | --- |
| 1 | ![structure] | 95 (c) |

TABLE II-continued

| Example # | Structure | AR Binding IC$_{50}$ (nM) |
|---|---|---|
| 2 | 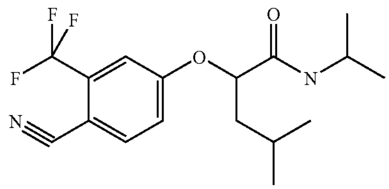 | 64 (a) |
| 3 | 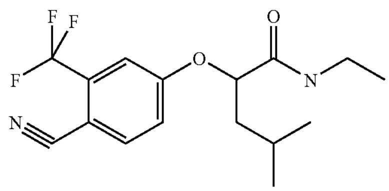 | 247 (a) |
| 4 | 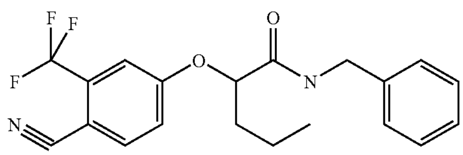 | 445<br>N = 8 |
| 5 | 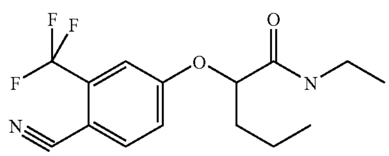 | 277 (a) |
| 6 | 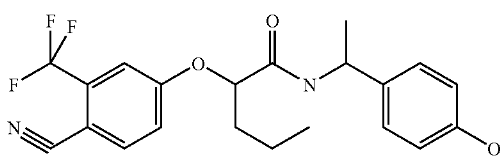 | 455 (a) |
| 7 | 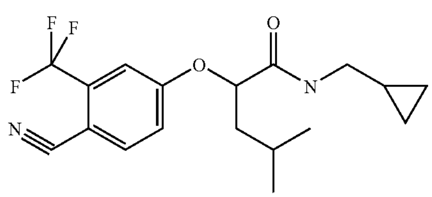 | 107 (a) |
| 8 | 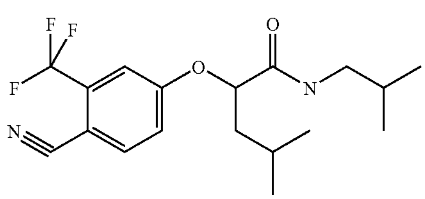 | 58 (a) |
| 9 | 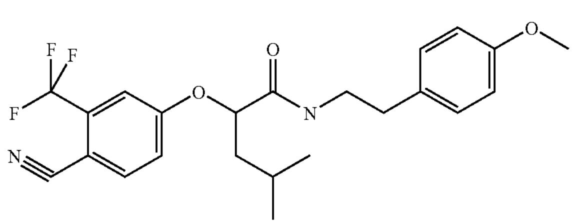 | 163 (a) |

TABLE II-continued

| Example # | Structure | AR Binding IC$_{50}$ (nM) |
|---|---|---|
| 10 | 4-cyano-3-(trifluoromethyl)phenoxy-4-methyl-N-(2-phenoxyethyl)pentanamide | 91 (a) |
| 11 | 4-cyano-3-(trifluoromethyl)phenoxy-N-(furan-2-ylmethyl)-4-methylpentanamide | 172 (a) |
| 12 | 4-cyano-3-(trifluoromethyl)phenoxy-4-methyl-N-(thiophen-2-ylmethyl)pentanamide | 86 (a) |
| 13 | 4-cyano-3-(trifluoromethyl)phenoxy-4-methyl-N-(1-(thiophen-2-yl)ethyl)pentanamide | 240 (a) |
| 14 | 4-cyano-3-(trifluoromethyl)phenoxy-4-methyl-N-(1-(thiophen-2-yl)ethyl)pentanamide | 197 (a) |
| 15 | 4-cyano-3-(trifluoromethyl)phenoxy-4-methyl-N-(1-(pyridin-3-yl)ethyl)pentanamide | 309 (a) |
| 16 | 4-cyano-3-(trifluoromethyl)phenoxy-4-methyl-N-(pyridin-4-ylmethyl)pentanamide | 368 (c) |
| 17 | 4-cyano-3-(trifluoromethyl)phenoxy-N-(1-(thiophen-2-yl)ethyl)pentanamide | 1002 (a) |

TABLE II-continued

| Example # | Structure | AR Binding IC$_{50}$ (nM) |
|---|---|---|
| 18 | 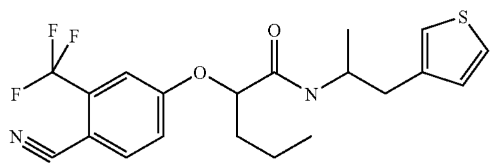 | 222 (a) |
| 19 | 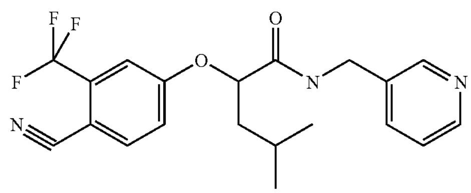 | 131 (a) |
| 20 | 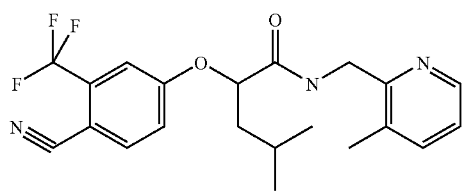 | 410 (a) |
| 21 | 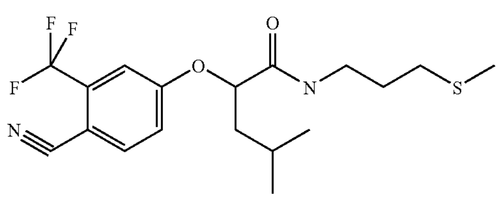 | 362 (a) |
| 22 | 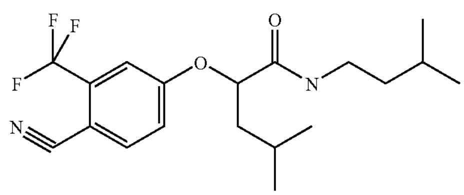 | 178 (a) |
| 23 | 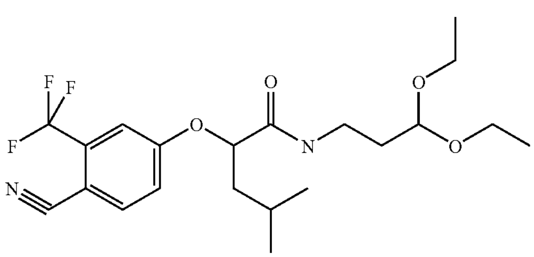 | UA |
| 24 | 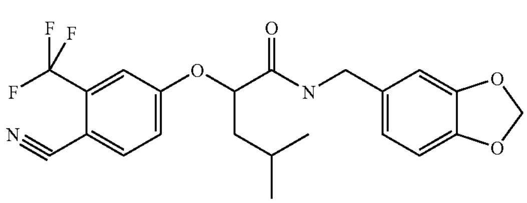 | 56 (a) |

TABLE II-continued

| Example # | Structure | AR Binding IC$_{50\,(nM)}$ |
|---|---|---|
| 25 | 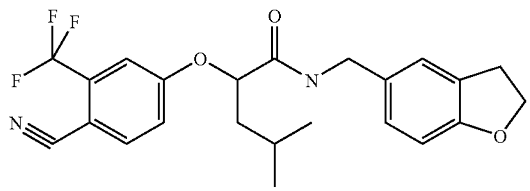 | 67 (c) |
| 26 | 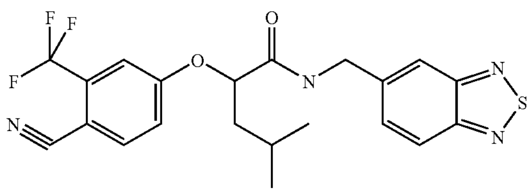 | 67 (a) |
| 27 | 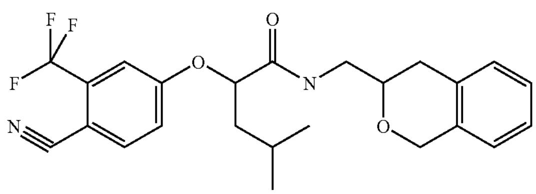 | 214 (a) |
| 29 | 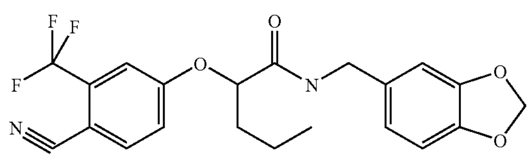 | 180 (a) |
| 30 | 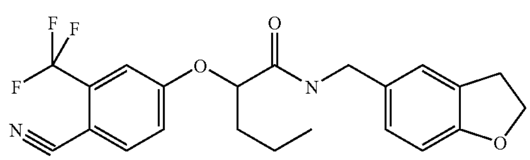 | 134 (a) |
| 31 | 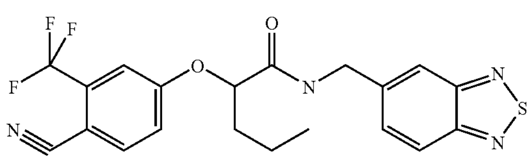 | 83 (a) |
| 32 | 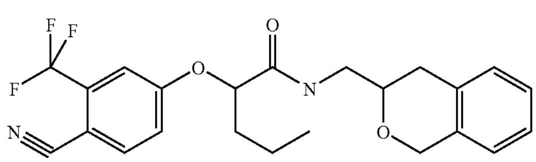 | 407 (a) |
| 33 | 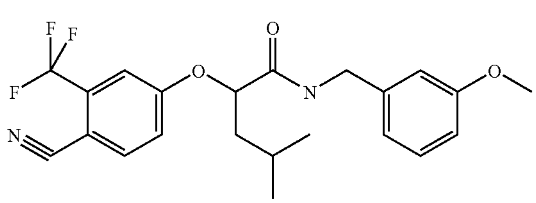 | 62 (a) |

TABLE II-continued

| Example # | Structure | AR Binding IC$_{50\ (nM)}$ |
|---|---|---|
| 34 | 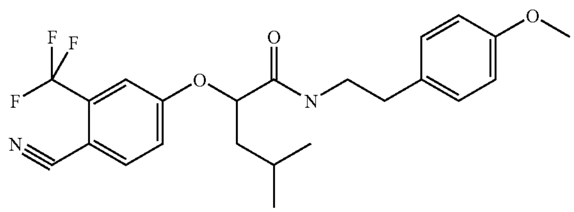 | 68 (a) |
| 35 | 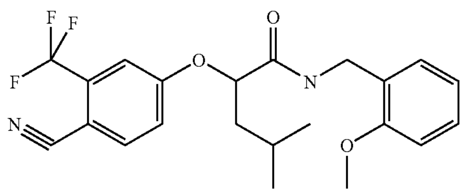 | 77 (a) |
| 36 | 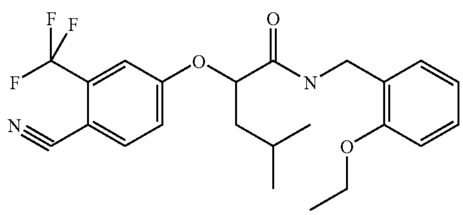 | 42 (a) |
| 37 | 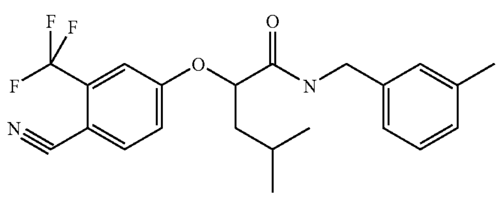 | 41 (a) |
| 38 | 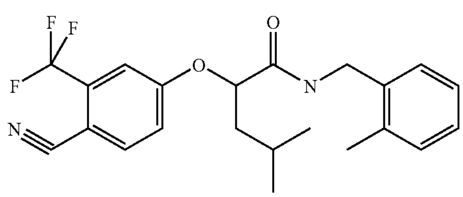 | 15 (a) |
| 39 | 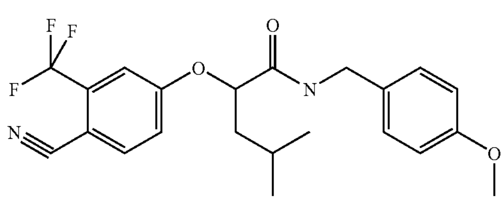 | 42 (a) |
| 40 | 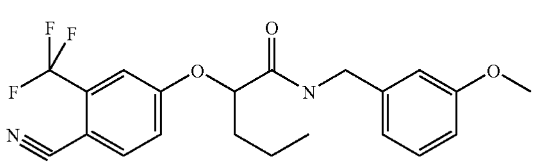 | 241 (a) |

TABLE II-continued
| Example # | Structure | AR Binding IC$_{50}$ (nM) |
|---|---|---|
| 41 | 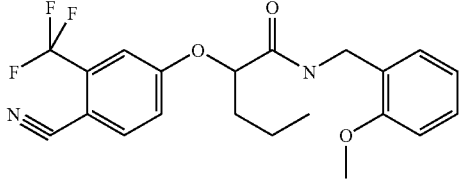 | 171 (a) |
| 42 | 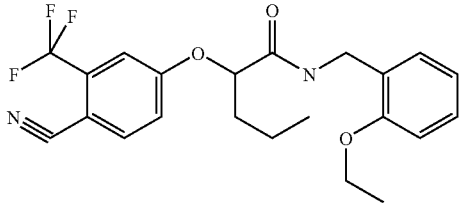 | 139 (a) |
| 43 | 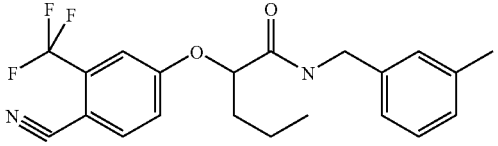 | 99 (N = 9) |
| 44 | 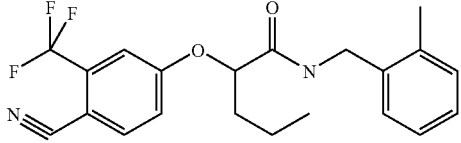 | 42 (a) |
| 45 | 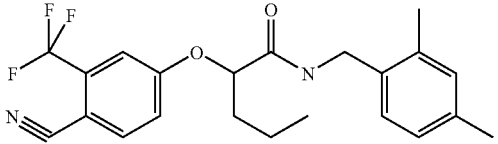 | 58 (a) |
| 46 | 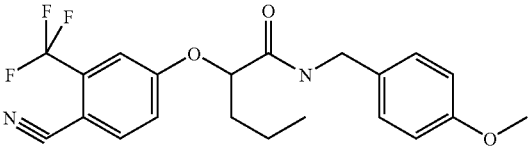 | 103 (a) |
| 47 | 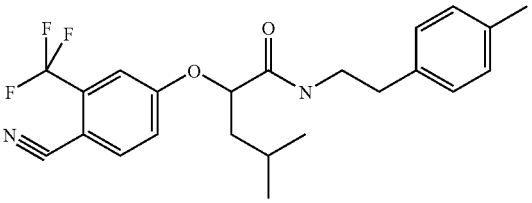 | 144 (a) |
| 48 | 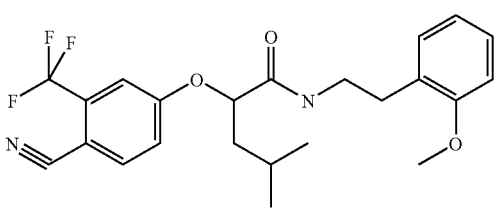 | 123 (a) |

TABLE II-continued

| Example # | Structure | AR Binding IC$_{50}$ (nM) |
|---|---|---|
| 49 | 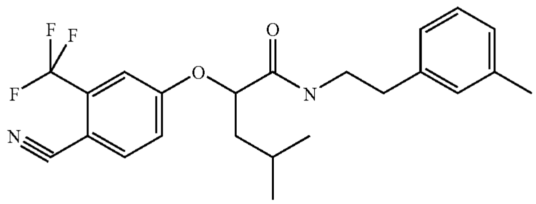 | 75 (a) |
| 50 | 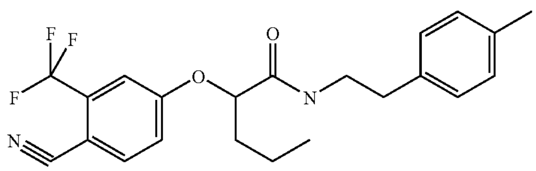 | 399 (a) |
| 51 | 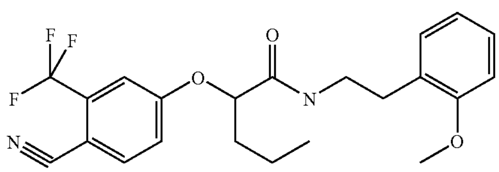 | 381 (a) |
| 52 | 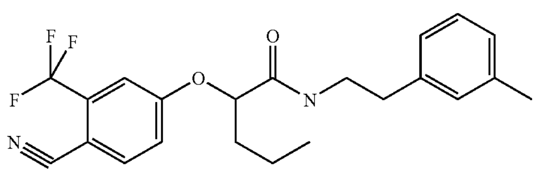 | UA |
| 53 | 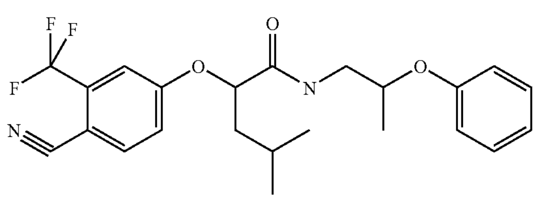 | 59 (a) |
| 54 | 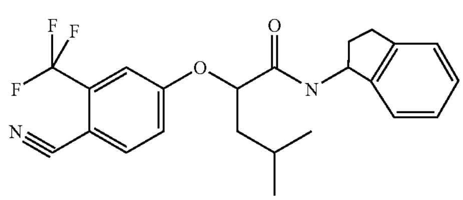 | 70 (a) |
| 55 | 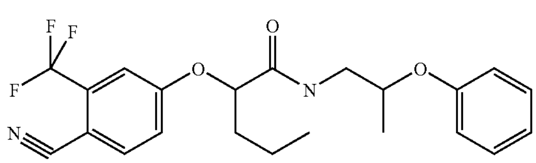 | 182 (a) |
| 56 | 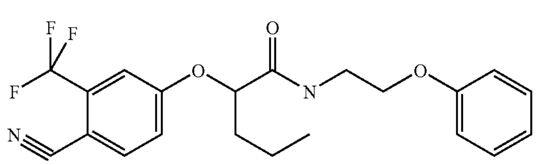 | 157 (a) |

TABLE II-continued

| Example # | Structure | AR Binding IC$_{50\,(nM)}$ |
|---|---|---|
| 57 | 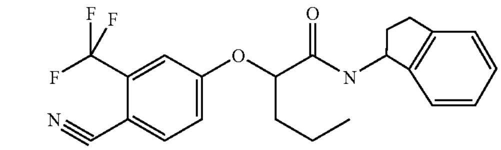 | 146 (a) |
| 58 | 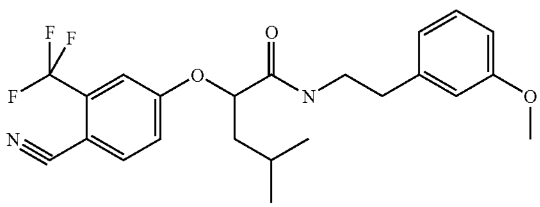 | 64 (a) |
| 59 | 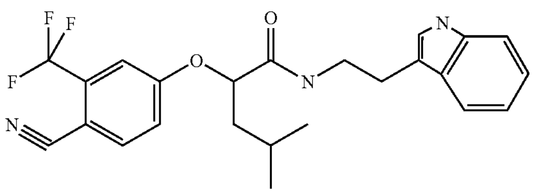 | 48 (c) |
| 60 | 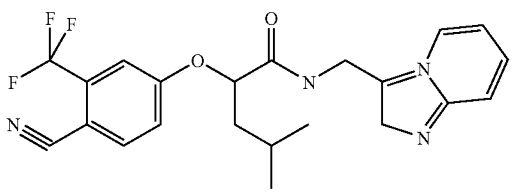 | 318 (a) |
| 61 | 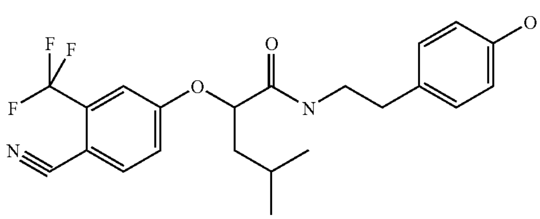 | 86 (N = 8) |
| 62 | 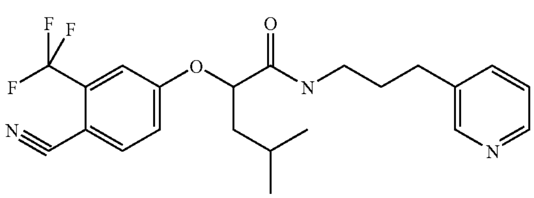 | 192 (a) |
| 63 | 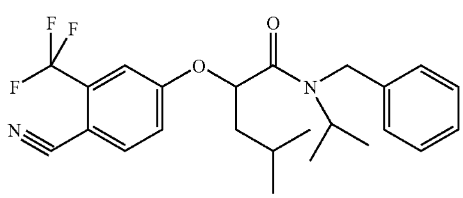 | 482 (a) |
| 64 | 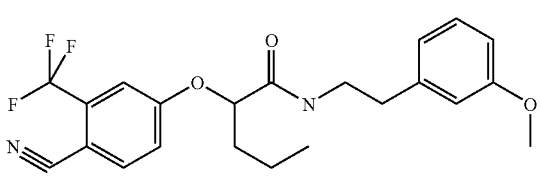 | 220 (a) |

TABLE II-continued

| Example # | Structure | AR Binding IC$_{50\,(nM)}$ |
|---|---|---|
| 65 | 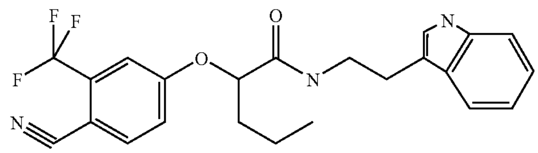 | 33 (b) |
| 66 | 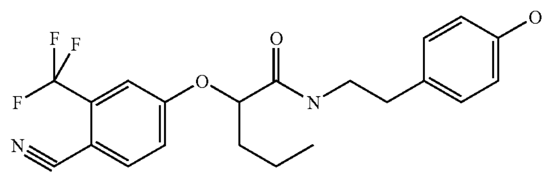 | 151 (N = 6) |
| 67 | 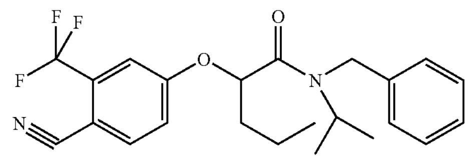 | 440 (a) |
| 68 | 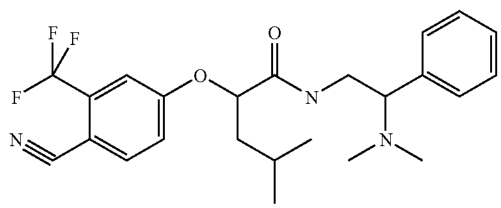 | 223 (a) |
| 69 | 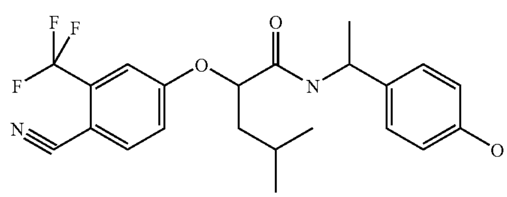 | 341 (a) |
| 70 | 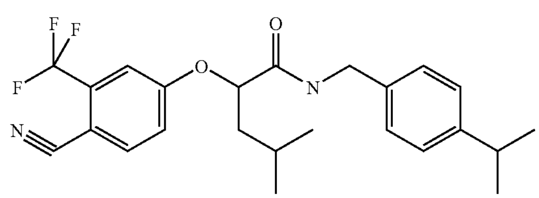 | 253 (a) |
| 71 | 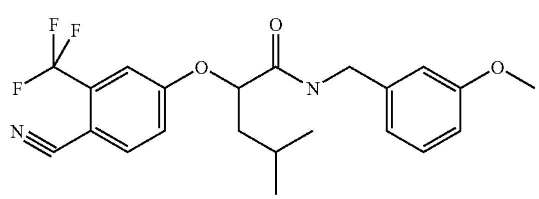 | 288 (a) |
| 72 | 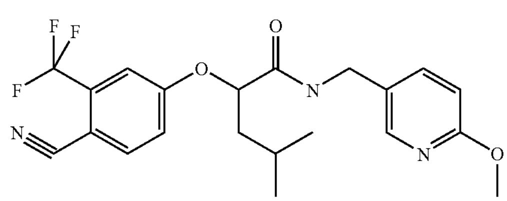 | 82 (a) |

TABLE II-continued

| Example # | Structure | AR Binding IC$_{50}$ (nM) |
|---|---|---|
| 73 | 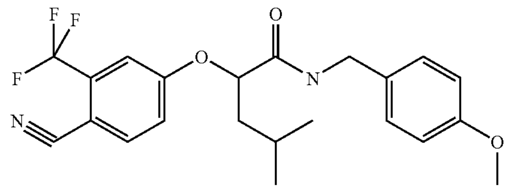 | 92 (a) |
| 74 | 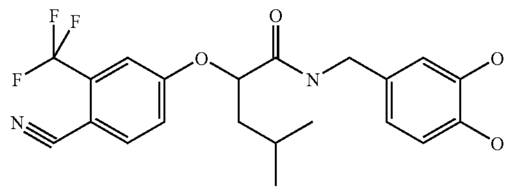 | 139 (a) |
| 75 | 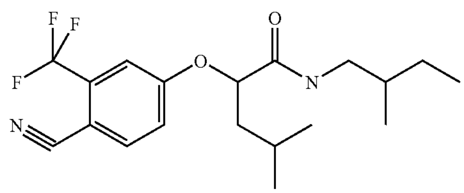 | 417 (a) |
| 76 | 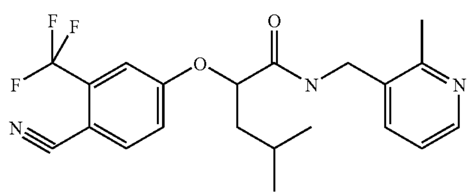 | 479 (a) |
| 77 | 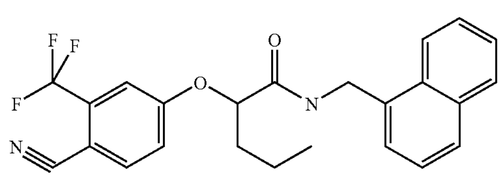 | 292 (a) |
| 78 | 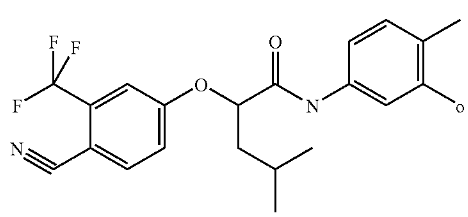 | 121 (c) |
| 79 | 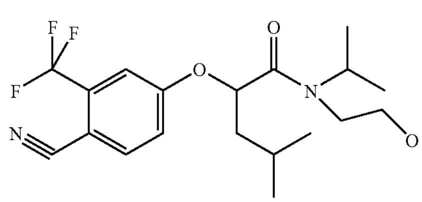 | 3135 (c) |

TABLE II-continued

| Example # | Structure | AR Binding IC$_{50}$ (nM) |
|---|---|---|
| 81 | 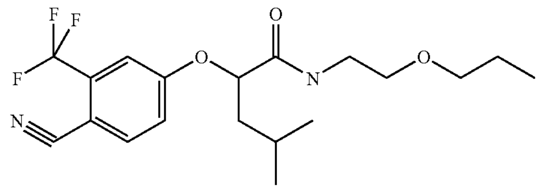 | 142 (a) |
| 82 | 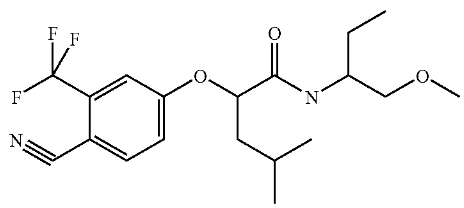 | 218 (a) |
| 83 | 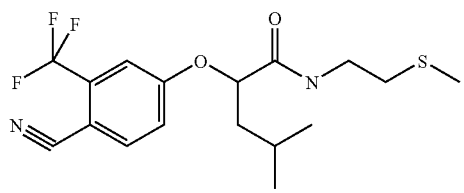 | 85 (a) |
| 84 | 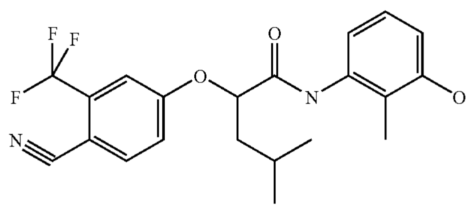 | 112 (a) |
| 85 | 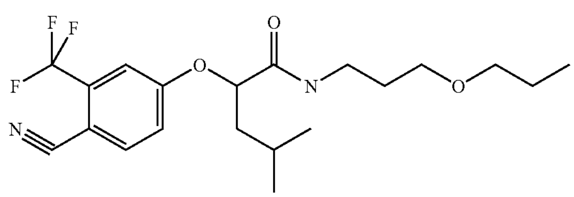 | 117 (a) |
| 86 | 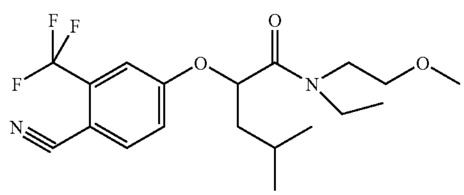 | 25 (a) |
| 87 | 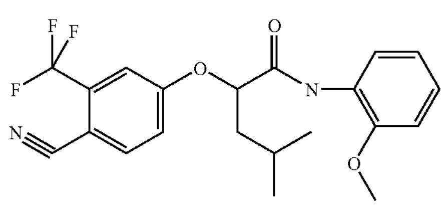 | 119 (a) |

TABLE II-continued

| Example # | Structure | AR Binding IC$_{50\ (nM)}$ |
|---|---|---|
| 88 | 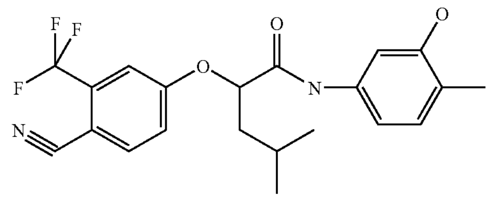 | 296 (c) |
| 89 | 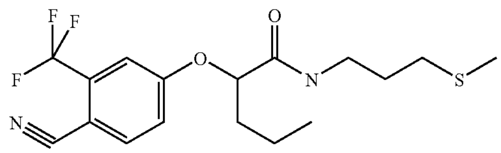 | 486 (a) |
| 90 | 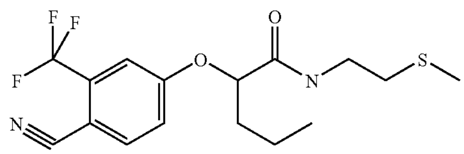 | 736 (a) |
| 91 | 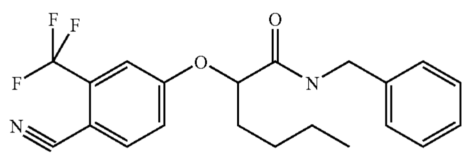 | 70 (c) |
| 92 | 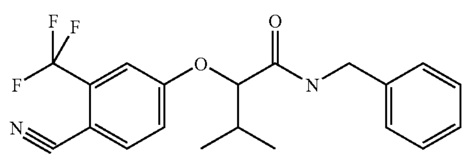 | 348 (c) |
| 93 | 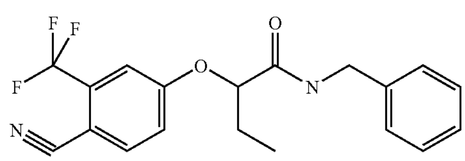 | 485 (c) |
| 94 | 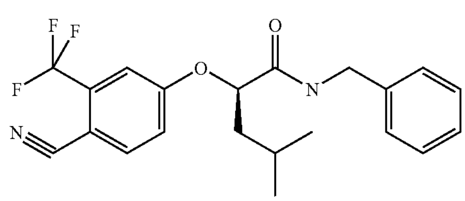 | 66 (b) |
| 95 | 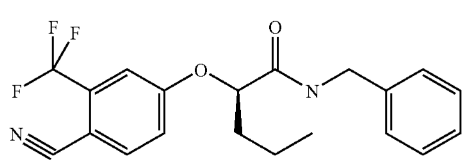 | 126 (b) |

TABLE II-continued

| Example # | Structure | AR Binding IC$_{50\,(nM)}$ |
|---|---|---|
| 96 | 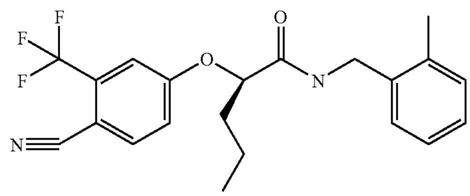 | 95 (a) |
| 97 | 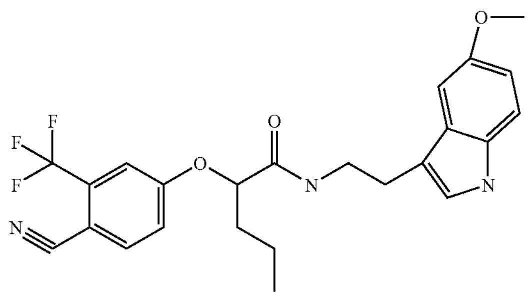 | 111 (a) |
| 98 | 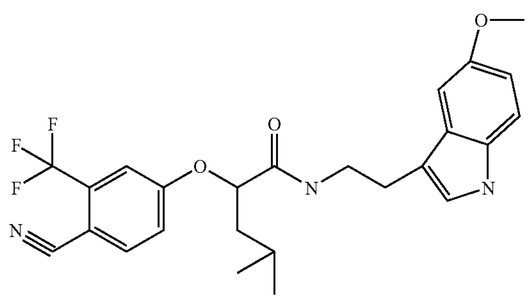 | 279 (a) |
| 99 | 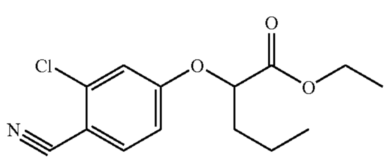 | 31 (a) |
| 100 | 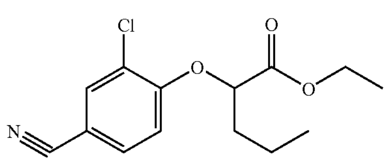 | 347 (a) |
| 101 | 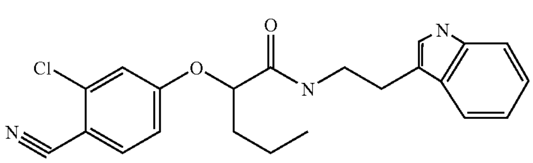 | 53 (a) |
| 102 | 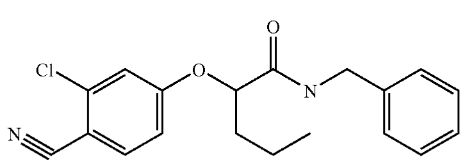 | 125 (c) |

TABLE II-continued

| Example # | Structure | AR Binding IC$_{50\,(nM)}$ |
|---|---|---|
| 103 | 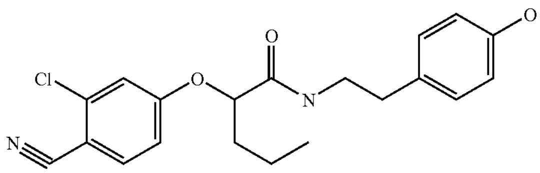 | 140 (b) |
| 104 | 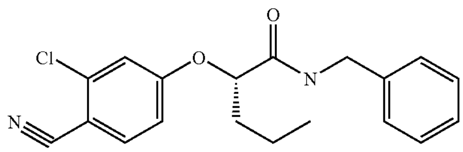 | 241 (c) |
| 105 | 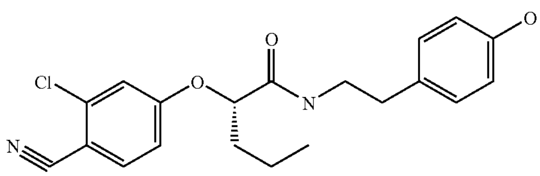 | 241 (c) |
| 106 | 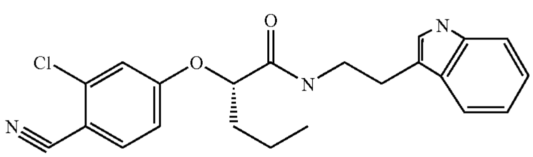 | 47 (a) |
| 107 | 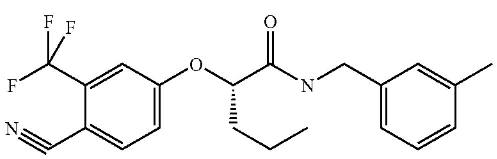 | 93 (a) |
| 108 | 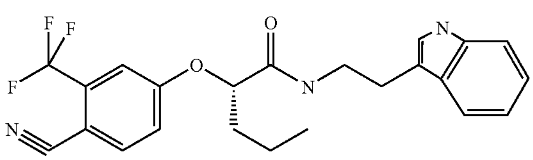 | 21 (a) |
| 109 | 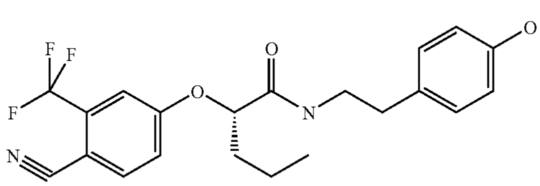 | 251 (a) |
| 110 | 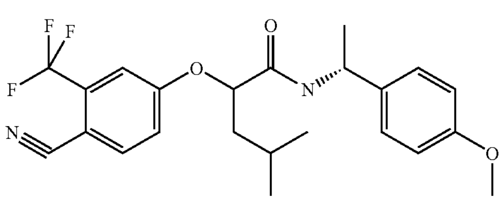 | 340 (c) |

TABLE II-continued

| Example # | Structure | AR Binding IC$_{50\,(nM)}$ |
|---|---|---|
| 111 | 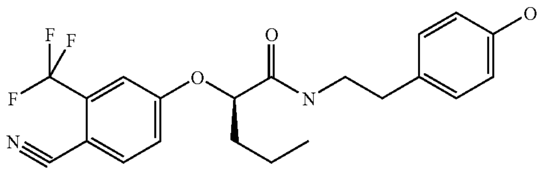 | 148 (b) |
| 112 | 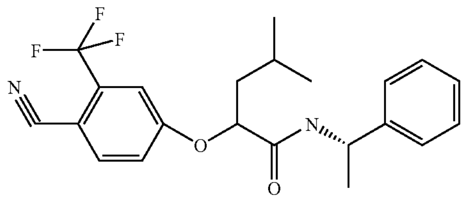 | 329 (a) |
| 113 | 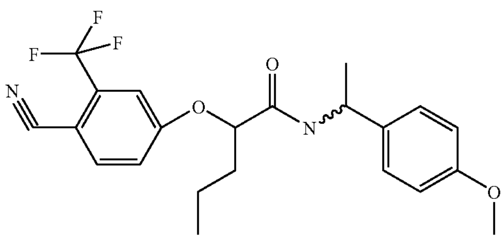 | 654 (c) |
| 114 | 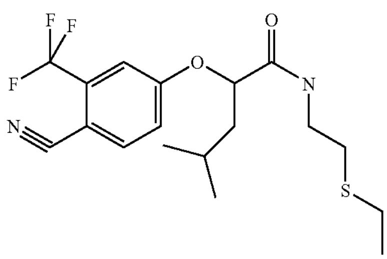 | 102 (a) |
| 115 | 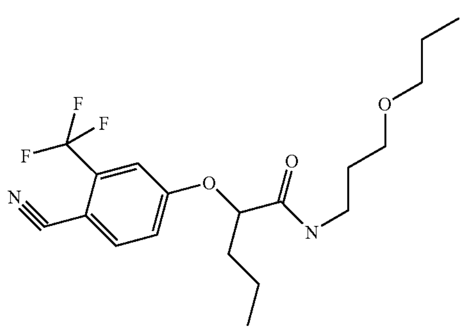 | 428 (a) |
| 116 | 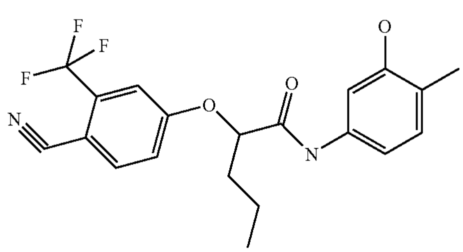 | 296 (c) |

TABLE II-continued

| Example # | Structure | AR Binding IC$_{50}$ (nM) |
|---|---|---|
| 117 | 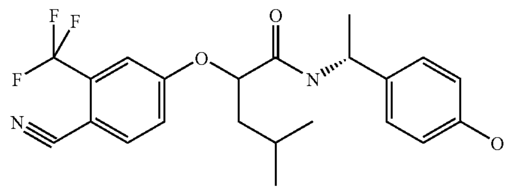 | 114 (a) |
| 118 | 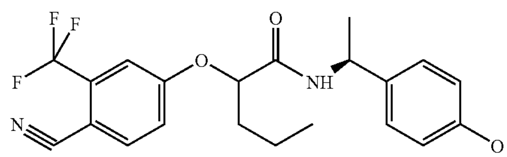 | 1005 (c) |
| 119 | 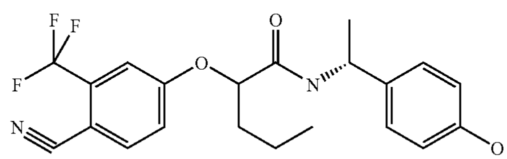 | 86 (c) |
| 120 | 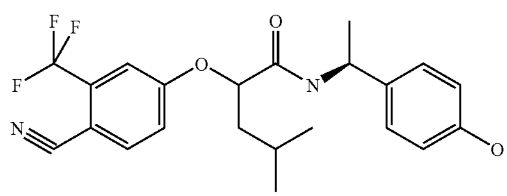 | 98 (a) |
| 121 | 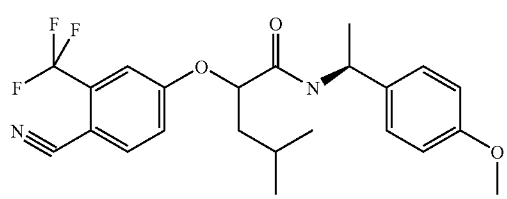 | 145 (a) |
| 122 | 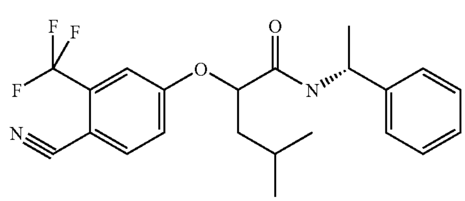 | 329 (a) |
| 123 | | 653 (c) | a—mean of 2 tests
b—mean of 3 tests
c—mean of 4 tests
UA—data unavailable
ND—not determined

Example 124

The compounds ability to antagonize the effects of androgen on the androgen receptor were determined in a whole cell assay as described immediately below.

Experimental Procedure for AR Antagonist Cell Assay

Cell line: MDA-MB453-MMTV clone 54-19. This cell line is a stable transfected cell line with MDA-MB453 cell background (a human breast tumor cell line expressing androgen receptor). A MMTV minimal promoter containing ARE was first cloned in front of a firefly luciferase reporter gene. Then the cascade was cloned into transfection vector pUV120puro. Electroporation method was used for transfecting MDA-MB-453 cell. Puromycin resistant stable cell line was selected.

Cell Culture Media and Reagents:

Culture medium: DMEM (high glucose, Gibco cat #: 11960-044), 10% FBS, and 1% L-glutamine Plating medium: DMEM (phenol red free), 10% charcoal treated HyClone serum, 1% L-glutamine Assay medium: DMEM (phenol red free), 1% charcoal treated HyClone serum, 1% L-glutamine, and 1% penicillin/streptomycin 3× luciferase buffer: 2% beta-mercaptoethanol, 0.6% ATP, 0.0135% luciferine in cell lysis buffer Assay Procedure:
1. Cells are maintained in culture medium, splitting cells when they reach 80-90% confluence
2. To test compounds, 10,000 cells/well are plated to opaque 96 cell culture plate in 100 ul/well plating medium, culture for overnight at 37° C. in cell culture incubator
3. Carefully remove plating medium, then add 80 ul/well of pre-warmed assay medium, add 10 ul/well testing compound (final concentration at) 1000 nM, 200 nM, 40 nM, 8 nM, 1.6 nM, and 0.32 nM), incubate at 37° C. for 30 minutes
4. Add 10 ul/well freshly prepared DHT (final concentration at 100 pM) to each well, incubate at 37° C. for 17 hr (overnight)
5. Add 50 ul/well 3× luciferase buffer, incubate at room temperature for 5 minutes, then count on Luminometer The fold induction over background by 100 pM DHT in the absence of testing compounds is standardized as 100% and experimental result is expressed as percentage of inhibition by testing compounds.

The results are described below in Table III. The results are reported as the mean of multiple tests as described below (the numbers of tests are indicated in the footnote). N.D. denotes that the compound was not tested.

TABLE III

| Example # | Structure | AR Cell IC$_{50}$ (nM) |
|---|---|---|
| 1 | 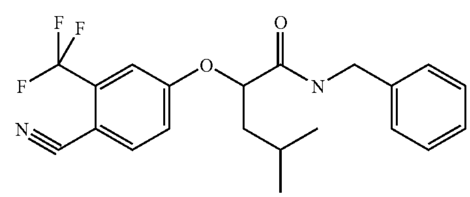 | 201 (c) |
| 2 | 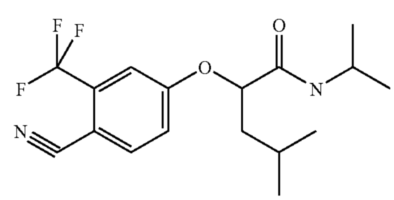 | 142 (c) |
| 3 | 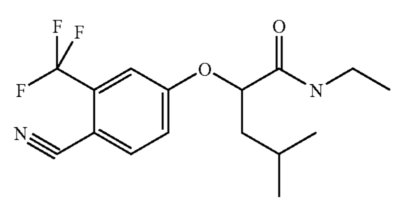 | ND |
| 4 | 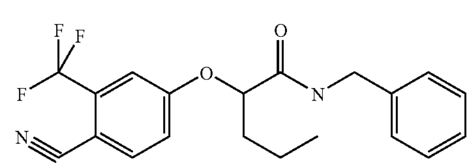 | 57 (N = 6) |

TABLE III-continued
| Example # | Structure | AR Cell IC$_{50}$ (nM) |
|---|---|---|
| 5 | 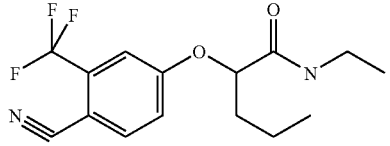 | >1000 (a) |
| 6 | 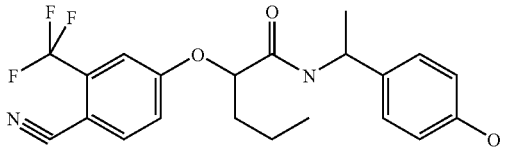 | ND |
| 7 | 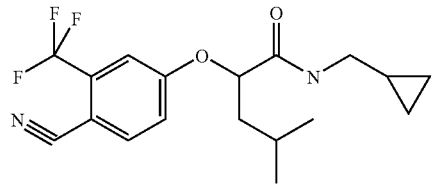 | 661 (a) |
| 8 | 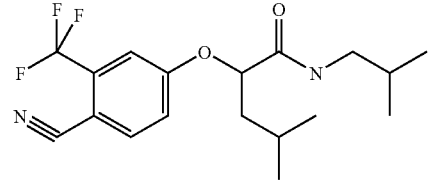 | 534 (a) |
| 9 | 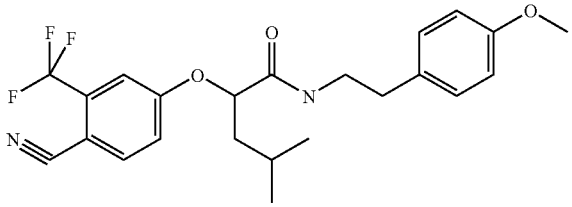 | >1000 (a) |
| 10 | 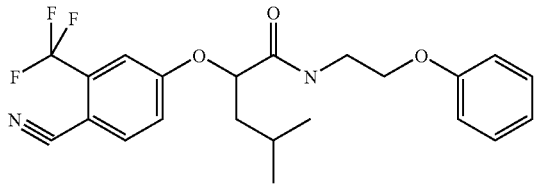 | >1000 (a) |
| 11 | 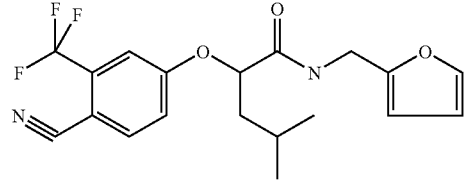 | >1000 (a) |
| 12 | 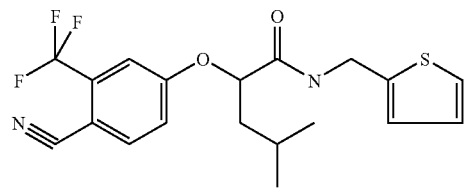 | >1000 (a) |

TABLE III-continued

| Example # | Structure | AR Cell IC$_{50}$ (nM) |
|---|---|---|
| 13 | 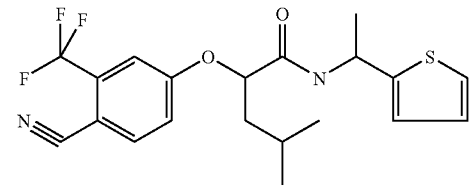 | 398 (a) |
| 14 | 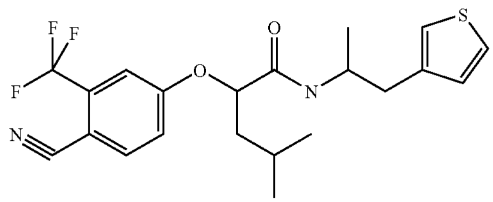 | >1000 (a) |
| 15 | 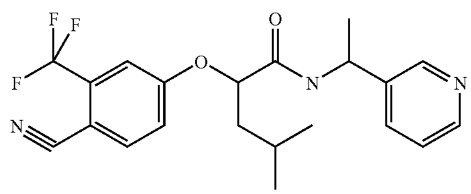 | >1000 (a) |
| 16 | 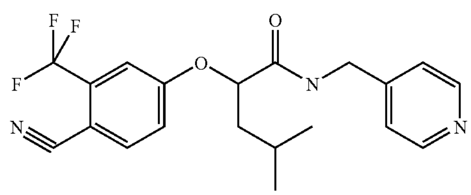 | ND |
| 17 | 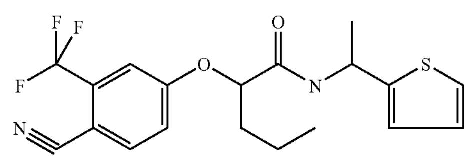 | ND |
| 18 | 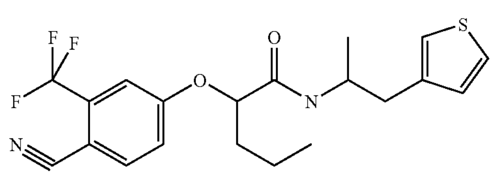 | 815 (a) |
| 19 | 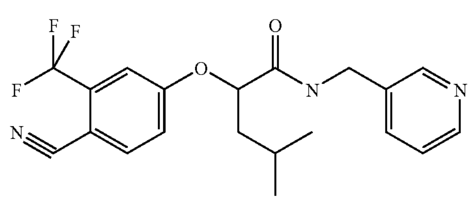 | >1000 (a) |
| 20 | 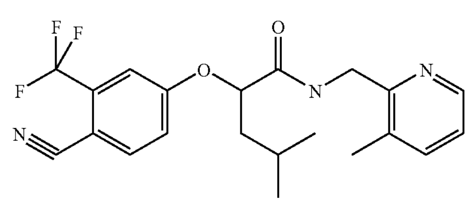 | ND |

TABLE III-continued

| Example # | Structure | AR Cell IC$_{50}$ (nM) |
|---|---|---|
| 21 | 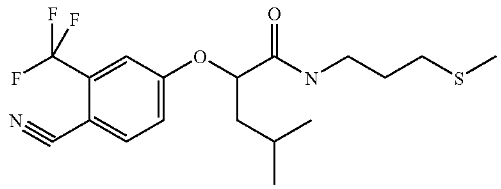 | ND |
| 22 | 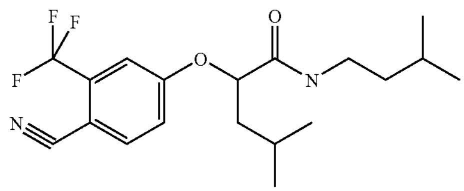 | >1000 (a) |
| 23 | 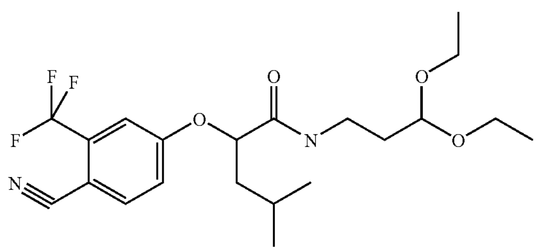 | UA |
| 24 | 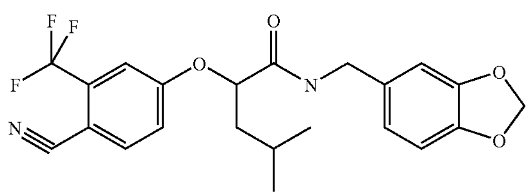 | 799 (a) |
| 25 | 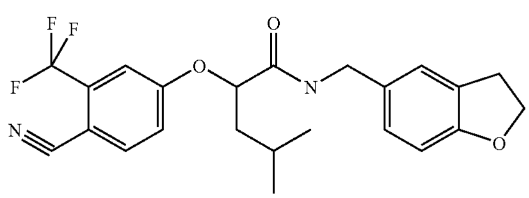 | (798) (a) |
| 26 | 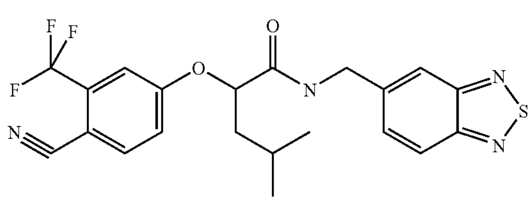 | >1000 (a) |
| 27 | 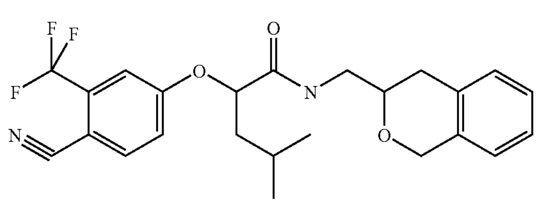 | ND |

TABLE III-continued

| Example # | Structure | AR Cell IC$_{50}$ (nM) |
|---|---|---|
| 29 | 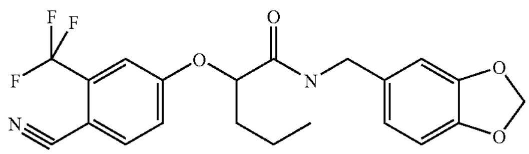 | >1000 (a) |
| 30 | 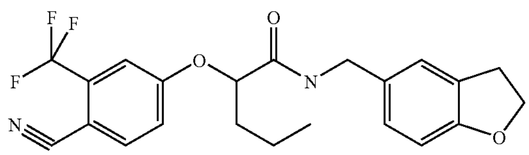 | 355 c) |
| 31 | 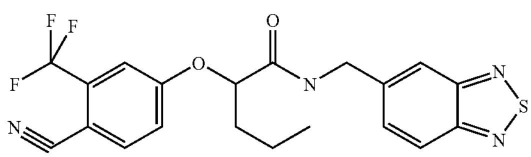 | >1000 (a) |
| 32 | 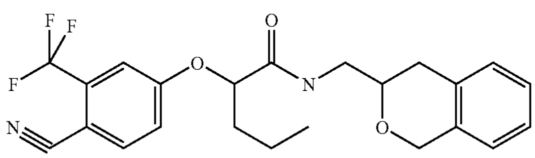 | ND |
| 33 | 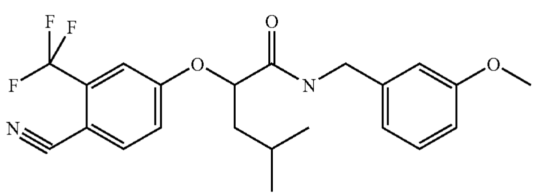 | 864 (a) |
| 34 | 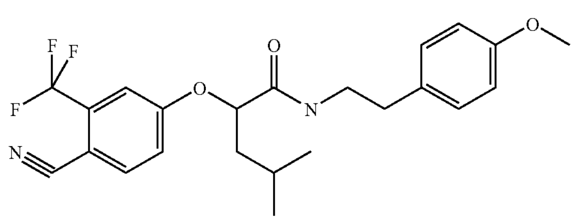 | >1000 (a) |
| 35 | 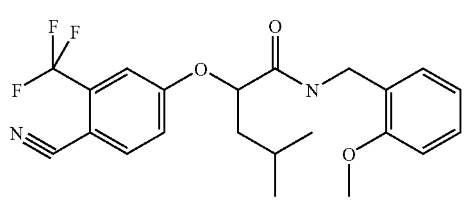 | 768 (a) |
| 36 | 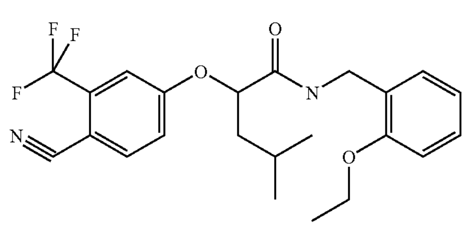 | >1000 (a) |

TABLE III-continued

| Example # | Structure | AR Cell IC$_{50}$ (nM) |
|---|---|---|
| 37 | 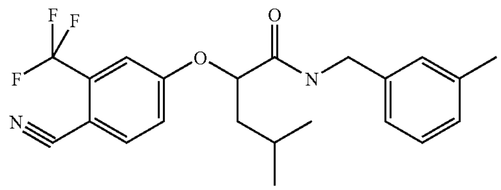 | >1000 (a) |
| 38 | 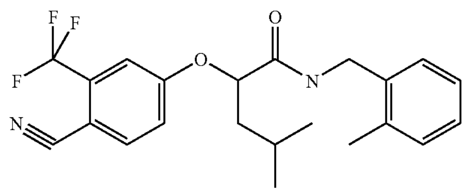 | >1000 (a) |
| 39 | 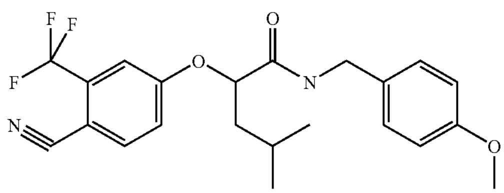 | >1000 (a) |
| 40 | 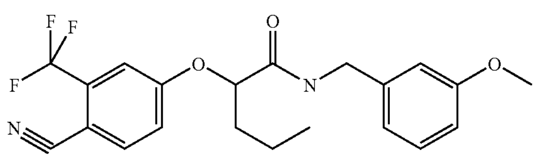 | ND |
| 41 | 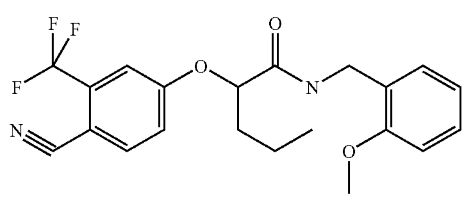 | 130 (N = 6) |
| 42 | 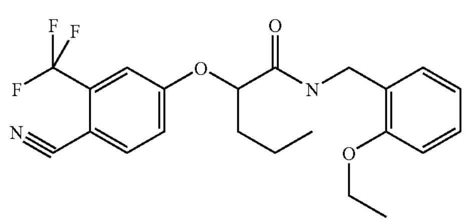 | >1000 (a) |
| 43 | 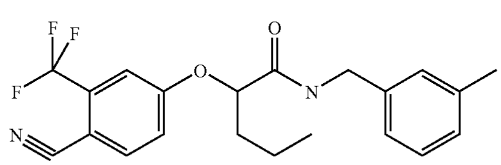 | 105 (c) |
| 44 | 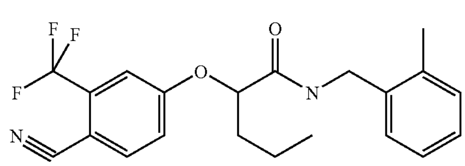 | 37 (c) |

TABLE III-continued

| Example # | Structure | AR Cell IC$_{50}$ (nM) |
|---|---|---|
| 45 | 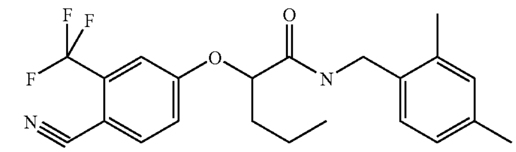 | >1000 (a) |
| 46 | 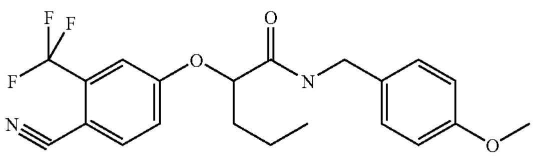 | 638 (a) |
| 47 | 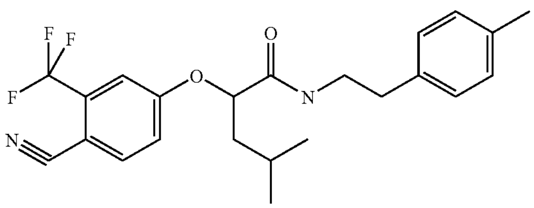 | >1000 (a) |
| 48 | 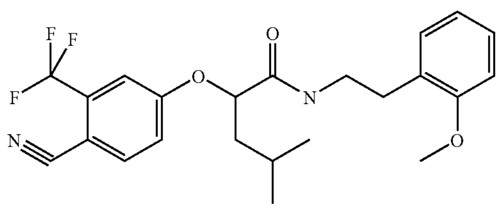 | >1000 (a) |
| 49 | 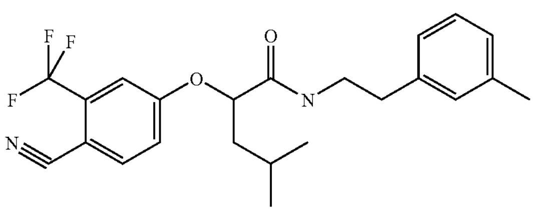 | >1000 (a) |
| 50 | 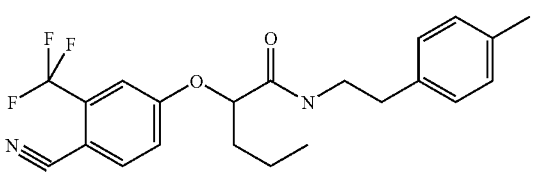 | ND |
| 51 | 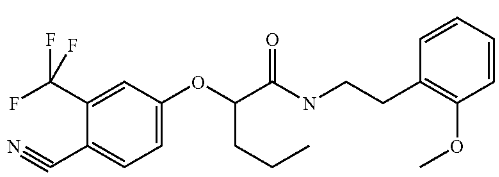 | ND |
| 52 | 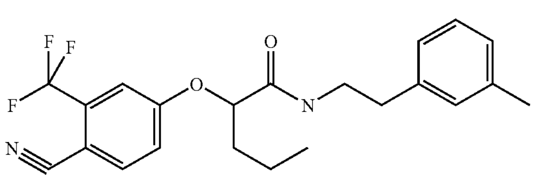 | UA |

TABLE III-continued

| Example # | Structure | AR Cell IC$_{50}$ (nM) |
|---|---|---|
| 53 | 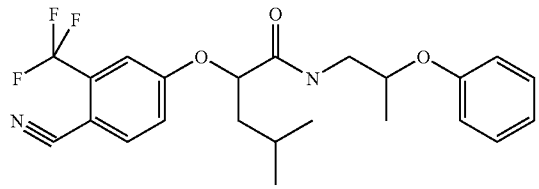 | 299 (a) |
| 54 | 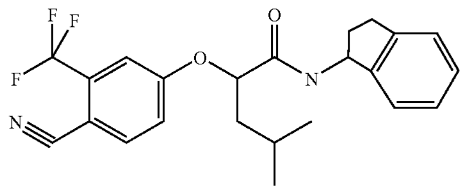 | 836 (a) |
| 55 | 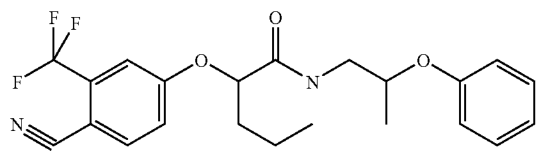 | 393 (a) |
| 56 | 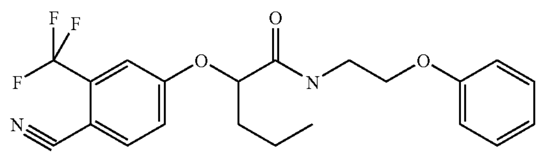 | 790 (a) |
| 57 | 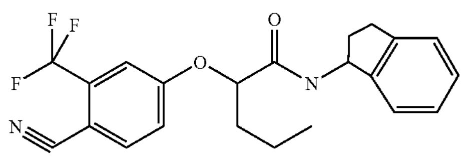 | 561 (a) |
| 58 | 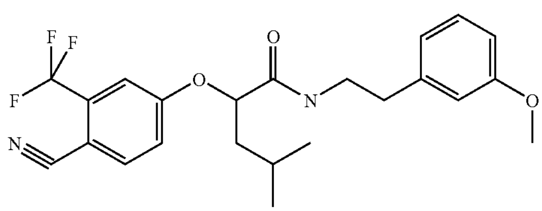 | >1000 (a) |
| 59 | 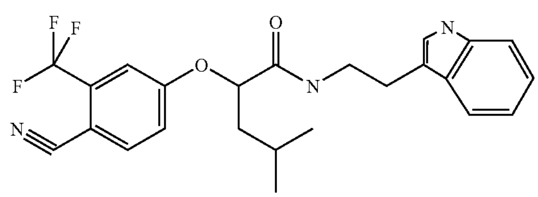 | 101 (a) |
| 60 | 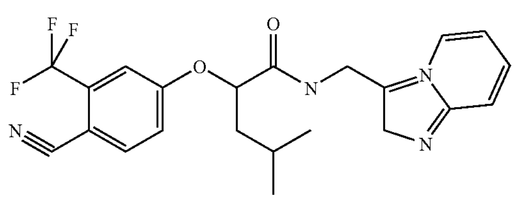 | ND |

TABLE III-continued

| Example # | Structure | AR Cell IC$_{50}$ (nM) |
|---|---|---|
| 61 | 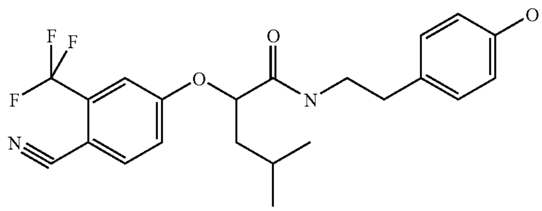 | 341 (N = 10) |
| 62 | 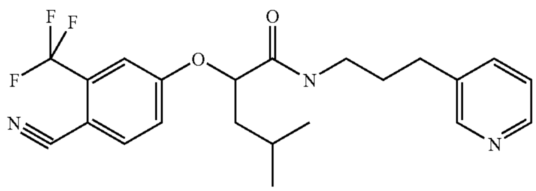 | >1000 (a) |
| 63 | 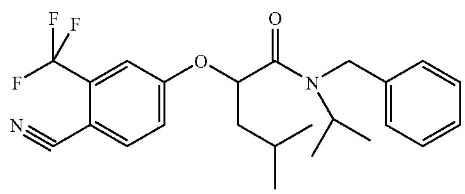 | ND |
| 64 | 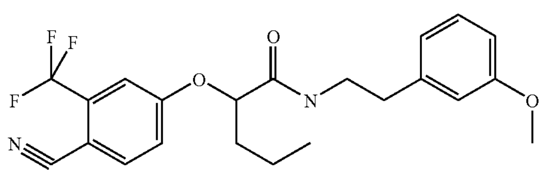 | >1000 (a) |
| 65 | 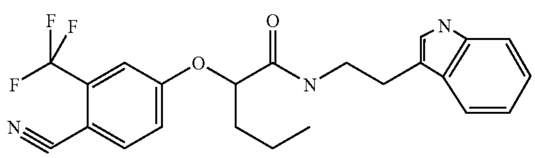 | 64 (N = 6) |
| 66 | 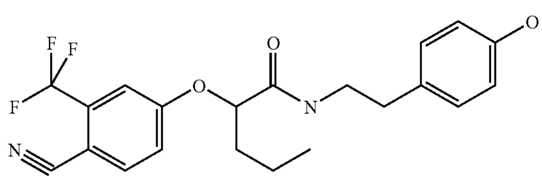 | 77 (N = 10) |
| 67 | 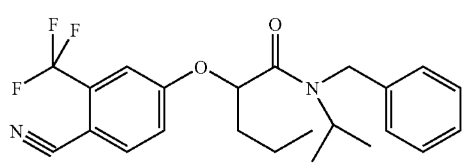 | ND |
| 68 | 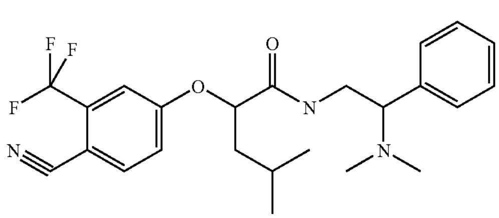 | >1000 (a) |

TABLE III-continued

| Example # | Structure | AR Cell IC$_{50}$ (nM) |
|---|---|---|
| 69 | 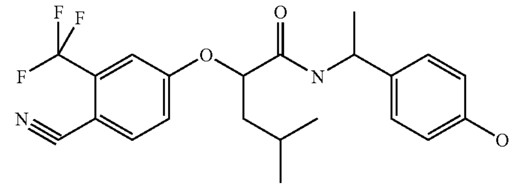 | ND |
| 70 | 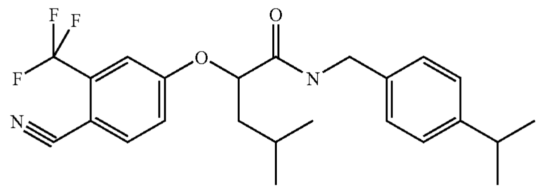 | ND |
| 71 | 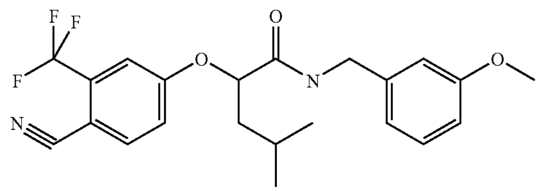 | ND |
| 72 | 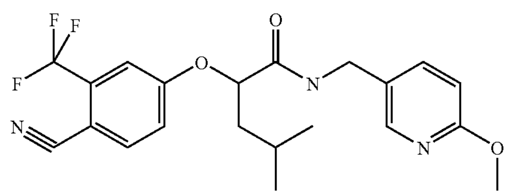 | 251 (c) |
| 73 | 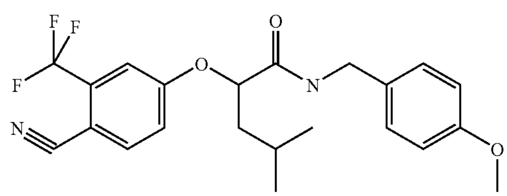 | 428 (a) |
| 74 | 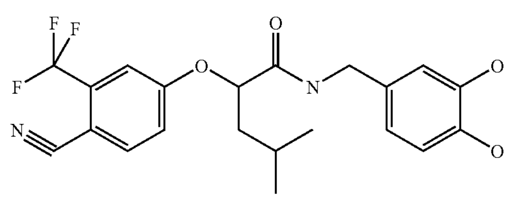 | 976 (c) |
| 75 | 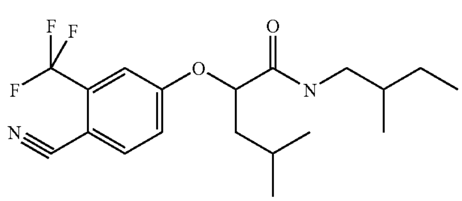 | ND |

TABLE III-continued

| Example # | Structure | AR Cell IC$_{50}$ (nM) |
|---|---|---|
| 76 | 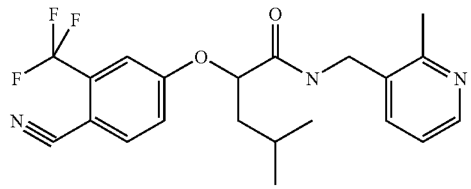 | ND |
| 77 | 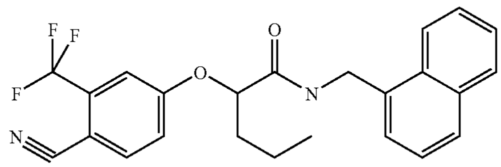 | ND |
| 78 | 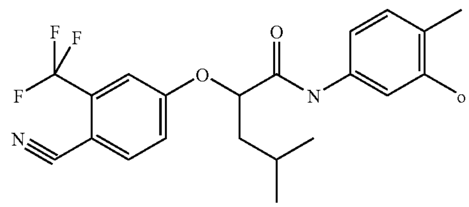 | 948 (a) |
| 79 | 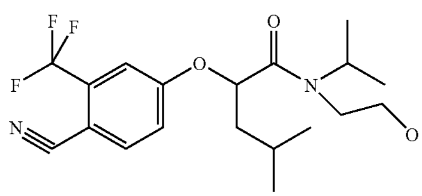 | >1000 (a) |
| 81 | 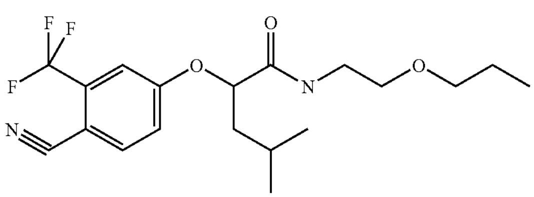 | >1000 (a) |
| 82 | 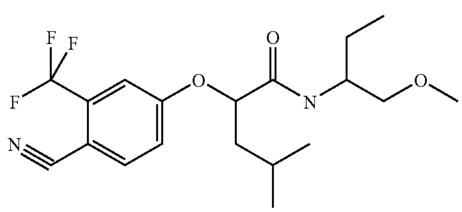 | >1000 (a) |
| 83 | 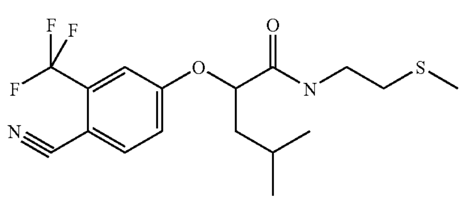 | >1000 (a) |

TABLE III-continued

| Example # | Structure | AR Cell IC$_{50}$ (nM) |
|---|---|---|
| 84 | 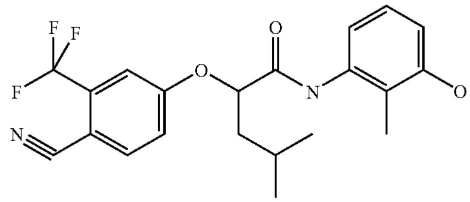 | >1000 (a) |
| 85 | 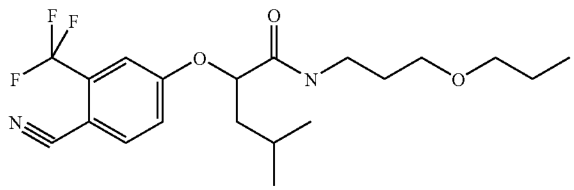 | >1000 (a) |
| 86 | 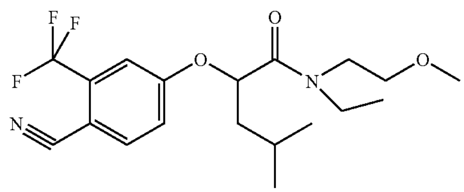 | >1000 (a) |
| 87 | 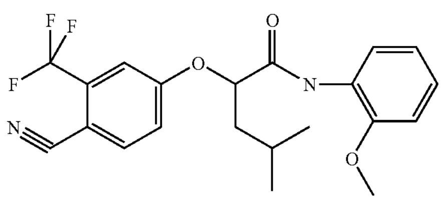 | >1000 (a) |
| 88 | 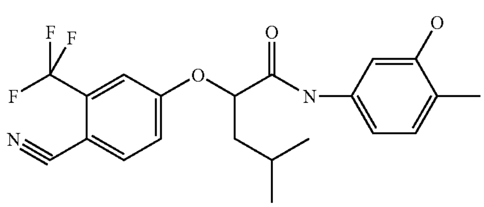 | ND |
| 89 | 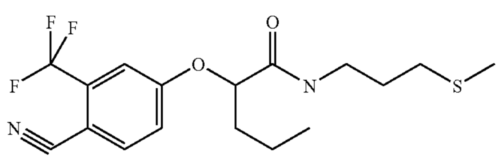 | ND |
| 90 | 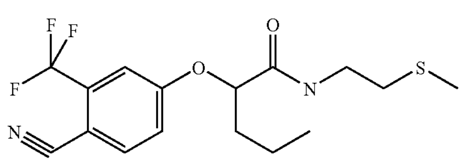 | ND |
| 91 | 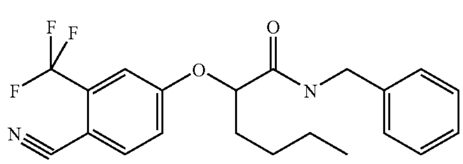 | 535 (c) |

TABLE III-continued

| Example # | Structure | AR Cell IC$_{50}$ (nM) |
|---|---|---|
| 92 | 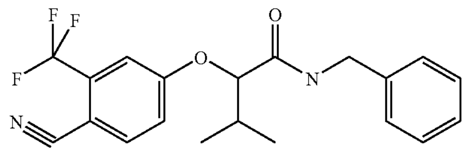 | 562 (a) |
| 93 | 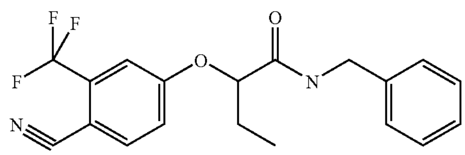 | 563 (a) |
| 94 | 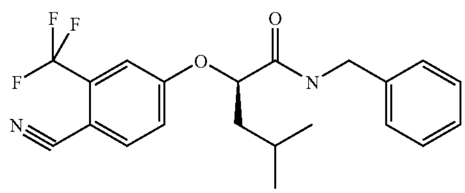 | 140 (c) |
| 95 | 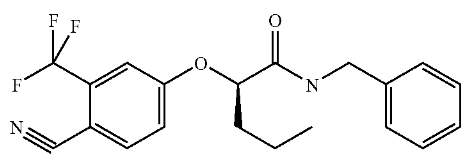 | 32 (c) |
| 96 | 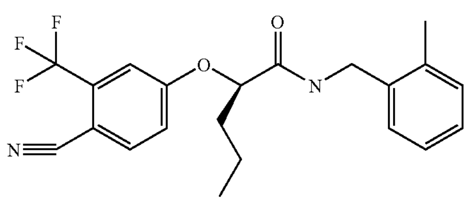 | 138 (a) |
| 97 | 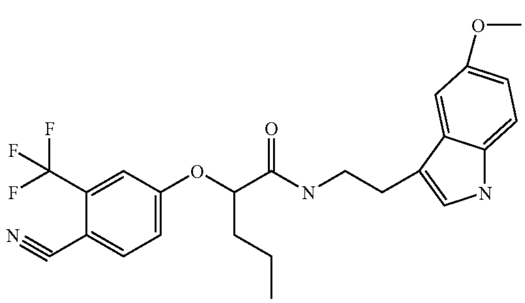 | 26 (a) |
| 98 | 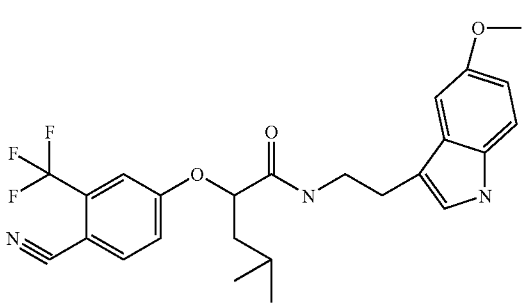 | N.D. |

TABLE III-continued

| Example # | Structure | AR Cell IC$_{50}$ (nM) |
|---|---|---|
| 99 | 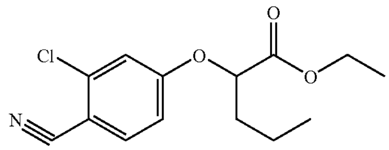 | 749 (a) |
| 100 | 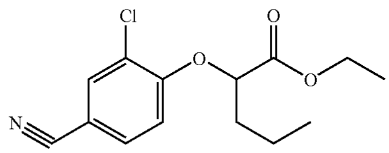 | ND |
| 101 | 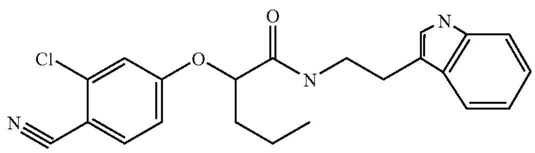 | 38 (a) |
| 102 | 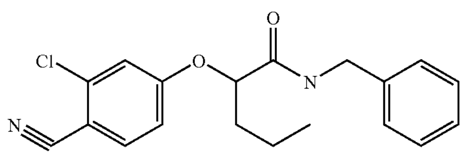 | 27 (c) |
| 103 | 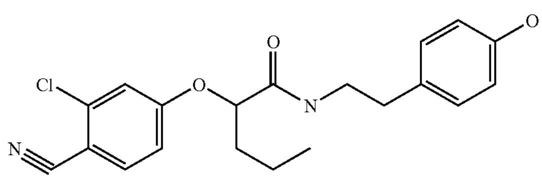 | 87 (c) |
| 104 | 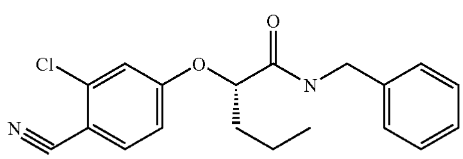 | 7 (c) |
| 105 | 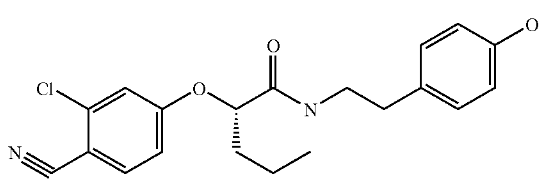 | 88 (c) |
| 106 | 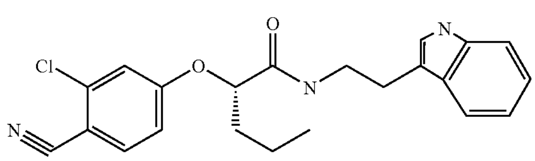 | 3 (a) |
| 107 | 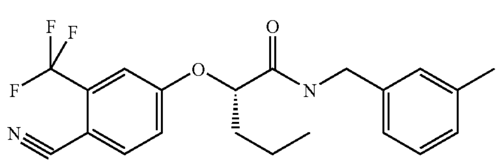 | <0.32 (a) |

TABLE III-continued

| Example # | Structure | AR Cell IC$_{50}$ (nM) |
|---|---|---|
| 108 | 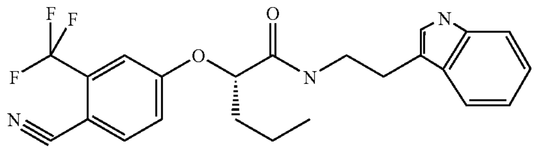 | <0.32 (a) |
| 109 | 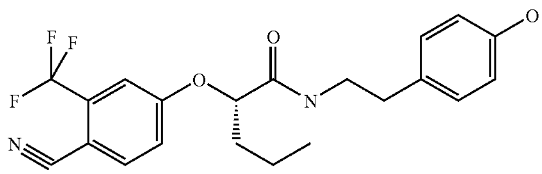 | 58 (a) |
| 110 | 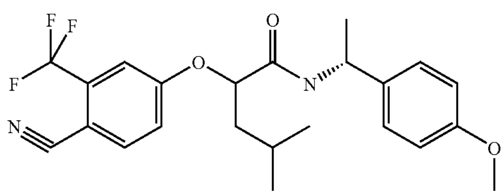 | ND |
| 111 | 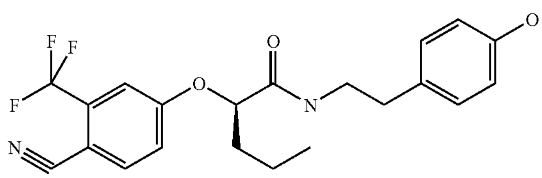 | 164 (c) |
| 112 | 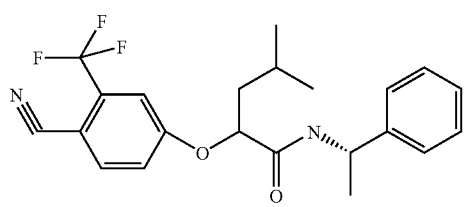 | ND |
| 113 | 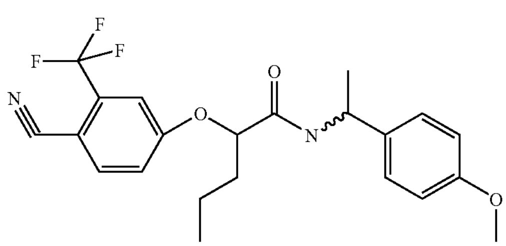 | 681 (a) |
| 114 | 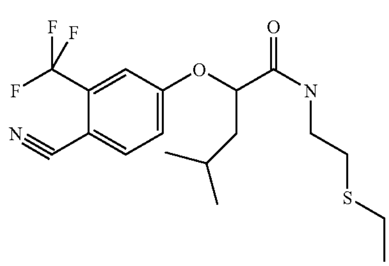 | 727 (a) |

TABLE III-continued

| Example # | Structure | AR Cell IC$_{50}$ (nM) |
|---|---|---|
| 115 | 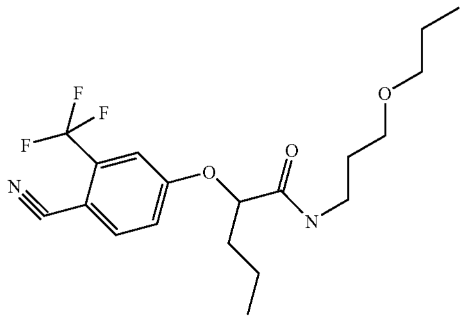 | ND |
| 116 | | ND |
| 116 | | ND |
| 117 | 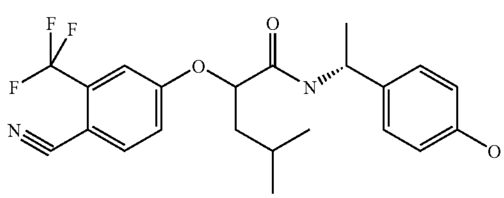 | 19 (a) |
| 118 | 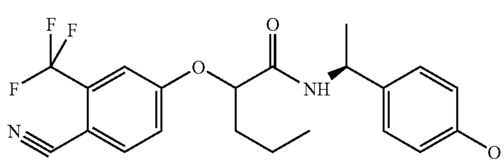 | 589 (a) |
| 119 | 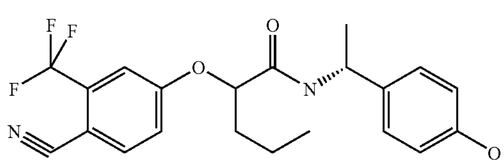 | 117 (a) |
| 120 | 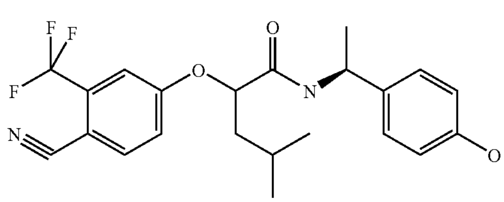 | 44 (c) |

TABLE III-continued

| Example # | Structure | AR Cell IC$_{50}$ (nM) |
|---|---|---|
| 121 | [structure] | 157 (c) |
| 122 | [structure] | ND |
| 123 | [structure] | 681 (a) | a—mean of two tests
b—mean of three tests
c—mean of four tests
UA—unavailable
ND—not determined Example 126

Animal Model for Androgenetic Alopeica

As described above, alopecia is a problem that medical science has devoted considerable resources to. As with any disease process, animal models have been developed to allow scientists to screen compounds for their potential relative efficacy. Those compounds showing the greatest efficacy in these animal models are considered for further study in humans. Two different animal models have been developed to date for alopecia. The first is the telogen conversion assay, which uses female C3H/HeN mice. The second model uses stump-tailed macaques, which are monkeys that suffer from androgenetic alopecia.

The telogen conversion assay measures the potential of a compound to convert the resting stage of the hair growth cycle ("telogen") to the active stage of the hair growth cycle ("anagen") in mice. This assay takes advantage of the fact that the fur (i.e. hair) of 7-week-old C3H/HeN mice is in the telogen phase. This phase continues until about 75 days of age. In this assay, selected areas of the mice are shaved, contacted with a test agent, or a control, and the difference in the rate of hair growth is measured (i.e. induction of the anagen phase). The first sign of anagen is the darkening of skin color as melanocytes in the follicles start to synthesize melanin, in preparation for the production of pigmented hairs. This model has a number of advantages. This includes the ready availability of female CH3HeN mice, the ability to screen large numbers of compounds quickly, and the ease of housing and handling such animals.

The primary disadvantage of this model is its lack of androgenetic dependency. While the exact cause of human baldness is not known, it is well documented that androgens induce a regression of hair follicles in the scalp. This post adolescent regressive change is a fundamental cause of male pattern baldness, (i.e. "androgenetic alopecia). This phenomenon occurs in both men and women who have inherited the genetic trait for alopecia, as mentioned previously. For a more detail discussion of the effects of androgens on human scalps, the readers attention is directed to Trueb, R M, Molecular Mechanisms of Androgenic Alopecia, *Exp. Gerontology*, 2002, 27:981-990.

Researchers looked for other animals whose hair growth was similar to that of humans. These lead researchers to stump-tailed macaques. These primates also suffer from androgenetic alopecia. Essentially all post adolescent macaques, in both sexes, exhibit the development of baldness. Like the development of male pattern baldness in humans, androgens are an indispensable triggering factor in macaque baldness. Thinning of the frontal scalp hairs begins to appear around the same age (4 years) when serum levels of testosterone become drastically elevated in male animals. Although the elevation of testosterone in females is approximately one tenth that of the male level, there is no difference in the incidence and the age of onset of baldness between male and female stump-tailed macaques. Topical application of anti-androgens have reversed this baldness in animals of both sexes (Pan, H J et al, Evaluation of RU58841 as an anti-androgen in prostate PC3 cells and a topical anti-alopecia agent in the bald scalp of stump tailed macaques. *Endocrine* 1998; 9:39-43).

While this model is a significant improvement over the telogen conversion assay as a model for human baldness, it suffers from a number of practical disadvantages. The macaques are expensive, relatively rare, labor intensive to maintain, and require long wash out periods between testing. Thus, the macaque is not a practical model for screening large numbers of compounds It has been discovered that male C3H/HeN mice may be used in the telogen conversion assay, when evaluating anti-androgen test compounds. Thus, the model relates to a modification of the existing telogen conversion assay. Male C3H/HeN mice approximately 7 weeks old are utilized. These animals are also uniformly in telogen, like their female counterparts. However, once shaven, the androgens inherently present in these male mice inhibit the conversion of the hair follicles to the anagen phase. An anti-androgen will block this androgenic effect and the follicles will convert to anagen, like their female counterparts.

Example 126A

The compound described in Example 1 was submitted for further testing utilizing the modified telogen conversion assay, described above. The testing was carried out in the following manner.

Male C3H/HeN mice, 6 to 7 weeks old (Charles River Laboratories, Raleigh, N.C.) were used for the study. Fur was clipped from the dorsal region of the mice prior to initiation of the study. Only mice with pink skin, a visual indication of the telogen phase, were selected for inclusion in the study.

The test compound was dissolved in a vehicle consisting of propylene glycol (30%) and ethanol (70%) to achieve concentrations of 1% and 4% w/v. The relevant dose was applied topically to the clipped dorsal region of the mice in one test group (7-10 mice) in a volume of 20 µl/cm$^2$. A third group of animals received only the vehicle to serve as a control. Treatments were applied twice daily for 4 weeks.

The treatment area was observed and graded every other day for signs of hair growth. The hair growth response was quantified by recording, for each animal, the day on which signs of hair growth first appeared over the treated area. The first sign of anagen was the darkening of skin color as melanocytes in the follicles started to synthesize melanin in preparation for the production of pigmented hairs. The mice were observed for 35 days or longer.

Example 126B

The protocol described above in Example 98A was repeated for the product of Example 4 at a concentration of 3 w/v %. Anagen did not occur in the test group prior to its initiation in the vehicle control group.

Example 127

Animal Model for Inhibition of Sebum Production

Luderschmidt et al describes an animal model for testing whether compounds are capable of modulating sebum secretion. Arch. Derm. Res. 258, 185-191 (1977). This model uses male Syrian hamsters, whose ears contain sebaceous glands. The products of Example 1 and 4 were screened in this model.

Testing for sebum inhibition was carried out in the following manner. Male Syrian hamsters aged 9 to 10 weeks were introduced into the laboratory environment and acclimated for 2 weeks prior to use in the study. Each group consisted of 5 animals and run in parallel with vehicle and positive controls. Prior to administration, 30 mg of each compound was dissolved in 1 mL of a solvent consisting of transcutanol, ethanol, and propylene glycol (20/60/20% v/v) to achieve a final concentration of 3-w/v %.

Animals were dosed topically twice daily, five days a week, for 4 weeks. Each dose consisted of 25 micro liters of vehicle control or drug. The dose was applied to the ventral surfaces of both the right and left ears. All animals were sacrificed approximately 18-24 hours after the final dose. The right ears were collected from each animal and used for sebum analysis.

The ears were prepped for HPLC analysis in the following manner. One 8 mm distal biopsy punch was taken, just above the anatomical "V" mark in the ear to normalize the sample area. The punch was pulled apart. The ventral biopsy surface (the area where the topical dose was directly applied to the sebaceous glands) was retained for testing and the dorsal surface of the biopsy punch was discarded.

Tissue samples were blown with $N_2$ gas and stored at −80° C. under nitrogen until HPLC analysis. In addition to ear samples, an aliquot of each drug and vehicle (at least 250 ul) was also stored at −80° C. for inclusion in the HPLC analysis.

HPLC analysis was carried out on an extract of the tissue sample. Tissue samples were contacted with 3 ml of solvent (a 4:1 admixture of 2,2,4-trimethylpentane and isopropyl alcohol). The mixture was shaken for 15 minutes and stored overnight at room temperature, protected from light. The next morning 1 milliliter of water was added to the sample and shaken for 15 minutes. The sample was then centrifuged at approximately 1500 rpm for 15 minutes. Two ml of the organic phase (top layer) was transferred to a glass vial, dried at 37° C., under nitrogen, for approximately 1 hour, and then lyophilized for approximately 48 hours. The samples were then removed from the lyophilizer and each vial was reconstituted with 600 µl of solvent A (trimethylpentane/tetrahydrofuran (99:1). The samples were then recapped and vortexed for 5 minutes.

200 µl of each sample was then transferred to a pre-labeled 200 µl HPLC vial with 200 µL glass inserts. The HPLC vials were placed in the autosampler tray for the Agilent 1100 series HPLC unit. The Agilent 1100 HPLC system consisted of a thermostated autosampler, a quarternary pump, a column heater, and an A/D interface module. All components were controlled by Agilent ChemStation software. A Waters Spherisorb S3W 4.6×100 mm analytical column was maintained at 30° C. by the Agilent column heater unit. The HPLC autosampler was programmed to maintain the sample temperature at 20 C throughout the run.

10 uL of each sample was injected in triplicate into the column. Two solvents were used for the solvent gradient. Solvent A was an admixture of trimethylpentane and tetrahydrofuran (99:1). Solvent B was ethylacetate. The gradient utilized is described in the table below:

| Time (min) | Solv A (%) | Solv B (%) | Flow (mL/min) |
| --- | --- | --- | --- |
| 0 | 99 | 1 | 2 |
| 2 | 96 | 4 | 2 |
| 6 | 60 | 40 | 2 |
| 7 | 5 | 95 | 2 |
| 10 | 5 | 95 | 2 |
| 10.1 | 99 | 1 | 2 |

The Sedex 75 Evaporative Light Scattering Detector (ELSD) was operated at 45° C. with a gain of 5, and $N_2$ pressure maintained at 3.1 bar. Analog signal obtained by the instrument was sent to the Agilent A/D interface module where it was converted to a digital output. The conversion was based on a 10000-mAU/volt set point and the data rate was set at 10 Hz (0.03 min). The resulting digital output was then feed into the Agilent ChemStation software for integration of the peak area.

The results of the HPLC analysis are reported below in Table IV. The results are reported as the reduction in cholesterol ester (CE) and wax ester (WE) production, when compared to the vehicle control.

| Compound | Structure | % Reduction in CE | % Reduction in WE | Sum CE + WE |
|---|---|---|---|---|
| Example 1 | 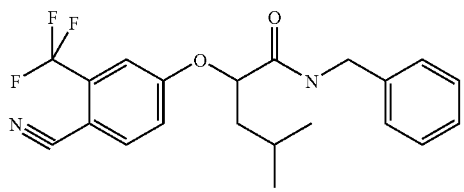 | 32% | 52% | 84% |
| Example 4 | 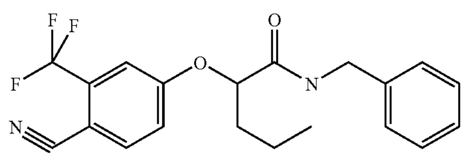 | 15% | 31% | 46% |

Columns 1 and 2 identify the compound by structure and Example number. Columns 3 through 5 show the effect the compounds had on the reduction of sebum components (CE and WE). The results are expressed as the difference from the vehicle control. A positive number reflects a decrease in the production of the sebum component being measured, i.e. cholesterol esters (CE) or wax esters (WE).

Column 3 shows the compounds ability to reduce the amount of cholesterol ester in the sebum sample. Column 4 shows the effect the compound had on the generation of wax ester. Wax esters are specific markers of the sebaceous glands and are not appreciably detected in any other layer of the skin. Wax ester is the largest component of sebum (approximately 25%). Thus reducing wax ester typically leads to significant reductions in sebum secretion. Column 5 is a summation of the results expressed in columns 3 and 4 (and is included to further elucidate relative differences in activity). As shown in Table IV, the androgen modulators of Formula I significantly decreased the production of cholesterol esters and wax esters.

What is claimed
1. A compound of the formula:

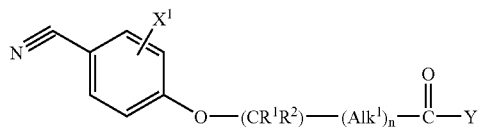

in which;
a) $X^1$ is represented by cyano, halogen or haloalkyl,
b) one of $R^1$ or $R^2$ is represented by $C_1$-$C_6$ alkyl which may be optionally substituted, and the other of $R^1$ or $R^2$ is represented by hydrogen or $C_1$-$C_6$ alkyl which may be optionally substituted,
c) $Alk^1$ is represented by a $C_1$-$C_2$ linear alkylene group, in which up to two hydrogen atoms are optionally replaced by a substitutent selected from the group consisting of $C_1$-$C_6$ alkyl optionally substituted, halogen, hydroxy, thiol, and cyano,
d) n is represented by the integer 0 or 1,
e) Y is represented by $NX^2X^3$,
f) $X^2$ is represented by hydrogen or ($C_1$-$C_6$) alkyl optionally substituted, and
g) $X^3$ is represented by ($C_6$-$C_{10}$)aryl($C_1$-$C_6$)alkyl, in which the alkyl and aryl moieties may each be optionally substituted,
or a pharmaceutically acceptable salt thereof.

2. A compound according to claim 1 in which one of $R^1$ or $R^2$ is hydrogen and the other of $R^1$ or $R^2$ is selected from the group consisting of isobutyl, propyl, n-butyl, isopropyl, and ethyl.

3. A compound according to claim 2 in which n is 0.

4. A compound according to claim 3 in which $X^1$ is trifluoromethyl and is located at the 3-position of the phenyl ring.

5. A compound according to claim 4 in which $X^2$ is hydrogen.

6. A compound according to claim 1 in which $X^1$ is represented by halogen or haloalkyl.

7. A pharmaceutical composition comprising a compound according to claim 1 in admixture with 1, or more, pharmaceutically acceptable excipients.

8. A topical pharmaceutical formulation comprising a compound according to claim 1 in admixture with 1 or more, pharmaceutically acceptable excipients suitable for dermal application.

9. A kit comprising a compound according to claim 1 packaged for retail distribution, which advises a consumer how to utilize the compound to alleviate a condition selected from the group consisting of acne, alopecia, and oily skin.

10. A compound according to claim 1 in which $X^1$ is represented by $CF_3$ and is located at the 3-position of the phenyl ring, $R^1$ is isobutyl or propyl, $R^2$ is hydrogen, and n is 0.

11. A compound according to claim 1 in which $X^1$ is represented by $CF_3$ and is located at the 3-position of the phenyl ring, $R^1$ is isobutyl, $R^2$ is hydrogen, n is 0, and $X^2$ is represented by hydrogen.

12. A compound according to claim 1 in which $X^1$ is represented by $CF_3$ and is located at the 3-position of the phenyl ring, R¹ is isobutyl or propyl, R² is hydrogen, n is 0, X² is represented by hydrogen and X³ is benzyl or phenethyl in which the phenyl ring is optionally substituted with at least one substituent selected from the group consisting of methoxy, ethoxy, hydroxy, and methyl.

13. A compound according to claim 1 selected from the group consisting of:
a) 2-(4-cyano-3-trifluoromethyl-phenoxy)-4-methyl-pentanoic acid benzylamide,
b) 2-(4-cyano-3-trifluoromethyl-phenoxy)-pentanoic acid benzylamide,
c) 2-(4-cyano-3-trifluoromethyl-phenoxy)-4-methyl-pentanoic acid [2-(4-methoxy-phenyl)-ethyl]-amide,
d) 2-(4-cyano-3-trifluoromethyl-phenoxy)-4-methyl-pentanoic acid (2-phenoxy-ethyl)-amide,
e) 2-(4-cyano-3-trifluoromethyl-phenoxy)-4-methyl-pentanoic acid -3-methoxy-benzylamide,
f) 2-(4-cyano-3-trifluoromethyl-phenoxy)-4-methyl-pentanoic acid [2-(4-methoxy-phenyl)-ethyl]amide,
g) 2-(4-cyano-3-trifluoromethyl-phenoxy)-4-methyl-pentanoic acid-2-methoxy-benzylamide,
h) 2-(4-cyano-3-trifluoromethyl-phenoxy)-4-methyl-pentanoic acid-2-ethoxy-benzylamide,
i) 2-(4-cyano-3-trifluoromethyl-phenoxy)-4-methyl-pentanoic acid-3-methyl-benzylamide, and,
j) 2-(4-cyano-3-trifiuoromethyl-phenoxy)-4-methyl-pentanoic acid-2-methyl-benzylamide.

14. A compound according to claim 1 selected from the group consisting of:
a) 2-(4-cyano-3-trifluoromethyl-phenoxy)-4-methyl-pentanoic acid-4-methoxy-benzylamide,
b) 2-(4-cyano-3-trifiuoromethyl-phenoxy)-pentanoic acid-3-methoxy-benzylamide,
c) 2-(4-cyano-3-trifluoromethyl-phenoxy)-pentanoic acid-2-methoxy-benzyiamide,
d) 2-(4-cyano-3-trifluoromethyl-phenoxy)-pentanoic acid-2-ethoxy-benzylamide,
e) 2-(4-cyano-3-trifluoromethyl-phenoxy)-pentanoic acid-3-methyl-benzylamide,
f) 2-(4-cyano-3-trifluoromethyl-phenoxy)-pentanoic acid-2-methyl-benzylamide,
g) 2-(4-cyano-3-trifluoromethyl-phenoxy)-pentanoic acid-2,4-dimethyl-benzylamide,
h) 2-(4-cyano-3-trifluoromethyl-phenoxy)-pentanoic acid-4-methoxy-benzylamide,
i) 2-(4-cyano-3-trifluoromethyl-phenoxy)-4-methyl-pentanoic acid-(2-p-tolyl-ethyl)-amide, and,
j) 2-(4-cyano-3-trifluoromethyl-phenoxy)-4-methyl-pentanoic acid-[2-(2-methoxy-phenyl)-ethyl]-amide.

15. A compound according to claim 1 selected from the group consisting of:
a) 2-(4-cyano-3-trifluoromethyl-phenoxy)-4-methyl-pentanoic acid-(2-m-tolyl-ethyl)-amide,
b) 2-(4-cyano-3-trifluoromethyl-phenoxy)-pentanoic acid-(2-p-tolyl-ethyl)-amide,
c) 2-(4-cyano-3-trifluoromethyl-phenoxy)-pentanoic acid-[2-(2-methoxy-phenyl)-ethyl]-amide,
d) 2-(4-cyano-3-trifluoromethyl-phenoxy)-pentanoic acid-(2-m-tolyl-ethyl)-amide,
e) 2-(4-cyano-3-trifluoromethyl-phenoxy)-4-methyl-pentanoic acid-(2-phenoxy-propyl)-amide,
f) 2-(4-cyano-3-trifluoromethyl-phenoxy)-pentanoic acid-(2-phenoxy-ethyl)-amide,
g) 2-(4-cyano-3-trifluoromethyl-phenoxy)-4-methyl-pentanoic acid-[2-(3-methoxy-phenyl)-ethyl]-amide,
h) 2-(4-cyano-3-trifluoromethyi-phenoxy)-4-methyl-pentanoic acid-[2-(4-hydroxy-phenyl)-ethyl]-amide,
i) 2-(4-cyano-3-trifiuoromethyl-phenoxy)-4-methyl-pentanoic acid benzyl-isopropyl-amide,
j) 2-(4-cyano-3-trifluoromethyl-phenoxy)-pentanoic acid-[2-(3-methoxy-phenyl)-ethyl]-amide,
k) 2-(4-cyano-3-trifluoromethyl-phenoxy)-pentanoic acid-[2-(4-hydroxy-phenyl)-ethyl]-amide,
l) 2-(4-cyano-3-trifluoromethyi-phenoxy)-pentanoic acid benzyl-isopropyl-amide,
m) 2-(4-cyano-3-trifluoromethyl-phenoxy)-4-methyl-pentanoic acid [1-(4-hydroxy-phenyl)-ethyl]-amide,
n) 2-(4-cyano-3-trifluoromethyl-phenoxy)-4-methyl-pentanoic acid 4-isopropyl-benzylamide,
o) 2-(4-cyano-3-trifluoromethyl-phenoxy)-4-methyl-pentanoic acid-3-methoxy-benzylamide, and,
p) 2-(4-cyano-3-trifluoromethyl-phenoxy)-4-methyl-pentanoic acid-4-methoxy-benzylamide.

16. A compound according to claim 1 selected from the group consisting of:
a) 2-(4-cyano-3-trifluoromethyl-phenoxy)-4-methyl-pentanoic acid-3,4-dihydroxy-benzylamide,
b) 2-(4-cyano-3-trifluoromethyl-phenoxy)-pentanoic acid (naphthalene-1-yl-methyl)-amide,
c) 2-(4-cyano-3-trifluoromethyl-phenoxy)-hexanoic acid benzylamide,
d) N-benzyl-2-(4-cyano-3-trifluoromethyl-phenoxy)-3-methyl-butyramide,
e) (R)- 2-(4-cyano-3-trifluoromethyl-phenoxy)-4-methyl-pentanoic acid benzylamide,
f) (R)-2-(4-cyano-3-trifluoromethyl-phenoxy)-pentanoic acid benzyiamide,
g) (R)-2-(cyano-3-trifluoromethyl-phenoxy)-pentanoic acid 2-methyl-benzylamide,
h) 2-(3-chloro-4-cyano-phenoxy)-pentanoic acid benzylamide, and,
i) 2-(3-chloro-4-cyano-phenoxy)-pentanoic acid [2-(4-hydroxy-phenyl)-ethyl]-amide.

17. A compound according to claim 1 selected from the group consisting of:
a) (S)-2-(3-chloro-4-cyano-phenoxy)-pentanoic acid benzylamide,
b) (S)-2-(3-chloro-4-cyano-phenoxy)-pentanoic acid [2-(4-hydroxy-phenyl)ethyl]amide,
c) (S)-2-(4-cyano-3-trifluoromethyl-phenoxy)-pentanoic acid-3-methyl-benzylamide,
d) (S)-2-(4-cyano-3-trifluoromethyl-phenoxy)-4-methyl-pentanoic acid-[2-(4-hydroxy-phenyl)-ethyl]-amide,
e) 2-(4-cyano-3-trifluoromethyl-phenoxy)-4-methyl-pentanoic acid-[1-(methoxy-phenyl)-ethyl]-amide,
f) (R—) 2-(4-cyano-3-trifluoromethyl-phenoxy)-4-methyl-pentanoic acid [2-4-hydroxy-phenyl)-ethyl]amide,
g) 2-(4-cyano-3-trifluoromethyl-phenoxy)-4-methyl-pentanoic acid (1-phenyl-ethyl)-amide,
h) 2-(4-cyano-3-trifluoromethyl-phenoxy)-penanoic acid[1-(4-methoxy-phenyl)-ethyl]-amide,
i) 2-(4-cyano-3-trifluoromethyl-phenoxy)-4-methyl-pentanoic acid [1-(4-hydroxy-phenyl)-ethyl]-amide,
j) 2-(4-cyano-3-trifluoromethyl-phenoxy)-pentanoic acid [1-(4-hydroxy-phenyl)-ethyl]-amide,
k) 2-(4-cyano-3-trifluoromethyl-phenoxy)-pentanoic acid [1-(4-hydroxy-phenyl)-ethyl]-amide,
l) 2-(4-cyano-3-trifluoromethyl-phenoxy)-4-methyl-pentanoic acid [I-hydroxy-phenyl)-ethyl]-amide,
m) 2-(4-cyano-3-trifluoromethyl-phenoxy)-4-methyl-pentanoic acid (1-phenyl-ethyl)-amide, and,
n) 2-(4-cyano-3-trifluoromethyl-phenoxy)-pentanoic acid [1-(methoxy-phenyl)-ethyl]-amide.

* * * * *